United States Patent
Mir et al.

(10) Patent No.: US 11,198,857 B2
(45) Date of Patent: *Dec. 14, 2021

(54) CASCADE/DCAS3 COMPLEMENTATION ASSAYS FOR IN VIVO DETECTION OF NUCLEIC ACID-GUIDED NUCLEASE EDITED CELLS

(71) Applicant: Inscripta, Inc., Boulder, CO (US)

(72) Inventors: Aamir Mir, Boulder, CO (US); Andrew Garst, Boulder, CO (US); Stephen Federowicz, Boulder, CO (US); Kyle Seamon, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/388,358

(22) Filed: Jul. 29, 2021

(65) Prior Publication Data

US 2021/0355467 A1 Nov. 18, 2021

Related U.S. Application Data

(63) Continuation of application No. 17/230,765, filed on Apr. 14, 2021, now Pat. No. 11,104,890, which is a continuation of application No. 17/123,067, filed on Dec. 15, 2020, now Pat. No. 11,008,557.

(60) Provisional application No. 62/949,472, filed on Dec. 18, 2019.

(51) Int. Cl.
*C12N 9/22* (2006.01)
*C12N 15/11* (2006.01)
*C12N 15/70* (2006.01)
*C12N 15/62* (2006.01)

(52) U.S. Cl.
CPC ............ *C12N 9/22* (2013.01); *C12N 15/11* (2013.01); *C12N 15/62* (2013.01); *C12N 15/70* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 6,391,582 B2 | 5/2002 | Ying et al. |
| 6,837,995 B1 | 1/2005 | Vassarotti et al. |
| 7,166,443 B2 | 1/2007 | Walker et al. |
| 8,332,160 B1 | 12/2012 | Platt et al. |
| 8,697,359 B1 | 4/2014 | Zhang et al. |
| 8,926,977 B2 | 1/2015 | Miller et al. |
| 9,260,505 B2 | 2/2016 | Weir et al. |
| 9,361,427 B2 | 6/2016 | Hillson |
| 9,499,855 B2 | 11/2016 | Newbold et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,011,849 B1 | 7/2018 | Gill et al. |
| 10,017,760 B2 | 7/2018 | Gill et al. |
| 10,227,576 B1 | 3/2019 | Cameron et al. |
| 10,266,851 B2 | 4/2019 | Chen |
| 10,704,033 B1 | 7/2020 | Kim et al. |
| 10,724,021 B1 | 7/2020 | Kim et al. |
| 10,745,678 B1 | 8/2020 | Kim et al. |
| 10,767,169 B1 | 9/2020 | Kim et al. |
| 10,837,021 B1 | 11/2020 | Tian et al. |
| 10,927,385 B2 | 2/2021 | Kannan et al. |
| 2002/0139741 A1 | 10/2002 | Kopf |
| 2004/0110253 A1 | 6/2004 | Kappler et al. |
| 2007/0020761 A1 | 1/2007 | Yu et al. |
| 2010/0076057 A1 | 3/2010 | Sontheimer et al. |
| 2011/0294217 A1 | 12/2011 | McConnell-Smith et al. |
| 2013/0236970 A1 | 9/2013 | Anneren et al. |
| 2014/0068797 A1 | 3/2014 | Doudna et al. |
| 2014/0199767 A1 | 7/2014 | Barrangou et al. |
| 2014/0242033 A1 | 8/2014 | Gruber et al. |
| 2014/0273226 A1 | 9/2014 | Wu et al. |
| 2015/0071898 A1 | 3/2015 | Liu et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0344549 A1 | 12/2015 | Muir et al. |
| 2016/0024529 A1 | 1/2016 | Carstens et al. |

(Continued)

FOREIGN PATENT DOCUMENTS

| EP | 2395087 | 12/2011 |
|---|---|---|
| EP | 3199632 | 8/2017 |

(Continued)

OTHER PUBLICATIONS

International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2021/012868, dated Mar. 26, 2021, p. 1-15.

(Continued)

*Primary Examiner* — Suzanne M Noakes
(74) *Attorney, Agent, or Firm* — Sarah Brashears; Dianna L. DeVore

(57) ABSTRACT

The present disclosure relates to methods and compositions that allow one to identify in vivo edited cells when employing nucleic-acid guided editing. Additionally provided are automated multi-module instruments for performing editing and selection methods and using the compositions.

20 Claims, 25 Drawing Sheets

(56) References Cited

U.S. PATENT DOCUMENTS

| | | |
|---|---|---|
| 2016/0053272 A1 | 2/2016 | Wurtzel et al. |
| 2016/0053304 A1 | 2/2016 | Wurtzel et al. |
| 2016/0076093 A1 | 3/2016 | Shendure et al. |
| 2016/0102322 A1 | 4/2016 | Ravinder et al. |
| 2016/0168592 A1 | 6/2016 | Church et al. |
| 2016/0264981 A1 | 9/2016 | Yang et al. |
| 2016/0281053 A1 | 9/2016 | Sorek et al. |
| 2016/0289673 A1 | 10/2016 | Huang et al. |
| 2016/0298134 A1 | 10/2016 | Chen et al. |
| 2016/0354487 A1 | 12/2016 | Zhang et al. |
| 2017/0002339 A1 | 1/2017 | Barrangou et al. |
| 2017/0022499 A1 | 1/2017 | Lu et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0369870 A1 | 12/2017 | Gill et al. |
| 2018/0028567 A1 | 2/2018 | Li et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0187149 A1 | 7/2018 | Ma et al. |
| 2018/0200342 A1 | 7/2018 | Bikard et al. |
| 2018/0230460 A1 | 8/2018 | Gill et al. |
| 2018/0230461 A1 | 8/2018 | Gill et al. |
| 2019/0017072 A1 | 1/2019 | Ditommaso et al. |
| 2019/0136230 A1 | 5/2019 | Sather et al. |
| 2019/0169605 A1 | 6/2019 | Masquelier et al. |
| 2019/0194650 A1 | 6/2019 | Gill et al. |
| 2019/0225928 A1 | 7/2019 | Masquelier et al. |
| 2019/0270987 A1 | 9/2019 | Masquelier et al. |
| 2020/0102580 A1* | 4/2020 | Mashimo ................ A01H 1/00 |
| 2020/0263197 A1 | 8/2020 | Cheng et al. |

FOREIGN PATENT DOCUMENTS

| | | |
|---|---|---|
| WO | WO2002/010183 | 2/2002 |
| WO | WO 2003/087341 | 10/2003 |
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO 2014/144495 | 9/2014 |
| WO | WO 2016/110453 | 7/2016 |
| WO | WO2016/110453 | 7/2016 |
| WO | WO 2017/053902 | 3/2017 |
| WO | WO 2017/078631 | 5/2017 |
| WO | WO 2017/083722 | 5/2017 |
| WO | WO 2017/106414 | 6/2017 |
| WO | WO2017/106414 | 6/2017 |
| WO | WO 2017/161371 | 9/2017 |
| WO | WO 2017/174329 | 10/2017 |
| WO | WO 2017/186718 | 11/2017 |
| WO | WO2017/212400 | 12/2017 |
| WO | WO2017/216392 | 12/2017 |
| WO | WO 2017/216392 | 12/2017 |
| WO | WO2017/223330 | 12/2017 |
| WO | WO 2017/223330 | 12/2017 |
| WO | WO 2018/031950 | 2/2018 |
| WO | WO 2018/071672 | 4/2018 |
| WO | WO 2018/083339 | 5/2018 |
| WO | WO 2018/191715 | 10/2018 |
| WO | WO2019/006436 | 1/2019 |
| WO | WO 2019/200004 | 10/2019 |
| WO | WO2019/209926 | 10/2019 |
| WO | WO 2020/005383 | 1/2020 |
| WO | WO2020/021045 | 1/2020 |

OTHER PUBLICATIONS

Anzalone et al., "Search-and-replace genome editing without doubles-strand breaks or donor DNA," Nature, Oct. 21, 2019, vol. 576, No. 7785, pp. 149-157.

Alvarez, et al., "In vivo diversification of target genomic sites using processive T7 RNA polymerase-base deaminase fusions blocked by RNA-guided dCas9", Dept.of Microbial Biotechnology and Systems Biology Program, Madrid, Spain, Jan. 1, 2019, p. 1-33.

International Search Report and Written Opinion for International Application No. PCT/US20/65168, dated Mar. 17, 2021, p. 1-15.

International Search Report and Written Opinion for International Application No. PCT/US2020/038345, dated Nov. 23, 2020, p. 1-13.

International Search Report and Written Opinion for International Application No. PCT/US21/12867, dated May 12, 2021, p. 1-17.

International Search Report and Written Opinion for International Application No. PCT/US2020/064727, dated Apr. 28, 2021, p. 1-13.

International Search Report and Written Opinion for International Application No. PCT/US21/29008, dated Aug. 24, 2021, p. 1-19.

International Search Report and Written Opinion for International Application No. PCT/US21/29011, dated Aug. 24, 2021, p. 1-20.

Bauer, et al., "Cell-microcarrier Adhesion to Gas-Liquid Interfaces and Foam", Biotechnol. Prog. 2000, 16, 125-132, Oct. 19, 1999.

Datlinger, et al., "Pooled CRISPR screening with single-cell transcriptome readout", Nature Methods, Jan. 10, 2017; p. 1-10, doi:10.1038/nmeth.4177.

Dixit, et al., "Perturb-Seq: Dissecting Molecular Circuits with Scalable Single-Cell RNA Profiling of Pooled Genetic Screens", Cell 167, p. 1853-1866, Dec. 15, 2016.

GE Healthcare Life Sciences, "Microcarrier Cell Culture Principles and Methods", 18-1140-62 AC, p. 1-23, Nov. 2013.

Jacobi, et al., "Simplified CRISPR tools for efficient genome editing and streamlined protocols for their delivery into mammalian cells and mouse zygotes", Methods 121-122, p. 16-28, Mar. 23, 2017.

Jaitin, et al., "Dissecting Immune Circuits by Linking CRISPR-Pooled Screens with Single-Cell RNA-Seq", Cell 167, p. 1883-1896, Dec. 15, 2016.

Kim, et al., "Formation of Thermoresponsive Poly(N-isopropylacrylamide)/Dextran Particles by Atom Transfer Radical Polymerization", Macromol. Rapid Commun., 24, p. 517-521, 2003.

Kimple, et al., "Overview of Affinity Tags for Protein Purification", Curr Protoc Protein Sci.; 73: Unit-9-9. Doi:10.1002/0471140864. ps0909s73, p. 1-26, Aug. 6, 2015.

Nienow, et al., "A potentially scalable method for the harvesting of hMSCs from microcarriers", Biochemical Engineering Journal 85, p. 79-88, Feb. 4, 2014.

Replogle, et al., "Direct capture of CRISPR guides enables scalable, multiplexed, and multi-omic Perturb-Seq", bioRxiv; doi:http://dx.doi.org/10.1101/503367, p. 1-26, Dec. 21, 2018.

Sivalingam, et al., "Superior Red Blood Cell Generation from Human Pluripotent Stem Cells Through a Novel Microcarrier-Based Embryoid Body Platform", Tissue Engineering: Part C, vol. 22, No. 8, p. 765-780, Jun. 9, 2016.

Bao, et al., "Genome-scale engineering of *Saccharomyces cerevisiae* with single-nucleotide precision", Nature Biotechnology, doi:10.1038/nbt.4132, pp. 1-6 (May 7, 2018).

Dicarlo, et al., "Genome engineering in *Saccharomyces cervisiae* using CRISPR-Case systems", Nucleic Acids Research, 41(7):4336-43 (2013).

Garst, et al., "Genome-wide mapping of mutations at single-nucleotide resolution for protein, metabolic and genome engineering", Nature Biotechnology, 35(1):48-59 (2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems", Nature Biotechnology, 31(3):233-41 (2013).

Jinek, et al., "A Programmable Dual-RNA-Guided DNA Endonuclease in Adaptive Bacterial Immunity", Science, 337:816-20 (2012).

Verwaal, et al., "CRISPR/Cpf1 enables fast and simple genome editing of *Saccharomyces cerevisiae*", Yeast, 35:201-11 (2018).

Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).

(56) References Cited

OTHER PUBLICATIONS

Roy, et cl., "Multiplexed precision genome editing with trackable genomic barcodes in yeast", Nature Biotechnolgy, doi:10.1038/nbt. 4137, pp. 1-16 (2018).
Dong, "Establishment of a highly efficient virus-inducible CRISPR/ Cas9 system in insect cells," Antiviral Res., 130:50-7(2016).
Epinat et al., "A novel engineered meganuclease induces homologous recombination in eukaryotic cells, e.g., yeast and mammalian cells", Nucleic Acids Research, 31(11): 2952-2962.
Farasat et al., "A Biophysical Model of CRISPR/Cas9 Activity for Rational Design of Genome Editing and Gene Regulation," PLoS Comput Biol., 29:12(1):e1004724 (2016).
Liu et al., "A chemical-inducible CRISPR-Cas9 system for rapid control of genome editing", Nature Chemical Biology, 12:980-987(2016).
Eklund, et al., "Altered target site specificity variants of the I-Ppol His-Cys bis homing endonuclease" Nucleic Acids Research, 35(17):5839-50 (2007).
Boles, et al., "Digital-to-biological converter for on-demand production of biologies", Nature Biotechnology, doi:10.1038/nbt.3859 (May 29, 2017).
Pines, et al., "Codon Compression Algorithms for Saturation Mutagenesis", ACS Synthetic Biology, 4:604-14 (2015).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Durai et al., "Zinc finger nucleases: custom-designed molecular scissors for genome engineering of plant and mammalian cells", Nucleic Acids Res., 33(18):5978-90 (2005).
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20(1): 81-9 (2009).
Miller et al., "A Tale nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US20/24341, dated Jun. 19, 2020, p. 1-9.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/ Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.
International Search Report and Written Opinion for International Application No. PCT/US19/57250, dated Feb. 25, 2020, p. 1-16.
International Search Report and Written Opinion for International Application No. PCT/US19/47135, dated Jun. 11, 2020, p. 1-15.

\* cited by examiner

CASCADE/DCAS3 COMPLEMENTATION ASSAYS FOR IN VIVO DETECTION OF NUCLEIC ACID-GUIDED NUCLEASE EDITED CELLS

CROSS-REFERENCE TO RELATED APPLICATIONS

This application is a continuation of U.S. Ser. No. 17/230,765, filed 14 Apr. 2021; which is a continuation of U.S. Ser. No. 17/123,067, filed Dec. 15, 2020, now U.S. Pat. No. 11,008,557; which claims priority to U.S. Ser. No. 62/949,472, filed Dec. 18, 2019, all of which are incorporated by reference.

FIELD OF THE INVENTION

The present disclosure relates to methods and compositions to allow for in vivo identification of specific nucleic-acid sequences, such as intended edit sequences present in cells when employing nucleic-acid guided editing, as well as automated multi-module instruments for performing the editing and selection methods.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The ability to make precise, targeted changes to the genome of living cells has been a long-standing goal in biomedical research and development. Recently, various nucleases have been identified that allow for manipulation of gene sequences, and hence gene function. The nucleases include nucleic acid-guided nucleases, which enable researchers to generate permanent edits in live cells. Of course, it is desirable to be able to identify cells that have been properly edited in a resulting cell population; however, in many instances the percentage of edited cells resulting from nucleic acid-guided nuclease editing can be in the single digits.

There is thus a need in the art of nucleic acid-guided nuclease editing for improved methods, compositions, modules and instruments for rapid and accurate identification in vivo of cells that have been properly edited. The present disclosure addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure relates to methods, compositions, modules and automated multi-module cell processing instruments that allow one to generate nucleic acid-guided nuclease edited cells and to identify in vivo the cells that have been properly edited in the resulting population of cells where the majority—and perhaps the vast majority—of cells have not been edited. The present methods and compositions employ a split protein reporter system that uses a type I CRISPR-Cas system. The split protein reporter system exploits the natural mechanism of Cas3 (CAS3) recruitment upon Cascade complex target recognition. The recruitment of Cas3 to the Cascade complex initiates an intracellular signal amplification event specific to the high fidelity targeting of the Cascade complex to a specified DNA sequence, in this case, a DNA sequence comprising a desired edit. By attaching one-half of a split protein to a deactivated Cas3 (dCas3) and the other half of the split protein to a protein component of the Cascade, a system is created in which the two halves of the split protein only come together when the Cascade complex (e.g., Cascade and crRNA) has formed a discriminatory R-loop and complexed with the correct target DNA sequence. In one embodiment, the split protein is T7 RNA polymerase (T7 RNAP). Upon recognition of the Cascade complex fusion and the target sequence (e.g., an intended edit) and upon recruitment of the deactivated Cas3-N-terminal T7 RNAP fusion protein, the two halves of the split T7 RNAP are brought into proximity resulting in an active T7 polymerase. The active T7 polymerase is capable of transcribing, e.g., a coding sequence for a reporter gene under the control of a T7 promoter, which in turn allows for isolation of a population of cells with intended edits.

Thus, there is provided in one embodiment herein a nucleic acid-guided nuclease editing system comprising: a Cascade-T7-RNAP fusion protein coding sequence in a vector backbone; a dCas3-T7-RNAP fusion protein coding sequence in a vector backbone; a sequence for an edit-discriminating (or "edit-targeting") gRNA in a vector backbone, wherein the edit-discriminating (or "edit-targeting") gRNA recognizes a rationally-designed edited locus in a genome sequence but does not recognize the locus in the genome sequence in an unedited or incorrectly-edited condition; and a coding sequence for a reporter gene under the control of a T7 promoter. In some aspects, Cascade-T7 RNAP fusion protein coding sequence comprises the C-terminus of cas5c (in type I-C systems) or the C-terminus of cse1 or casA (in type I-E systems) and the C-terminus of the T7 RNAP (e.g., amino acids 181-883) while the dCas3-T7 RNAP fusion protein coding sequence comprises the N-terminus of dCas3 and the N-terminus of the T7-RNAP (e.g., amino acids 1-179). Alternatively in some aspects, the Cascade-T7 RNAP fusion protein coding sequence comprises the N-terminus of cas5c (in type I-C systems) or the N-terminus of cse1 or casA (in type I-E systems) and the N-terminus of the T7 RNAP (e.g., amino acids 1-179) while the dCas3-T7 RNAP fusion protein coding sequence comprises the C-terminus of dCas3 and the C-terminus of the T7-RNAP (e.g., amino acids 181-883). In some aspects, the reporter gene is a coding sequence for a fluorescent protein, and some aspects, the fluorescent protein is green fluorescent protein or blue fluorescent protein. In yet other aspects, the reporter gene is a coding sequence for luciferase, and in some aspects, the luciferase is firefly luciferase or *Renilla* luciferase. In yet other aspects, the reporter gene encodes for a broccoli or spinach RNA aptamer. In yet other aspects, the reporter gene is a coding sequence for an antibiotic resistance gene. In yet other aspects, the reporter gene is a coding sequence for a cell surface receptor protein.

In some aspects of the nucleic acid-guided nuclease editing system, the Cascade-T7-RNAP-C-terminal fusion protein coding sequence, the dCas3-T7-RNAP-N-terminal fusion protein coding sequence, the sequence for the edit-discriminating gRNA, and coding sequence for a reporter gene under the control of a T7 promoter are all on the same vector and in alternative aspects, the Cascade-T7-RNAP-C-terminal fusion protein coding sequence, the dCas3-T7-RNAP-N-terminal fusion protein coding sequence, the sequence for the edit-discriminating gRNA, and coding sequence for a reporter gene under the control of a T7 promoter are on two or more different vectors.

Yet another embodiment provides a cell comprising the Cascade-T7-RNAP-C-terminal fusion protein coding sequence in a vector backbone; the dCas3-T7-RNAP-N-terminal fusion protein coding sequence in a vector backbone; the sequence for an edit-discriminating gRNA in a vector backbone, wherein the edit-discriminating gRNA recognizes a rationally-designed edited locus in a genome sequence but does not recognize the locus in the genome sequence in an unedited or incorrectly-edited condition; and the coding sequence for a reporter gene under the control of a T7 promoter.

Yet other embodiments provide a method for in vivo identification of edited cells comprising: transforming the cells with nucleic acid-guided nuclease editing components comprising a nucleic acid-guided nuclease, a gRNA homologous to a genomic locus, and a donor DNA homologous to a genomic locus; transforming the cells with a nucleic acid-guided nuclease editing system comprising a Cascade-T7-RNAP-C-terminal fusion protein coding sequence in a vector backbone, a dCas3-T7-RNAP-N-terminal fusion protein coding sequence in a vector backbone, a sequence for an edit-discriminating gRNA in a vector backbone, wherein the edit-discriminating gRNA recognizes a rationally-designed edited locus in a genome sequence but does not recognize the locus in the genome sequence in an unedited or incorrectly-edited condition, and a coding sequence for a reporter gene under the control of a T7 promoter; allowing the nucleic acid-guided nuclease, the gRNA, and donor DNA to edit the genomic locus in the cells; allowing the Cascade-T7-RNAP-C-terminal fusion protein coding sequence, edit-discriminating gRNA and Cascade-T7-RNAP-C-terminal fusion protein coding sequence bind to the edited genomic locus thereby reconstituting T7 RNAP activity; and providing conditions for T7 RNAP to bind and activate the T7 promoter thereby transcribing the reporter gene.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which.

It should be understood that the drawings are not necessarily to scale, and that like reference numbers refer to like features.

DETAILED DESCRIPTION

Figure 1A:
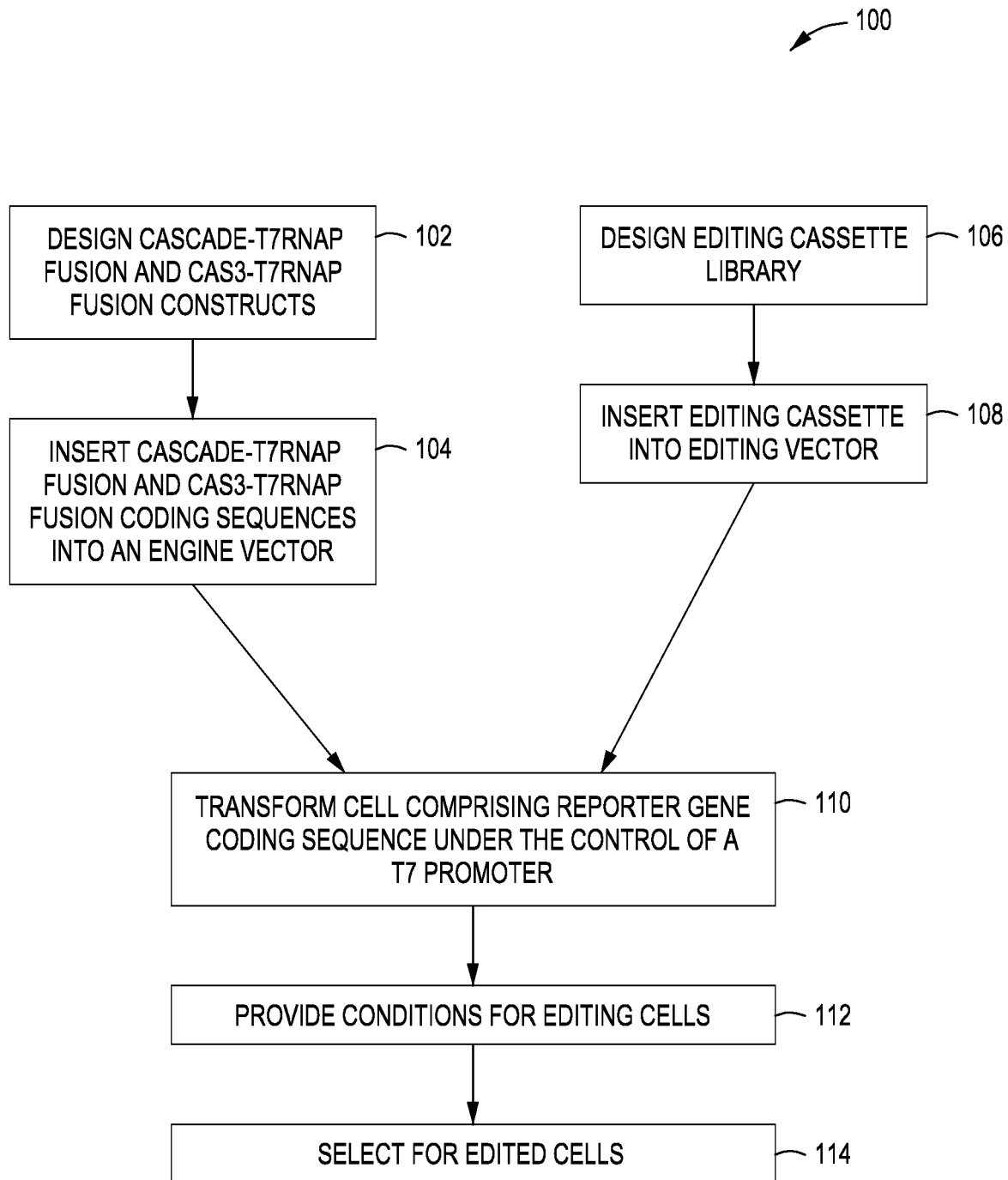
FIG. 1A is a simple process diagram for performing Type I nucleic acid-guided nuclease selection using a Cascade-T7-RNAP-C-terminal fusion protein, a dCas3-T7-RNAP-N-terminal fusion protein, an edit-discriminating (or "edit-targeting") gRNA and a reporter gene (collectively, a "split protein reporter system").

All of the functionalities described in connection with one embodiment of the methods, devices or instruments described herein are intended to be applicable to the additional embodiments of the methods, devices and instruments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of molecular biology (including recombinant techniques), cell biology, biochemistry, and genetic engineering technology, which are within the skill of those who practice in the art. Such conventional techniques and descriptions can be found in standard laboratory manuals such as Green and Sambrook, *Molecular Cloning: A Laboratory Manual*. 4th, ed., Cold Spring Harbor Laboratory Press, Cold Spring Harbor, N.Y., (2014); *Current Protocols in Molecular Biology*, Ausubel, et al. eds., (2017); Neumann, et al., *Electroporation and Electrofusion in Cell Biology*, Plenum Press, New York, 1989; and Chang, et al., *Guide to Electroporation and Electrofusion*, Academic Press, California (1992), all of which are herein incorporated in their entirety by reference for all purposes. Nucleic acid-guided nuclease techniques can be found in, e.g., *Genome Editing and Engineering from TALENs and CRISPRs to Molecular Surgery*, Appasani and Church (2018); and *CRISPR: Methods and Protocols*, Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

The term "complementary" as used herein refers to Watson-Crick base pairing between nucleotides and specifically refers to nucleotides hydrogen-bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term "Cascade" or "Cascade effector" refers to the protein effector complexes of type I CRISPR-Cas systems. The term "Cascade complex" refers to the Cascade effector complex further comprising a crRNA.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to nucleic acid that is designed to introduce a DNA sequence modification (insertion, deletion, substitution) into a locus (e.g., a target genomic DNA sequence or cellular target sequence) by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the genomic target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the genomic target sequence.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

As used herein, the terms "protein" and "polypeptide" are used interchangeably. Proteins may or may not be made up entirely of amino acids.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible.

As used herein a "reporter gene" is a gene used as an indicator for gene expression and other cellular events, such as, e.g., genes coding for luciferase or fluorescent proteins. In the present context, a reporter gene is used as a proxy for genome editing.

As used herein the term "selectable marker" refers to a gene introduced into a cell, which confers a trait suitable for artificial selection. General use selectable markers are well-known to those of ordinary skill in the art and include ampicillin/carbenicillin, kanamycin, chloramphenicol, nourseothricin N-acetyl transferase, erythromycin, tetracycline, gentamicin, bleomycin, streptomycin, puromycin, hygromycin, blasticidin, and G418 or other selectable markers may be employed.

The term "specifically binds" as used herein includes an interaction between two molecules, e.g., an engineered peptide antigen and a binding target, with a binding affinity represented by a dissociation constant of about $10^{-7}$M, about $10^{-8}$M, about $10^{-9}$ M, about $10^{-10}$ M, about $10^{-11}$M, about $10^{-12}$M, about $10^{-13}$M, about $10^{-14}$M or about $10^{-15}$M.

The terms "target genomic DNA sequence", "cellular target sequence", "target sequence", or "genomic target locus" refer to any locus in vitro or in vivo, or in a nucleic acid (e.g., genome or episome) of a cell or population of cells, in which a change of at least one nucleotide is desired using a nucleic acid-guided nuclease editing system. The target sequence can be a genomic locus or extrachromosomal locus. The term "edited target sequence" or "edited locus" refers to a target genomic sequence or target sequence after editing has been performed, where the edited target sequence comprises the desired edit.

The term "variant" may refer to a polypeptide or polynucleotide that differs from a reference polypeptide or polynucleotide but retains essential properties. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide may be a conservatively modified variant. A substituted or inserted amino acid residue may or may not be one encoded by the genetic code (e.g., a non-natural amino acid). A variant of a polypeptide may be naturally occurring, such as an allelic variant, or it may be a variant that is not known to occur naturally.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. In some embodiments of the present methods, two vectors—an engine vector, comprising the coding sequences for a nuclease, and an editing vector, comprising the gRNA sequence and the donor DNA sequence—are used. In alternative embodiments, all editing components, including the nuclease, gRNA sequence, and donor DNA sequence are all on the same vector (e.g., a combined editing/engine vector). In some embodiments, the coding sequences for the Cascade-T7-RNAP-C-terminal fusion protein, the dCas3-T7-RNAP-N-terminal fusion protein, edit-discriminating gRNA and the reporter gene under the control of a T7 promoter are all located on a single reporter vector, but in other embodiments, one or more of these components may be located on the engine vector, the editing vector, or one or more different reporter vectors.

Nuclease-Directed Genome Editing Generally

The compositions and methods described herein are employed to allow one to perform nuclease-directed genome editing to introduce desired edits to a population of cells and then allow one to quickly identify edited cells in vivo. In some embodiments, recursive cell editing is performed where edits are introduced in successive rounds of editing to cells that have been edited in previous rounds. A nucleic acid-guided nuclease complexed with an appropriate synthetic guide nucleic acid in a cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby. In certain aspects, the nucleic acid-guided nuclease editing system may use two separate guide nucleic acid molecules that combine to function as a guide nucleic acid, e.g., a CRISPR RNA (crRNA) and trans-activating CRISPR RNA (tracrRNA). In other aspects and preferably, the guide nucleic acid is a single guide nucleic acid construct that includes both 1) a guide sequence capable of hybridizing to a genomic target locus, and 2) a scaffold sequence capable of interacting or complexing with a nucleic acid-guided nuclease.

In general, a guide nucleic acid (e.g., gRNA) complexes with a compatible nucleic acid-guided nuclease and can then hybridize with a target sequence, thereby directing the nuclease to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. In cases where the guide nucleic acid comprises RNA, the gRNA may be encoded by a DNA sequence on a polynucleotide molecule such as a plasmid, linear construct, or the coding sequence may and preferably does reside within an editing cassette. Methods and compositions for designing and synthesizing editing cassettes are described in U.S. Pat. Nos. 10,240,167; 10,266,849; 9,982,278; 10,351,877; 10,364,442; and 10,435,715; and U.S. Ser. No. 16/275,465, filed 14 Feb. 2019, all of which are incorporated by reference herein.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In general, to generate an edit in the target sequence, the gRNA/nuclease complex binds to a target sequence as determined by the guide RNA, and the nuclease recognizes a protospacer adjacent motif (PAM) sequence adjacent to the target sequence. The target sequence can be any polynucleotide endogenous or exogenous to the cell, or in vitro. For example, the target sequence can be a polynucleotide residing in the nucleus of the cell. A target sequence can be a sequence encoding a gene product (e.g., a protein) or a non-coding sequence (e.g., a regulatory polynucleotide, an intron, a PAM, a control sequence, or "junk" DNA).

The guide nucleic acid may be and preferably is part of an editing cassette that encodes the donor nucleic acid that targets a cellular target sequence. Alternatively, the guide nucleic acid may not be part of the editing cassette and instead may be encoded on the editing vector backbone. For example, a sequence coding for a guide nucleic acid can be assembled or inserted into a vector backbone first, followed by insertion of the donor nucleic acid in, e.g., an editing cassette. In other cases, the donor nucleic acid in, e.g., an editing cassette can be inserted or assembled into a vector backbone first, followed by insertion of the sequence coding for the guide nucleic acid. Preferably, the sequence encoding the guide nucleic acid and the donor nucleic acid are located together in a rationally-designed editing cassette and are simultaneously inserted or assembled via gap repair into a linear plasmid or vector backbone to create an editing vector.

The target sequence is associated with a proto-spacer mutation (PAM), which is a short nucleotide sequence recognized by the gRNA/nuclease complex. The precise preferred PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve target site recognition fidelity, decrease target site recognition fidelity, or increase the versatility of a nucleic acid-guided nuclease.

In most embodiments, the genome editing of a cellular target sequence both introduces a desired DNA change to a cellular target sequence, e.g., the genomic DNA of a cell, and removes, mutates, or renders inactive a proto-spacer mutation (PAM) region in the cellular target sequence (e.g., renders the target site immune to further nuclease binding). Rendering the PAM at the cellular target sequence inactive precludes additional editing of the cell genome at that cellular target sequence, e.g., upon subsequent exposure to a nucleic acid-guided nuclease complexed with a synthetic guide nucleic acid in later rounds of editing. Thus, cells having the desired cellular target sequence edit and an altered PAM can be selected for by using a nucleic acid-guided nuclease complexed with a synthetic guide nucleic acid complementary to the cellular target sequence. Cells that did not undergo the first editing event will be cut rendering a double-stranded DNA break, and thus will not continue to be viable. The cells containing the desired cellular target sequence edit and PAM alteration will not be cut, as these edited cells no longer contain the necessary PAM site and will continue to grow and propagate.

As for the nuclease component of the nucleic acid-guided nuclease editing system, a polynucleotide sequence encoding the nucleic acid-guided nuclease can be codon optimized for expression in particular cell types, such as bacterial, yeast, and mammalian cells. The choice of the nucleic acid-guided nuclease to be employed depends on many factors, such as what type of edit is to be made in the target sequence and whether an appropriate PAM is located close to the desired target sequence. Nucleases of use in the methods described herein include but are not limited to Cas 9, Cas 12/CpfI, MAD2, or MAD7 or other MADzymes.

Another component of the nucleic acid-guided nuclease system is the donor nucleic acid comprising homology to the cellular target sequence. The donor nucleic acid is on the same vector and even in the same editing cassette as the guide nucleic acid and preferably is (but not necessarily is) under the control of the same promoter as the editing gRNA (that is, a single promoter driving the transcription of both the editing gRNA and the donor nucleic acid). The donor nucleic acid is designed to serve as a template for homologous recombination with a cellular target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length, and up to 2, 3, 4, 5, 6, 7, 8, 9, 10, 11, 12, 13 and up to 20 kb in length if combined with a dual gRNA architecture as described in U.S. Ser. No. 16/275,465, filed 14 Feb. 2019. In certain preferred aspects, the donor nucleic acid can be provided as an oligonucleotide of between 20-300 nucleotides, more preferably between 50-250 nucleotides. The donor nucleic acid comprises a region that is complementary to a portion of the cellular target sequence (e.g., a homology arm). When optimally aligned, the donor nucleic acid overlaps with (is complementary to) the cellular target sequence by, e.g., about 20, 25, 30, 35, 40, 50, 60, 70, 80, 90 or more nucleotides. In many embodiments, the donor nucleic acid comprises two homology arms (regions complementary to the cellular target sequence) flanking the mutation or difference between the donor nucleic acid and the cellular target sequence. The donor nucleic acid comprises at least one mutation or alteration compared to the cellular target sequence, such as an insertion, deletion, modification, or any combination thereof compared to the cellular target sequence.

As described in relation to the gRNA, the donor nucleic acid is preferably provided as part of a rationally-designed editing cassette, which is inserted into an editing plasmid backbone (in yeast, preferably a linear plasmid backbone) where the editing plasmid backbone may comprise a promoter to drive transcription of the editing gRNA and the donor DNA when the editing cassette is inserted into the editing plasmid backbone. Moreover, there may be more than one, e.g., two, three, four, or more editing gRNA/donor nucleic acid rationally-designed editing cassettes inserted into an editing vector; alternatively, a single rationally-designed editing cassette may comprise two to several editing gRNA/donor DNA pairs, where each editing gRNA is under the control of separate different promoters, separate like promoters, or where all gRNAs/donor nucleic acid pairs are under the control of a single promoter. In some embodiments the promoter driving transcription of the editing gRNA and the donor nucleic acid (or driving more than one editing gRNA/donor nucleic acid pair) is optionally an inducible promoter.

In addition to the donor nucleic acid, an editing cassette may comprise one or more primer sites. The primer sites can be used to amplify the editing cassette by using oligonucleotide primers; for example, if the primer sites flank one or more of the other components of the editing cassette. In addition, the editing cassette may comprise a barcode. A barcode is a unique DNA sequence that corresponds to the donor DNA sequence such that the barcode can identify the edit made to the corresponding cellular target sequence. The barcode typically comprises four or more nucleotides. In addition, the editing cassette may comprise a set of FLP/FRT or Cre/Lox recombination sites that enable controlled deletion of the donor DNA and or gRNA while preserving the barcode. In some embodiments, the editing cassettes comprise a collection or library editing gRNAs and of donor nucleic acids representing, e.g., gene-wide or genome-wide libraries of editing gRNAs and donor nucleic acids. The library of editing cassettes is cloned into vector backbones where, e.g., each different donor nucleic acid is associated with a different barcode. Also, in preferred embodiments, an editing vector or plasmid encoding components of the nucleic acid-guided nuclease system further encodes a nucleic acid-guided nuclease comprising one or more nuclear localization sequences (NLSs), such as about or more than about 1, 2, 3, 4, 5, 6, 7, 8, 9, 10, or more NLSs, particularly as an element of the nuclease sequence. In some embodiments, the engineered nuclease comprises NLSs at or near the amino-terminus, NLSs at or near the carboxy-terminus, or a combination.

Increasing Efficiency of Identifying Nuclease-Directed Edited Cells In Vivo Via a Split Protein Reporter System The present disclosure is drawn to increasing the efficiency of in vivo detection of edits made to live cells after nucleic acid-guided nuclease editing has been performed. Genome editing using nucleic acid-guided nuclease editing technology requires precise repair of nuclease-induced DNA strand breaks (e.g., double-strand breaks or single-strand nicks) via homologous recombination with an editing vector. Double-strand DNA breaks in cells caused by nucleic acid-guided nucleases have three main outcomes: 1) cell death if the break is not repaired; 2) non-homologous end joining (NHEJ), which repairs the break without a homologous repair template often leading to indels; and 3) homologous recombination (HR), which uses auxiliary (here, exogenous) homologous DNA (e.g., a donor DNA sequence from an editing cassette inserted into the editing vector) to repair the break. The present methods and compositions are drawn to in vivo identification of cells that have been edited by HR.

The present methods and compositions utilize, in addition to a nucleic acid-guided nuclease editing system as described above, a split protein reporter system comprising a type I CRISPR-Cas system, two fusion constructs, an edit-discriminating or edit-targeting gRNA and a reporter gene under the control of a T7 promoter. The core feature of CRISPR-Cas types and subtypes are different cas proteins, which are highly genetically and functionally diverse. There are three major types of CRISPR-Cas systems, which are distinguished from one another by unique signature genes: Cas3 in type I systems, Cas9 in type II systems, and Cas10 in type III systems. Type I CRISPR systems utilize a two-component structure to degrade target DNA, which is exploited in the present methods and compositions to provide a handle for identifying edited cells in vivo. In type I systems, the signature gene, Cas3, encodes a large protein with helicase activity.

The effector complexes of type I CRISPR-Cas systems display elaborate architectures, made up of Cas5c, Cas7c and Cas8c protein subunits in Type I-C systems, and CasA/Cse1, Cse2, Cas7e, Cas5e, and Cas6e in Type I-E systems. The Cas5c subunit binds the 5'-handle of the crRNA and interacts with the large Cas8c subunit. The Type I-C Cascade complex (made up of Cas5c, Cas7c, Cas8C and crRNA) binds to a target DNA sequence and forms an R-loop complex with the RNA guide and target DNA strand. After R-loop formation, the Cascade complex recruits Cas3 which nicks the non-target strand and begins processive DNA degradation. Either Type I-C or Type I-E systems may be utilized, although Type-I-C systems are preferred due to their smaller size, e.g., resulting in a reduced payload delivery to the cells of choice.

The present methods and compositions are drawn to the natural mechanism of Cas3 recruitment upon Cascade complex target recognition to initiate an intracellular signal amplification event specific to the high fidelity targeting of the Cascade complex to a specified DNA sequence. By attaching one-half of a split protein to a deactivated Cas3 (dCas3) and the other half of the split protein to a protein component of the Cascade, a system is created in which the two split portions of the protein only come together when the Cascade complex has formed a discriminatory R-loop and complexed with the correct target DNA sequence.

Many different proteins may be used according to the present methods; however, one of particular interest is the T7 RNA polymerase (T7 RNAP) which has already been validated for use in protein complementation assays. (See, e.g., Shis, et al., PNAS, 110: and 5028-5033 (2013); and Pu, et al., Nat Chem Biol 13:432-438 (2017).) In the case of split T7 RNAP, in a preferred embodiment the C-terminus T7 RNAP fragment (e.g., amino acids 181-883) is fused to the Cascade complex via the C-terminus of the Cas5c (in a Type-I-C system) or the C-terminus of the casA/cse1 protein (in a Type-I-E system) and the N-terminus of the T7 RNAP fragment (e.g., amino acids 1-179) is fused to the N-terminus of the deactivated dCas3 protein. The cascade proteins comprising the C-terminus of the T7 RNAP complexes with an edit-discriminating crRNA forming a Cascade complex. Upon recognition of the Cascade complex and the target sequence (e.g., where the target sequence comprises an intended edit and an R-loop is formed) and upon recruitment of dCas3 fused to the N-terminus of T7 RNAP, the two halves of the split T7 RNAP are brought into proximity resulting in an active T7 polymerase. The active T7 polymerase is capable of transcribing linear or circular dsDNA fragments introduced into the cell.

In the present methods, the linear dsDNA to be transcribed by the T7 polymerase comprises a coding sequence for a reporter gene such as, in an exemplary embodiment, a luciferase gene (or a fluorescent protein such as green fluorescent protein coding sequence, an antibiotic resistance gene, a gene coding for a cell surface marker, etc.) under the control of a T7 promoter. The reconstituted T7 polymerase binds the T7 promoter and transcribes the reporter gene coding sequence. In the case where the reporter gene codes for luciferase, the transcribed sequence is translated into the luciferase enzyme. If the substrate of luciferase, luciferin, is present, luciferase will catalyze a two-step oxidation process to yield light, which results in enough fluorescence to sort cells in a FACS, which in turn allows for isolation of a population of cells with intended edits.

It should be noted that one of ordinary skill in the art given the present disclosure, that although the discussion herein focuses on fusing the C-terminal portion of T7 RNAP to the C-terminus of the cascade protein complex (e.g., the C-terminus of cas5c in type I-C systems or the C-terminus of cse1 or casA in type I-E systems) and the N-terminal portion of the T7 RNAP to the N-terminus of dCas3, alternative embodiments envision fusing the C-terminal portion of T7 RNAP to the C-terminus of dCas3 and the N-terminal portion of the T7 RNAP to the N-terminus of the cascade protein complex (e.g., the N-terminus of cas5c in type I-C systems or the N-terminus of cse1 or casA in type I-E systems). Additionally, other combinations of a split protein reporter system utilizing a type I CRISPR-Cas system may be envisioned as long as the combinations involve the formation of a cascade complex upon recognition of an intended edit in a target DNA sequence, formation of an R-loop, recruitment of dCas3 and reconstitution of activity of the split protein.

FIG. 1A is a simple process diagram for in vivo detection of cells that have been properly edited via nucleic acid-guided nuclease editing. In a first step of method 100, Cascade-T7-RNAP-C-terminal fusion and dCas3-T7-RNAP-N-terminal fusion constructs are synthesized 102. The appropriate "split" between the N-terminal and C-terminal portions of the T7 RNAP to produce a reconstituted polymerase once the two portions are in proximity with one another may be determined empirically. The polymerase is "split" at a point where there is no spontaneous association between the N-terminal and C-terminal portions of the T7 RNAP in the absence of physical proximity due to the association of dCas3 with the Cascade complex; however, the "split" must allow association of the N-terminal and C-terminal portions of the polymerase—and reconstitution of polymerase activity—in the presence of the association of dCas3 with the Cascade complex. Once the proper "split" for the polymerase is determined, appropriate Cascade-T7-RNAP fusion and dCas3-T7-RNAP fusion constructs can be designed and synthesized. In one embodiment, the N-terminal portion of the T7 RNAP comprises approximately amino acids 1-179 of the T7 RNAP protein and the C-terminal portion of the T7 RNAP comprises approximately amino acids 181-883 of the T7 RNAP protein. In one exemplary embodiment, the C-terminal portion of T7 RNAP is fused to the C-terminus of the cascade protein complex (e.g., the C-terminus of cas5c in type I-C systems or the C-terminus of cse1 or casA in type I-E systems) and the N-terminal portion of the T7 RNAP if fused to the N-terminus of dCas3.

Once synthesized, the appropriate Cascade-T7-RNAP-C-terminal fusion and dCas3-T7-RNAP-N-terminal fusion constructs are inserted into a vector 104 to be transformed 110 into cells of choice. In this exemplary embodiment, the cells of choice comprise the coding sequence of a reporter gene under the control of a T7 promoter and comprise a sequence for the edit-discriminating or edit-targeting gRNA. However, in alternative embodiments, the coding sequence of the reporter gene under the control of the T7 promoter and/or the edit-discriminating gRNA may be located on a reporter vector with the fusion constructs (as described below) or on the engine or editing vector (where these vectors are described briefly below). Also in this exemplary embodiment, the Cascade-T7-RNAP-C-terminal fusion and dCas3-T7-RNAP-N-terminal fusion constructs are located on the engine vector with the nucleic acid-guided nuclease coding sequence. In alternative embodiments, the Cascade-T7-RNAP-C-terminal fusion and dCas3-T7-RNAP-N-terminal fusion constructs may be contained on a single reporter vector separate from the engine vector (along with, e.g., the coding sequence for the reporter gene under the control of the T7 promoter and/or the edit-discriminating gRNA) where both fusion constructs are under the control of the same promoter or under the control of different promoters. In yet another embodiment, the Cascade-T7-RNAP-C-terminal fusion and dCas3-T7-RNAP-N-terminal fusion constructs may be contained on separate reporter vectors (e.g., see FIGS. 8A-8D). In yet another alternative, one or both of the Cascade-T7-RNAP-C-terminal fusion and dCas3-T7-RNAP-N-terminal fusion constructs may be stably integrated into the cellular genome.

The reporter gene as envisioned herein is a gene used as an indicator of proper genome editing and is under the control of a T7 promoter. The T7 promoter is the promoter for the bacteriophage T7 RNA polymerase, which is 19 base pairs in length. Reporter genes are used widely in molecular biology for gene expression and to study cellular events. Typically, a reporter gene is cloned into an expression vector that is then transformed or transfected into cells. The cells then may be assayed for the presence of the reporter by directly measuring the reporter protein itself such as in systems with reporters such as fluorescent proteins such as GFP, RFP and BFP, cell surface markers or antibiotic resistance, or by measuring the enzymatic activity of the reporter protein on a substrate (e.g., luciferase) or measuring fluorescence of a compound in the presence of a fluorogen such as systems with, e.g., RNA aptamers.

In the present methods and compositions, the reporter gene is under the control of the T7 promoter and the reporter gene is transcribed only upon reconstitution of the activity of T7 RNAP via proximity of the Cascade-T7-RNAP-C-terminal fusion construct and dCas3-T7-RNAP-N-terminal fusion construct when the Cascade complex recognizes and binds to the edited target locus. Although fluorescent proteins such as green fluorescent protein and blue fluorescent proteins may be employed, in some embodiments the compositions employ a luciferase reporter assay, which provides increased sensitivity, dynamic range and versatility over fluorescent proteins. Alternatively, RNA aptamers such as spinach and broccoli can also be expressed as a reporter gene under control of a T7 promoter and exhibit fluorescence in the presence of DFHBI ((5Z)-5-[(3,5-Difluoro-4-hydroxyphenyl)methylene]-3,5-dihydro-2-methyl-3-(2,2,2-trifluoroethyl)-4H-imidazol-4-one). Bioluminescent reporter assays have the advantage over fluorescent assays in that they deliver 10-1,000-fold higher assay sensitivity. The luciferase reporter technology as may be employed herein is based on the interaction of the enzyme luciferase (the coding sequence for which is the "reporter gene") and the luminescent substrate luciferin, which releases light by the process of bioluminescence. Two commonly-employed luciferases are firefly luciferase, a 61 kDa enzyme which requires no post-translational modifications, and Renilla luciferase, a 36 kDa enzyme which also requires no post-translational modifications. By coupling the T7 promoter to the coding sequence of the luciferase gene, the binding of the Cascade complex with the C-terminal T7 RNAP fusion and the dCas3-N-terminal T7 RNAP to the edited target locus to reconstitute T7 RNAP activity can be detected. Further, as mentioned above, the reporter gene may comprise an antibiotic resistance gene such that edited cells may be identified by antibiotic resistance, or the reporter gene may comprise a cell surface marker protein such that the cells may be sorted via antibodies to the cell surface marker protein.

A fourth component of the split protein reporter system is an edit-discriminating gRNA. The edit-discriminating gRNA is engineered specifically to bind to a target sequence that has been properly edited, and not to unedited (e.g., wild type) or incorrectly-edited sequences. In this instance, the edit-discriminating gRNA is not part of an editing cassette comprising a donor DNA (or homology arm). Instead, the edit-discriminating gRNA is used to recruit dCas3 to the Cascade complex; that is, the edit-discriminating gRNA is used for sequence recognition and not to facilitate an edit.

Thus, the nucleic acid-guided nuclease editing components and the split protein reporter system components must be transformed or transfected into the cell of interest. Transformation is intended to include to a variety of art-recognized techniques for introducing an exogenous nucleic acid sequence (e.g., engine and/or editing vectors) into a target cell, and the term "transformation" as used herein includes all transformation and transfection techniques. Such methods include, but are not limited to, electroporation, lipofection, optoporation, injection, microprecipitation, microinjection, liposome, particle bombardment, sonoporation, laser-induced poration, bead transfection, calcium phosphate or calcium chloride co-precipitation, or DEAE-dextran-mediated transfection. Cells can also be prepared for vector uptake using, e.g., a sucrose, sorbitol or glycerol wash. Additionally, hybrid techniques that exploit the capabilities of mechanical and chemical transfection methods can be used, e.g., magnetofection, a transfection methodology that combines chemical transfection with mechanical methods. In another example, cationic lipids may be deployed in combination with gene guns or electroporators. Suitable materials and methods for transforming or transfecting target cells can be found, e.g., in Green and Sambrook, *Molecular Cloning: A Laboratory Manual*, 4th, ed., Cold Spring Harbor Laboratory Press, Cold Spring Harbor, N.Y., 2014). The present automated methods using the automated multi-module cell processing instrument utilize flow-through electroporation such as the exemplary device shown in FIGS. 5B-5F.

Simultaneously or next, an editing cassette library is designed 106. Methods and compositions for designing and synthesizing editing cassettes are described in U.S. Pat. Nos. 10,240,167; 10,266,849; 9,982,278; 10,351,877; 10,364,442; and 10,435,715; and U.S. Ser. No. 16/275,465, filed 14 Feb. 2019. U.S. Ser. No. 16/275,465, filed 14 Feb. 2019 describes compound editing cassettes that are used in some embodiments of the compositions and methods described herein. Compound editing cassettes are editing cassettes comprising more than one gRNA and more than one donor DNA. Once designed and synthesized 106, the library of editing cassettes is amplified, purified and inserted 108 into an editing vector to produce a library of editing vectors. The library of editing vectors is then transformed into the cells that have already been transformed with the Cascade-T7-RNAP-C-terminal fusion and dCas3-T7-RNAP-N-terminal fusion constructs 110. In alternative embodiments, the editing vector, engine vector and reporter vector(s) may be transformed into the cells simultaneously. In yet other embodiments, one or more of the components for the split protein reporter system may be integrated into the cellular genome.

Once transformed, the cells are allowed to recover and selection optionally is performed to select for cells transformed with the reporter vector(s), engine vector and/or editing vector, all of which most often comprise a selectable marker. As described above, drug selectable markers such as ampicillin/carbenicillin, kanamycin, chloramphenicol, nourseothricin N-acetyl transferase, erythromycin, tetracycline, gentamicin, bleomycin, streptomycin, puromycin, hygromycin, blasticidin, and G418 or other selectable markers may be employed. At a next step, conditions are provided such that editing takes place 112. For example, if any of the editing components, such as, e.g., one or both of the nuclease or gRNA/donor DNA cassette, are under the control of an inducible promoter, conditions are provided that activate the inducible promoter(s). Once the cells have been edited 112, the cells are selected (e.g., sorted) 114, this time via, e.g., luminescence. Once the cells have been sorted such that the cells are enriched for edited cells, the edited cells may be used in research or may be grown to a desired OD to be made electrocompetent again, followed by another round of editing.

Figure 1B:
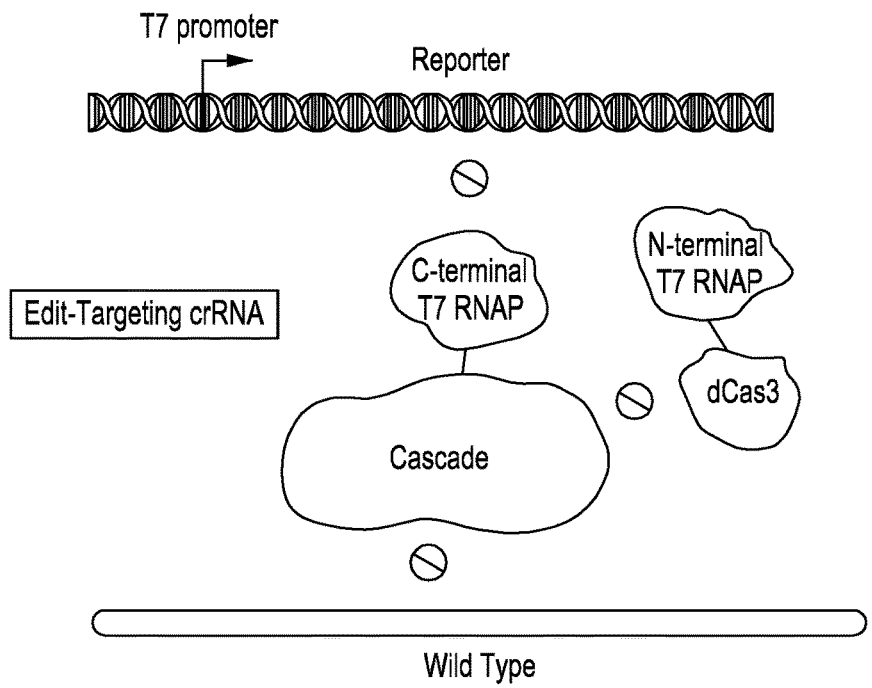
FIG. 1B is a simplified schematic of the components of a split protein system where a Cascade-T7-RNAP-C-terminal fusion protein in complex with an edit-discriminating (or edit-targeting) gRNA does not bind to a wild type (e.g., unedited) genomic target sequence.

FIG. 1B is a simplified schematic of the components of a split protein system where a gRNA does not bind to the wild type (e.g., unedited) genomic target sequence. At top of FIG. 1B is a reporter gene such as luciferase under the control of a T7 promoter. Also seen are an edit-discriminating or edit-targeting gRNA, a Cascade-T7-RNAP-C-terminal fusion construct and a dCas3-C-T7-RNAP-N-terminal fusion construct. In this instance the target genomic sequence is a "wild type" or unedited sequence, which is not recognized by the edit-discriminating gRNA. Because the edit-discriminating gRNA does not recognize the wild type genomic sequence, the Cascade-T7-RNAP-C-terminal fusion construct and edit-discriminating gRNA fail to form an R-loop complex at the genomic locus of interest. Without the formation of the R-loop at the genomic locus of interest, the dCas3-T7-RNAP-N-terminal fusion construct is not recruited to the locus of interest and the N-terminal and C-terminal portions of T7 RNAP are not brought into proximity. Without the N-terminal and C-terminal portions of T7 RNAP being brought into proximity, the activity of the T7 RNAP is not reconstituted, the T7 promoter is not activated, and the reporter gene is not transcribed (or translated). That is, the reporter is silent because the Cascade complex and dCas3 fail to bind the genomic target sequence such that the T7 RNAP may be "reconstituted" and activated.

Figure 1C:
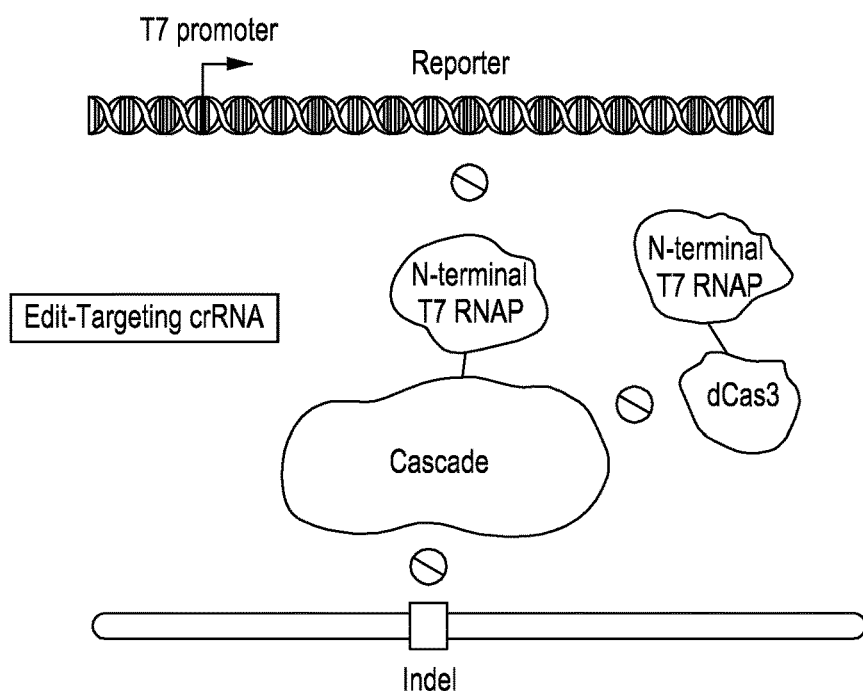
FIG. 1C is a simplified schematic of the components of a split protein system where there is an edited genomic target sequence, but the edit is not a desired, intended edit. Thus, an edit-discriminating gRNA transcript in complex with Cascade-T7-RNAP-C-terminal fusion does not recognize and bind to the genomic target sequence, form a Cascade complex and recruit the dCas3-T7-RNAP-N-terminal fusion protein to the incorrectly-edited target genomic sequence.

FIG. 1C is a simplified schematic of the components of a split protein system where there is an edited genomic target sequence, but the edited genomic target sequence is not a correct or desired edit. In this instance, the edit-discriminating gRNA does not bind to the incorrectly-edited genomic target sequence. At top of FIG. 1C, like FIG. 1B, is a reporter gene such as luciferase under the control of a T7 promoter. Also seen are a gRNA, a Cascade-T7-RNAP-C-terminal fusion construct and a dCas3-T7-RNAP-N-terminal fusion construct. Here, the target genomic sequence comprises an "indel" or incorrectly-edited sequence resulting from, e.g., an edit caused by non-homologous end joining (NHEJ), which repairs the double-strand break in the target genome without homologous repair rather than by homologous recombination (HR), which results in a precise, desired edit. The indel (e.g., incorrect edit), like the wild type genomic target sequence, is not recognized by the edit-discriminating gRNA. Because the edit-discriminating gRNA does not recognize the incorrectly-edited genomic sequence, the Cascade-T7-RNAP-C-terminal fusion construct and gRNA fail to form an R-loop complex at the genomic locus. Without the formation of the R-loop complex at the locus of interest, the dCas3-T7-RNAP-N-terminal fusion construct is not recruited to the locus of interest and the N-terminal and C-terminal portions of T7 RNAP are not brought into proximity. Without the N-terminal and C-terminal portions of T7 RNAP being brought into proximity, the activity of the T7 RNAP is not reconstituted, the T7 promoter is not activated, and the reporter gene is not transcribed (or translated). That is, like the process depicted in FIG. 1B, the reporter is silent because the Cascade complex and dCas3 fail to bind the genomic target sequence such that the T7 RNAP may be "reconstituted" and activated.

Figure 1D:
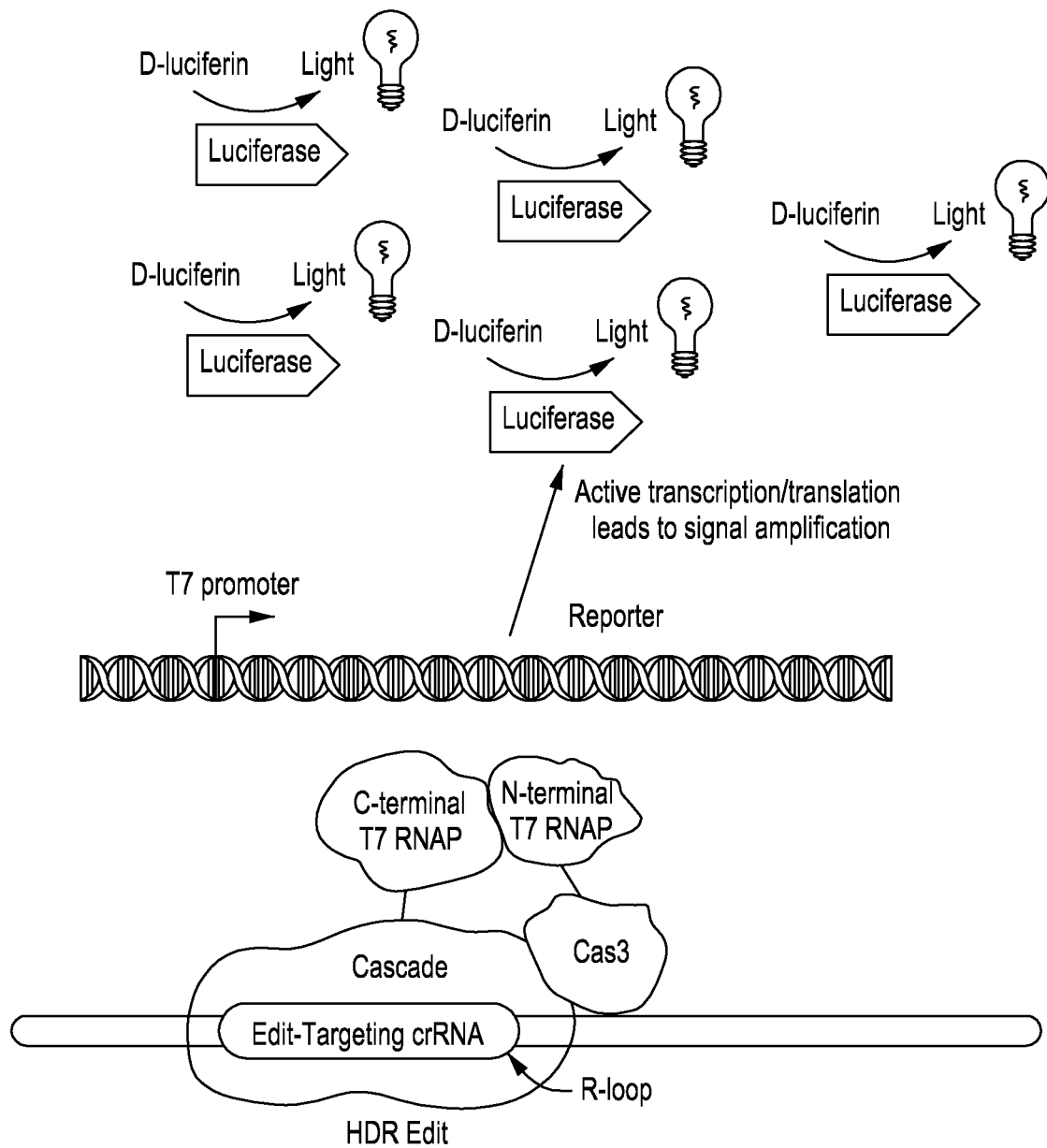
FIG. 1D is a simplified schematic of the components of a split protein system where there is a properly-edited genomic target sequence, an edit-discriminating gRNA transcript in complex with a Cascade-T7-RNAP-C-terminal fusion that binds the properly-edited genomic target sequence, forms an active R-loop and thereby recruits the dCas3-T7-RNAP-N-terminal fusion protein to the edited genomic sequence. The recruitment of the dCas3-T7-RNAP-N-terminal fusion protein brings the N-terminal and C-terminal portions of the T7 RNAP protein into functional proximity.

FIG. 1D is a simplified schematic of the components of a split protein system where there is a properly-edited genomic target sequence and the reporter gene is activated. At top of FIG. 1D is a reporter gene such as luciferase under the control of a T7 promoter. Also seen are an edit-discriminating gRNA, a Cascade-T7-RNAP-C-terminal fusion construct and a dCas3-T7-RNAP-N-terminal fusion construct bound to a genomic target sequence. In this instance the target genomic sequence is a properly-edited sequence, which is recognized by the edit-discriminating gRNA. Now the edit-discriminating gRNA and Cascade-T7-RNAP-C-terminal fusion construct can form an R-loop complex at the target genomic locus and the dCas3-T7-RNAP-N-terminal fusion construct may now be recruited to the target genomic locus thereby bringing the N-terminal and C-terminal portions of T7 RNAP into functional proximity. With the N-terminal and C-terminal portions of T7 RNAP being brought into functional proximity, the activity of the T7 RNAP is reconstituted and the T7 promoter is activated, thereby transcribing the reporter gene which in this embodiment is luciferase. Also seen in this FIG. 1D are schematics illustrating the transcribed (and translated) luciferase enzyme catalyzing the conversion of D-luciferin (the substrate) into detectable luminescence.

Figure 2A:
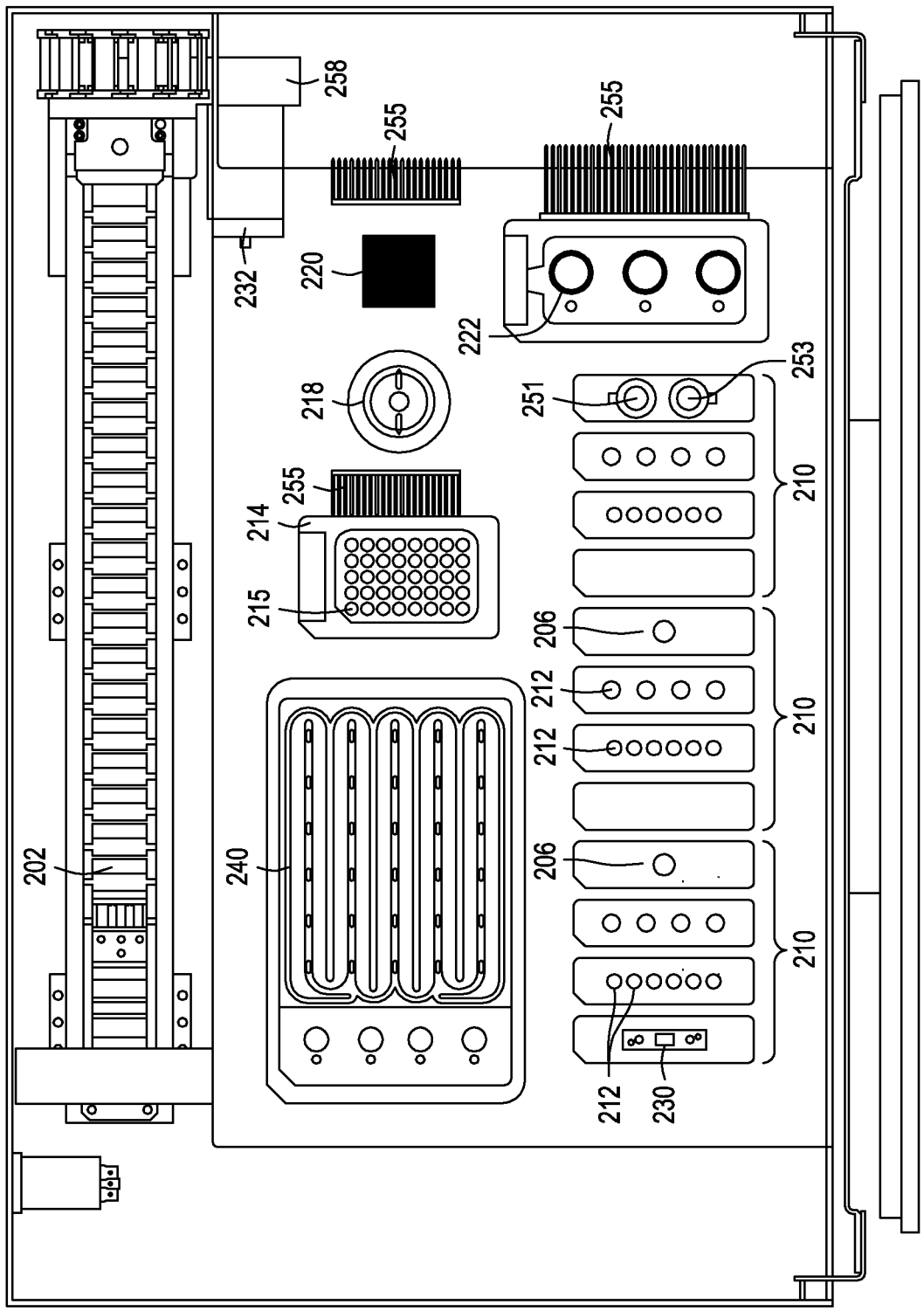
FIGS. 2A-2C depict three different views of an exemplary automated multi-module cell processing instrument for performing nucleic acid-guided nuclease editing employing a split protein reporter system.

Automated Cell Editing Instruments and Modules to Perform Nucleic Acid-Guided Nuclease Editing in Cells Automated Cell Editing Instruments FIG. 2A depicts an exemplary automated multi-module cell processing instrument 200 to, e.g., perform one of the exemplary workflows comprising a split protein reporter system as described herein. The instrument 200, for example, may be and preferably is designed as a stand-alone desktop instrument for use within a laboratory environment. The instrument 200 may incorporate a mixture of reusable and disposable components for performing the various integrated processes in conducting automated genome cleavage and/or editing in cells without human intervention. Illustrated is a gantry 202, providing an automated mechanical motion system (actuator) (not shown) that supplies XYZ axis motion control to, e.g., an automated (i.e., robotic) liquid handling system 258 including, e.g., an air displacement pipettor 232 which allows for cell processing among multiple modules without human intervention. In some automated multi-module cell processing instruments, the air displacement pipettor 232 is moved by gantry 202 and the various modules and reagent cartridges remain stationary; however, in other embodiments, the liquid handling system 258 may stay stationary while the various modules and reagent cartridges are moved. Also included in the automated multi-module cell processing instrument 200 are reagent cartridges 210 comprising reservoirs 212 and transformation module 230 (e.g., a flow-through electroporation device as described in detail in relation to FIGS. 5B-5F), as well as wash reservoirs 206, cell input reservoir 251 and cell output reservoir 253. The wash reservoirs 206 may be configured to accommodate large tubes, for example, wash solutions, or solutions that are used often throughout an iterative process. Although two of the reagent cartridges 210 comprise a wash reservoir 206 in FIG. 2A, the wash reservoirs instead could be included in a wash cartridge where the reagent and wash cartridges are separate cartridges. In such a case, the reagent cartridge 210 and wash cartridge may be identical except for the consumables (reagents or other components contained within the various inserts) inserted therein.

In some implementations, the reagent cartridges 210 are disposable kits comprising reagents and cells for use in the automated multi-module cell processing/editing instrument 200. For example, a user may open and position each of the reagent cartridges 210 comprising various desired inserts and reagents within the chassis of the automated multi-module cell editing instrument 200 prior to activating cell processing. Further, each of the reagent cartridges 210 may be inserted into receptacles in the chassis having different temperature zones appropriate for the reagents contained therein.

Also illustrated in FIG. 2A is the robotic liquid handling system 258 including the gantry 202 and air displacement pipettor 232. In some examples, the robotic handling system 258 may include an automated liquid handling system such as those manufactured by Tecan Group Ltd. of Mannedorf, Switzerland, Hamilton Company of Reno, Nev. (see, e.g., WO2018015544A1), or Beckman Coulter, Inc. of Fort Collins, Colo. (see, e.g., US20160018427A1). Pipette tips may be provided in a pipette transfer tip supply (not shown) for use with the air displacement pipettor 232.

Inserts or components of the reagent cartridges 210, in some implementations, are marked with machine-readable indicia (not shown), such as bar codes, for recognition by the robotic handling system 258. For example, the robotic liquid handling system 258 may scan one or more inserts within each of the reagent cartridges 210 to confirm contents. In other implementations, machine-readable indicia may be marked upon each reagent cartridge 210, and a processing system (not shown, but see element 237 of FIG. 2B) of the automated multi-module cell editing instrument 200 may identify a stored materials map based upon the machine-readable indicia. In the embodiment illustrated in FIG. 2A, a cell growth module comprises a cell growth vial 218 (described in greater detail below in relation to FIGS. 3A-3D). Additionally seen is the TFF module 222 (described above in detail in relation to FIGS. 4A-4E). Also illustrated as part of the automated multi-module cell processing instrument 200 of FIG. 2A is a singulation module 240 (e.g., a solid wall isolation, incubation and normalization device (SWIIN device) is shown here) described herein in relation to FIGS. 6C-6F, served by, e.g., robotic liquid handing system 258 and air displacement pipettor 232. Additionally seen is a selection module 220. Also note the placement of three heatsinks 255.

Figure 2B:
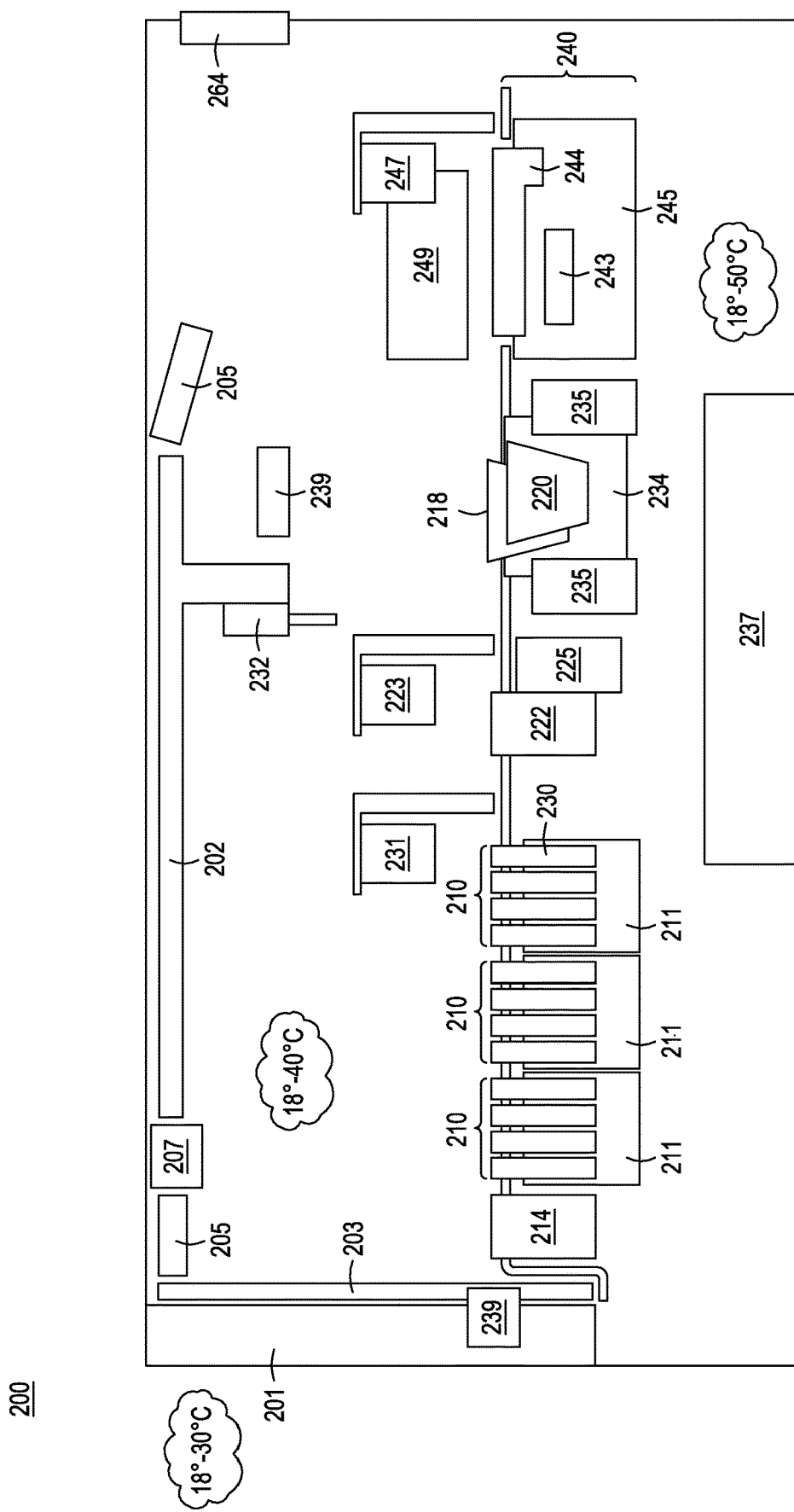

FIG. 2B is a simplified representation of the contents of the exemplary multi-module cell processing instrument 200 depicted in FIG. 2A. Cartridge-based source materials (such as in reagent cartridges 210), for example, may be positioned in designated areas on a deck of the instrument 200 for access by an air displacement pipettor 232. The deck of the multi-module cell processing instrument 200 may include a protection sink such that contaminants spilling, dripping, or overflowing from any of the modules of the instrument 200 are contained within a lip of the protection sink. Also seen are reagent cartridges 210, which are shown disposed with thermal assemblies 211 which can create temperature zones appropriate for different regions. Note that one of the reagent cartridges also comprises a flow-through electroporation device 230 (FTEP), served by FTEP interface (e.g., manifold arm) and actuator 231. Also seen is TFF module 222 with adjacent thermal assembly 225, where the TFF module is served by TFF interface (e.g., manifold arm) and actuator 223. Thermal assemblies 225,235, and 245 encompass thermal electric devices such as Peltier devices, as well as heatsinks, fans and coolers. The rotating growth vial 218 is within a growth module 234, where the growth module is served by two thermal assemblies 235. Selection module is seen at 220. Also seen is the SWIIN module 240, comprising a SWIIN cartridge 244, where the SWIIN module also comprises a thermal assembly 245, illumination 243 (in this embodiment, backlighting), evaporation and condensation control 249, and where the SWIIN module is served by SWIIN interface (e.g., manifold arm) and actuator 247. Also seen in this view is touch screen display 201, display actuator 203, illumination 205 (one on either side of multi-module cell processing instrument 200), and cameras 239 (one illumination device on either side of multi-module cell processing instrument 200). Finally, element 237 comprises electronics, such as circuit control boards, high-voltage amplifiers, power supplies, and power entry; as well as pneumatics, such as pumps, valves and sensors.

Figure 2C:
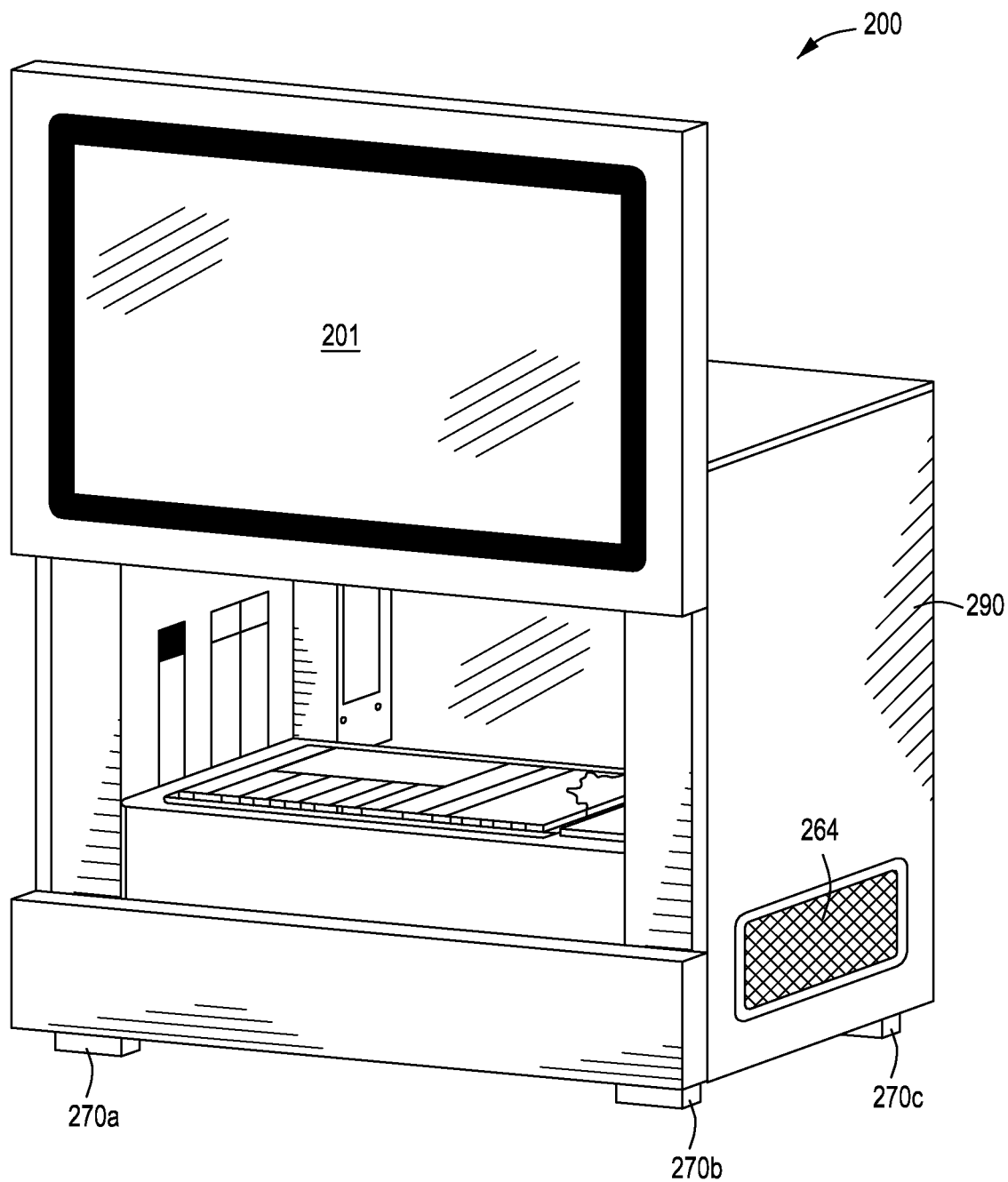

FIG. 2C illustrates a front perspective view of multi-module cell processing instrument 200 for use in as a desktop version of the automated multi-module cell editing instrument 200. For example, a chassis 290 may have a width of about 24-48 inches, a height of about 24-48 inches and a depth of about 24-48 inches. Chassis 290 may be and preferably is designed to hold all modules and disposable supplies used in automated cell processing and to perform all processes required without human intervention; that is, chassis 290 is configured to provide an integrated, stand-alone automated multi-module cell processing instrument. As illustrated in FIG. 2C, chassis 290 includes touch screen display 201, cooling grate 264, which allows for air flow via an internal fan (not shown). The touch screen display provides information to a user regarding the processing status of the automated multi-module cell editing instrument 200 and accepts inputs from the user for conducting the cell processing. In this embodiment, the chassis 290 is lifted by adjustable feet 270a, 270b, 270c and 270d (feet 270a-270c are shown in this FIG. 2C). Adjustable feet 270a-270d, for example, allow for additional air flow beneath the chassis 290.

Inside the chassis 290, in some implementations, will be most or all of the components described in relation to FIGS. 2A and 2B, including the robotic liquid handling system disposed along a gantry, reagent cartridges 210 including a flow-through electroporation device, a rotating growth vial 218 in a cell growth module 234, a tangential flow filtration module 222, a SWIIN module 240 as well as interfaces and actuators for the various modules. In addition, chassis 290 houses control circuitry, liquid handling tubes, air pump controls, valves, sensors, thermal assemblies (e.g., heating and cooling units) and other control mechanisms. For examples of multi-module cell editing instruments, see U.S. Pat. No. 10,253,316, issued 9 Apr. 2019; U.S. Pat. No. 10,329,559, issued 25 Jun. 2019; U.S. Pat. No. 10,323,242, issued 18 Jun. 2019; U.S. Pat. No. 10,421,959, issued 24 Sep. 2019; U.S. Pat. No. 10,465,185, issued 5 Nov. 2019; and U.S. Ser. No. 16/412,195, filed 14 May 2019; Ser. No. 16/571,091, filed 14 Sep. 2019; and Ser. No. 16/666,964, filed 29 Oct. 2019, all of which are herein incorporated by reference in their entirety.

The Rotating Cell Growth Module

Figure 3A:
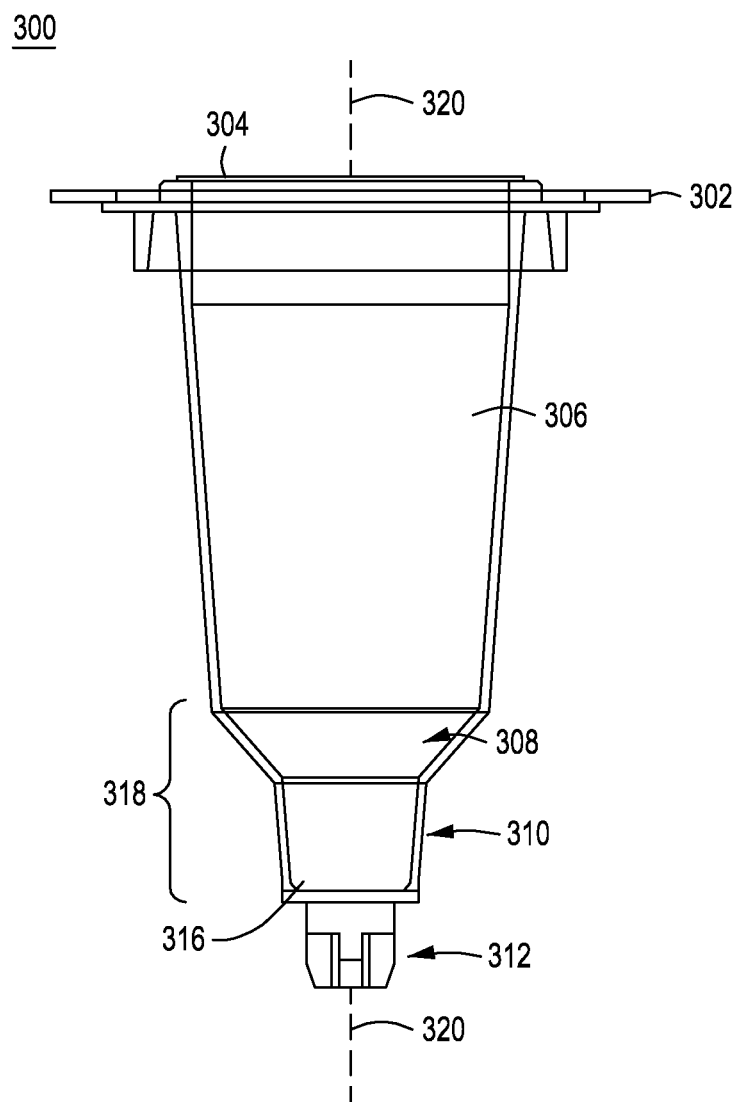
FIG. 3A depicts one embodiment of a rotating growth vial for use with the cell growth module described herein and in relation to FIGS. 3B-3D.

FIG. 3A shows one embodiment of a rotating growth vial 300 for use with the cell growth device and in the automated multi-module cell processing instruments described herein. The rotating growth vial 300 is an optically-transparent container having an open end 304 for receiving liquid media and cells, a central vial region 306 that defines the primary container for growing cells, a tapered-to-constricted region 318 defining at least one light path 310, a closed end 316, and a drive engagement mechanism 312. The rotating growth vial 300 has a central longitudinal axis 320 around which the vial rotates, and the light path 310 is generally perpendicular to the longitudinal axis of the vial. The first light path 310 is positioned in the lower constricted portion of the tapered-to-constricted region 318. Optionally, some embodiments of the rotating growth vial 300 have a second light path 308 in the tapered region of the tapered-to-constricted region 318. Both light paths in this embodiment are positioned in a region of the rotating growth vial that is constantly filled with the cell culture (cells+growth media) and are not affected by the rotational speed of the growth vial. The first light path 310 is shorter than the second light path 308 allowing for sensitive measurement of OD values when the OD values of the cell culture in the vial are at a high level (e.g., later in the cell growth process), whereas the second light path 308 allows for sensitive measurement of OD values when the OD values of the cell culture in the vial are at a lower level (e.g., earlier in the cell growth process).

The drive engagement mechanism 312 engages with a motor (not shown) to rotate the vial. In some embodiments, the motor drives the drive engagement mechanism 312 such that the rotating growth vial 300 is rotated in one direction only, and in other embodiments, the rotating growth vial 300 is rotated in a first direction for a first amount of time or periodicity, rotated in a second direction (i.e., the opposite direction) for a second amount of time or periodicity, and this process may be repeated so that the rotating growth vial 300 (and the cell culture contents) are subjected to an oscillating motion. Further, the choice of whether the culture is subjected to oscillation and the periodicity therefor may be selected by the user. The first amount of time and the second amount of time may be the same or may be different. The amount of time may be 1, 2, 3, 4, 5, or more seconds, or may be 1, 2, 3, 4 or more minutes. In another embodiment, in an early stage of cell growth the rotating growth vial 400 may be oscillated at a first periodicity (e.g., every 60 seconds), and then a later stage of cell growth the rotating growth vial 300 may be oscillated at a second periodicity (e.g., every one second) different from the first periodicity.

The rotating growth vial 300 may be reusable or, preferably, the rotating growth vial is consumable. In some embodiments, the rotating growth vial is consumable and is presented to the user pre-filled with growth medium, where the vial is hermetically sealed at the open end 304 with a foil seal. A medium-filled rotating growth vial packaged in such a manner may be part of a kit for use with a stand-alone cell growth device or with a cell growth module that is part of an automated multi-module cell processing system. To introduce cells into the vial, a user need only pipette up a desired volume of cells and use the pipette tip to punch through the foil seal of the vial. Open end 304 may optionally include an extended lip 402 to overlap and engage with the cell growth device. In automated systems, the rotating growth vial 400 may be tagged with a barcode or other identifying means that can be read by a scanner or camera (not shown) that is part of the automated system.

The volume of the rotating growth vial 300 and the volume of the cell culture (including growth medium) may vary greatly, but the volume of the rotating growth vial 300 must be large enough to generate a specified total number of cells. In practice, the volume of the rotating growth vial 400 may range from 1-250 mL, 2-100 mL, from 5-80 mL, 10-50 mL, or from 12-35 mL. Likewise, the volume of the cell culture (cells+growth media) should be appropriate to allow proper aeration and mixing in the rotating growth vial 400. Proper aeration promotes uniform cellular respiration within the growth media. Thus, the volume of the cell culture should be approximately 5-85% of the volume of the growth vial or from 20-60% of the volume of the growth vial. For example, for a 30 mL growth vial, the volume of the cell culture would be from about 1.5 mL to about 26 mL, or from 6 mL to about 18 mL.

The rotating growth vial 300 preferably is fabricated from a bio-compatible optically transparent material—or at least the portion of the vial comprising the light path(s) is transparent. Additionally, material from which the rotating growth vial is fabricated should be able to be cooled to about 4° C. or lower and heated to about 55° C. or higher to accommodate both temperature-based cell assays and long-term storage at low temperatures. Further, the material that is used to fabricate the vial must be able to withstand temperatures up to 55° C. without deformation while spinning. Suitable materials include cyclic olefin copolymer (COC), glass, polyvinyl chloride, polyethylene, polyamide, polypropylene, polycarbonate, poly(methyl methacrylate (PMMA), polysulfone, polyurethane, and co-polymers of these and other polymers. Preferred materials include polypropylene, polycarbonate, or polystyrene. In some embodiments, the rotating growth vial is inexpensively fabricated by, e.g., injection molding or extrusion.

Figure 3B:
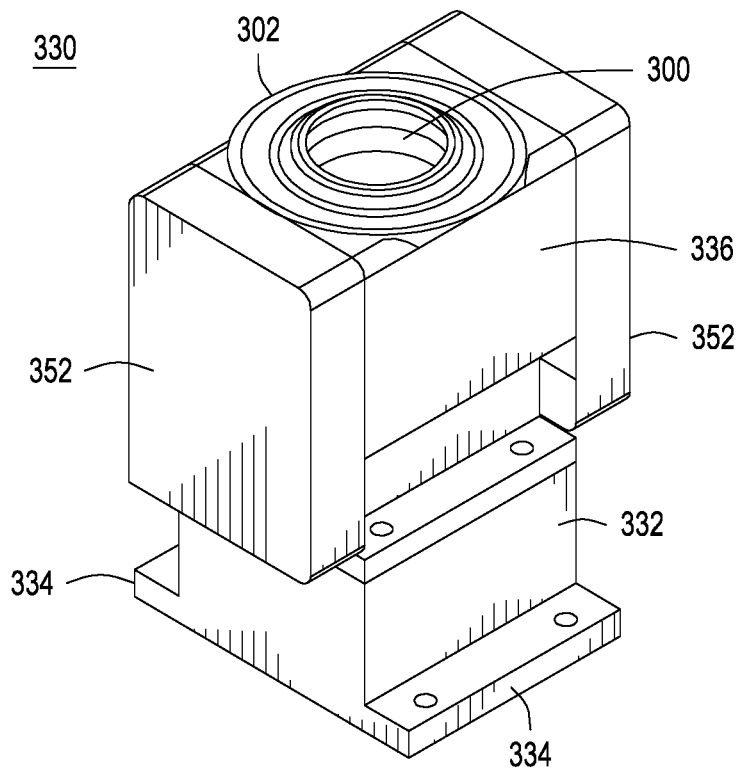
FIG. 3B illustrates a perspective view of one embodiment of a rotating growth vial in a cell growth module housing.
Figure 3C:
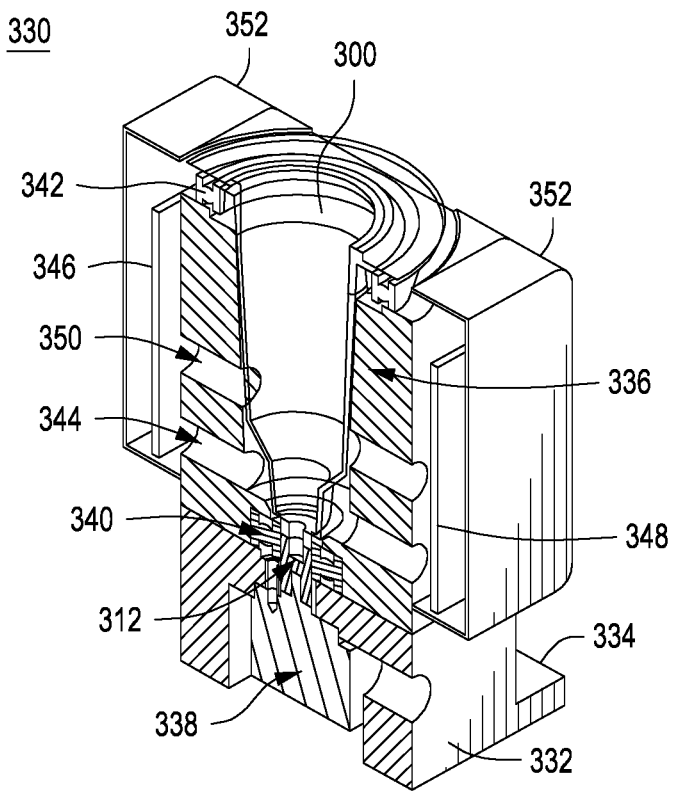
FIG. 3C depicts a cut-away view of the cell growth module from FIG. 3B.

FIG. 3B is a perspective view of one embodiment of a cell growth device 330. FIG. 3C depicts a cut-away view of the cell growth device 330 from FIG. 3B. In both figures, the rotating growth vial 300 is seen positioned inside a main housing 336 with the extended lip 302 of the rotating growth vial 300 extending above the main housing 336. Additionally, end housings 352, a lower housing 332 and flanges 334 are indicated in both figures. Flanges 334 are used to attach the cell growth device 330 to heating/cooling means or other structure (not shown). FIG. 3C depicts additional detail. In FIG. 3C, upper bearing 342 and lower bearing 340 are shown positioned within main housing 336. Upper bearing 342 and lower bearing 340 support the vertical load of rotating growth vial 300. Lower housing 332 contains the drive motor 338. The cell growth device 330 of FIG. 3C comprises two light paths: a primary light path 344, and a secondary light path 350. Light path 344 corresponds to light path 310 positioned in the constricted portion of the tapered-to-constricted portion of the rotating growth vial 300, and light path 350 corresponds to light path 308 in the tapered portion of the tapered-to-constricted portion of the rotating growth via 316. Light paths 310 and 308 are not shown in FIG. 3C but may be seen in FIG. 3A. In addition to light paths 344 and 350, there is an emission board 348 to illuminate the light path(s), and detector board 346 to detect the light after the light travels through the cell culture liquid in the rotating growth vial 300.

The motor 338 engages with drive mechanism 312 and is used to rotate the rotating growth vial 300. In some embodiments, motor 338 is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the motor 338 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 336, end housings 352 and lower housing 332 of the cell growth device 330 may be fabricated from any suitable, robust material including aluminum, stainless steel, and other thermally conductive materials, including plastics. These structures or portions thereof can be created through various techniques, e.g., metal fabrication, injection molding, creation of structural layers that are fused, etc. Whereas the rotating growth vial 300 is envisioned in some embodiments to be reusable, but preferably is consumable, the other components of the cell growth device 330 are preferably reusable and function as a stand-alone benchtop device or as a module in a multi-module cell processing system.

The processor (not shown) of the cell growth device 330 may be programmed with information to be used as a "blank" or control for the growing cell culture. A "blank" or control is a vessel containing cell growth medium only, which yields 100% transmittance and 0 OD, while the cell sample will deflect light rays and will have a lower percent transmittance and higher OD. As the cells grow in the media and become denser, transmittance will decrease and OD will increase. The processor (not shown) of the cell growth device 330—may be programmed to use wavelength values for blanks commensurate with the growth media typically used in cell culture (whether, e.g., mammalian cells, bacterial cells, animal cells, yeast cells, etc.). Alternatively, a second spectrophotometer and vessel may be included in the cell growth device 330, where the second spectrophotometer is used to read a blank at designated intervals.

Figure 3D:
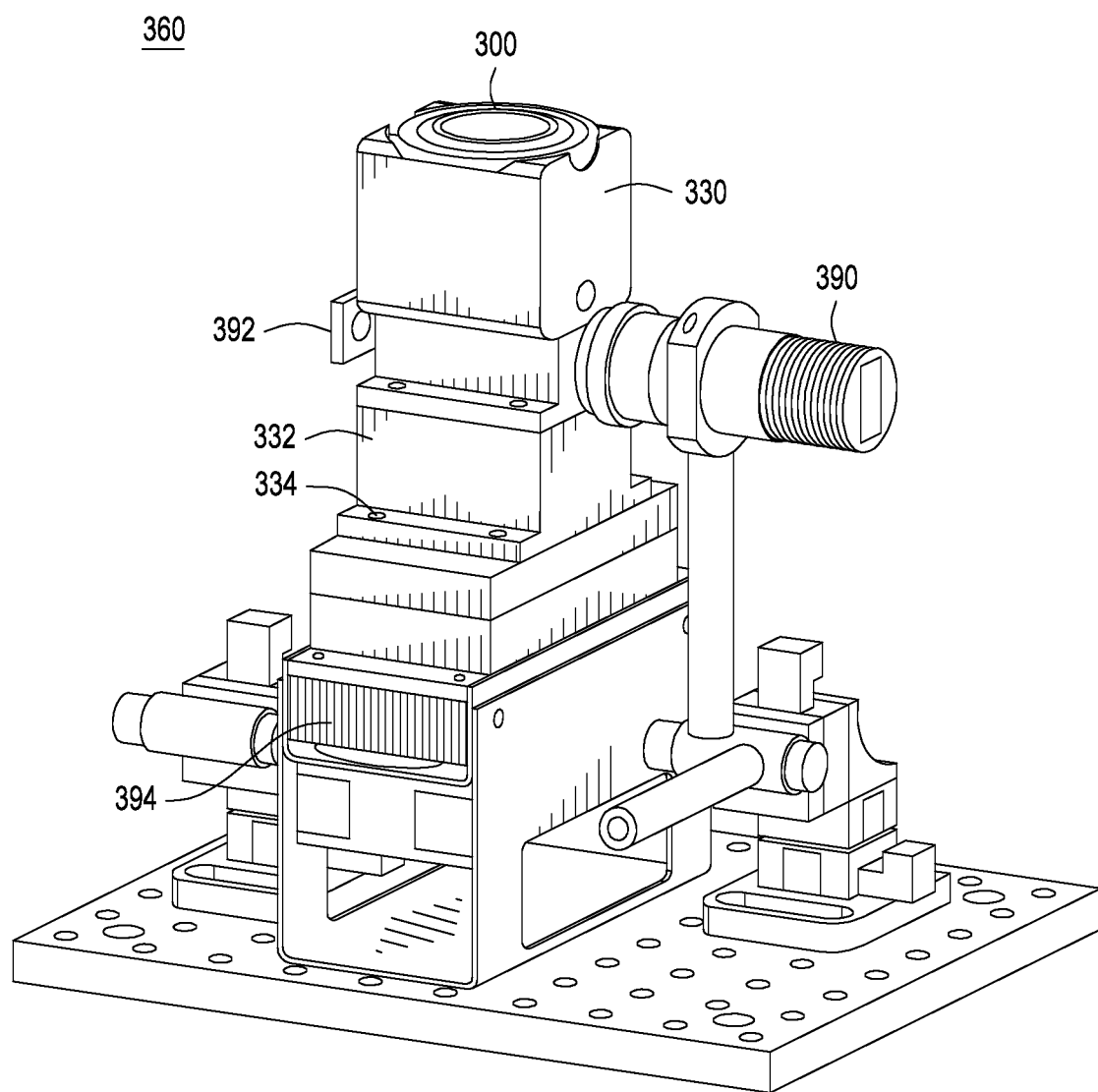
FIG. 3D illustrates the cell growth module of FIG. 3B coupled to LED, detector, and temperature regulating components.

FIG. 3D illustrates a cell growth device 330 as part of an assembly comprising the cell growth device 330 of FIG. 3B coupled to light source 390, detector 392, and thermal components 394. The rotating growth vial 300 is inserted into the cell growth device. Components of the light source 390 and detector 392 (e.g., such as a photodiode with gain control to cover 5-log) are coupled to the main housing of the cell growth device. The lower housing 332 that houses the motor that rotates the rotating growth vial 300 is illustrated, as is one of the flanges 334 that secures the cell growth device 330 to the assembly. Also, the thermal components 394 illustrated are a Peltier device or thermoelectric cooler. In this embodiment, thermal control is accomplished by attachment and electrical integration of the cell growth device 330 to the thermal components 394 via the flange 334 on the base of the lower housing 332. Thermoelectric coolers are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 300 is controlled to approximately +/−0.5° C.

In use, cells are inoculated (cells can be pipetted, e.g., from an automated liquid handling system or by a user) into pre-filled growth media of a rotating growth vial 300 by piercing though the foil seal or film. The programmed software of the cell growth device 330 sets the control temperature for growth, typically 30° C., then slowly starts the rotation of the rotating growth vial 300. The cell/growth media mixture slowly moves vertically up the wall due to centrifugal force allowing the rotating growth vial 300 to expose a large surface area of the mixture to a normal oxygen environment. The growth monitoring system takes either continuous readings of the OD or OD measurements at pre-set or pre-programmed time intervals. These measurements are stored in internal memory and if requested the software plots the measurements versus time to display a growth curve. If enhanced mixing is required, e.g., to optimize growth conditions, the speed of the vial rotation can be varied to cause an axial precession of the liquid, and/or a complete directional change can be performed at programmed intervals. The growth monitoring can be programmed to automatically terminate the growth stage at a pre-determined OD, and then quickly cool the mixture to a lower temperature to inhibit further growth.

One application for the cell growth device 330 is to constantly measure the optical density of a growing cell culture. One advantage of the described cell growth device is that optical density can be measured continuously (kinetic monitoring) or at specific time intervals; e.g., every 5, 10, 15, 20, 30, 45, or 60 seconds, or every 1, 2, 3, 4, 5, 6, 7, 8, 9, or 10 minutes. While the cell growth device 330 has been described in the context of measuring the optical density (OD) of a growing cell culture, it should, however, be understood by a skilled artisan given the teachings of the present specification that other cell growth parameters can be measured in addition to or instead of cell culture OD. As with optional measure of cell growth in relation to the solid wall device or module described supra, spectroscopy using visible, UV, or near infrared (NIR) light allows monitoring the concentration of nutrients and/or wastes in the cell culture and other spectroscopic measurements may be made; that is, other spectral properties can be measured via, e.g., dielectric impedance spectroscopy, visible fluorescence, fluorescence polarization, or luminescence. Additionally, the cell growth device 430 may include additional sensors for measuring, e.g., dissolved oxygen, carbon dioxide, pH, conductivity, and the like. For additional details regarding rotating growth vials and cell growth devices see U.S. Ser. No. 16/360,404, filed 21 Mar. 2019 and Ser. No. 16/360,423, filed 21 Mar. 2019.

The Cell Concentration Module

As described above in relation to the rotating growth vial and cell growth module, in order to obtain an adequate number of cells for transformation or transfection, cells typically are grown to a specific optical density in medium appropriate for the growth of the cells of interest; however, for effective transformation or transfection, it is desirable to decrease the volume of the cells as well as render the cells competent via buffer or medium exchange. Thus, one subcomponent or module that is desired in cell processing systems for the processes listed above is a module or component that can grow, perform buffer exchange, and/or concentrate cells and render them competent so that they may be transformed or transfected with the nucleic acids needed for engineering or editing the cell's genome.

Figure 4A:
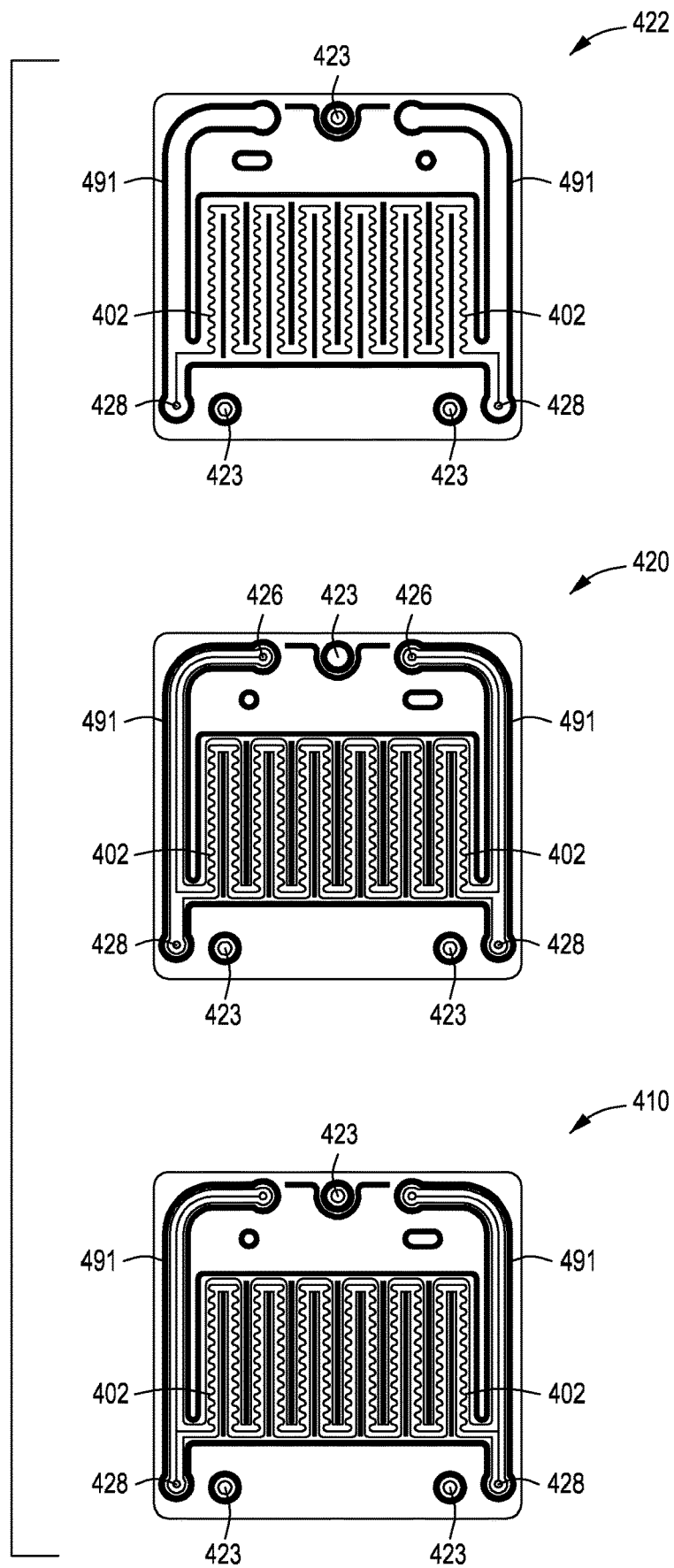
FIG. 4A depicts retentate (top) and permeate (bottom) members for use in a tangential flow filtration module (e.g., cell growth and/or concentration module), as well as the retentate and permeate members assembled into a tangential flow assembly (bottom).

FIG. 4A shows a retentate member 422 (top), permeate member 420 (middle) and a tangential flow assembly 410 (bottom) comprising the retentate member 422, membrane 424 (not seen in FIG. 4A), and permeate member 420 (also not seen). In FIG. 4A, retentate member 422 comprises a tangential flow channel 402, which has a serpentine configuration that initiates at one lower corner of retentate member 422—specifically at retentate port 428—traverses across and up then down and across retentate member 422, ending in the other lower corner of retentate member 422 at a second retentate port 428. Also seen on retentate member 422 are energy directors 491, which circumscribe the region where a membrane or filter (not seen in this FIG. 4A) is seated, as well as interdigitate between areas of channel 402. Energy directors 491 in this embodiment mate with and serve to facilitate ultrasonic welding or bonding of retentate member 422 with permeate/filtrate member 420 via the energy director component 491 on permeate/filtrate member 420 (at right). Additionally, countersinks 423 can be seen, two on the bottom one at the top middle of retentate member 422. Countersinks 423 are used to couple and tangential flow assembly 410 to a reservoir assembly (not seen in this FIG. 4A but see FIG. 4B).

Permeate/filtrate member 420 is seen in the middle of FIG. 4A and comprises, in addition to energy director 491, through-holes for retentate ports 428 at each bottom corner (which mate with the through-holes for retentate ports 428 at the bottom corners of retentate member 422), as well as a tangential flow channel 402 and two permeate/filtrate ports 426 positioned at the top and center of permeate member 420. The tangential flow channel 402 structure in this embodiment has a serpentine configuration and an undulating geometry, although other geometries may be used. Permeate member 420 also comprises countersinks 423, coincident with the countersinks 423 on retentate member 420.

On the left of FIG. 4A is a tangential flow assembly 410 comprising the retentate member 422 and permeate member 420 seen in this FIG. 4A. In this view, retentate member 422 is "on top" of the view, a membrane (not seen in this view of the assembly) would be adjacent and under retentate member 422 and permeate member 420 (also not seen in this view of the assembly) is adjacent to and beneath the membrane. Again countersinks 423 are seen, where the countersinks in the retentate member 422 and the permeate member 420 are coincident and configured to mate with threads or mating elements for the countersinks disposed on a reservoir assembly (not seen in FIG. 4A but see FIG. 4B).

A membrane or filter is disposed between the retentate and permeate members, where fluids can flow through the membrane but cells cannot and are thus retained in the flow channel disposed in the retentate member. Filters or membranes appropriate for use in the TFF device/module are those that are solvent resistant, are contamination free during filtration, and are able to retain the types and sizes of cells of interest. For example, in order to retain small cell types such as bacterial cells, pore sizes can be as low as 0.2 µm, however for other cell types, the pore sizes can be as high as 20 µm. Indeed, the pore sizes useful in the TFF device/module include filters with sizes from 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable non-reactive material including cellulose mixed ester (cellulose nitrate and acetate) (CME), polycarbonate (PC), polyvinylidene fluoride (PVDF), polyethersulfone (PES), polytetrafluoroethylene (PTFE), nylon, glass fiber, or metal substrates as in the case of laser or electrochemical etching.

The length of the channel structure 402 may vary depending on the volume of the cell culture to be grown and the optical density of the cell culture to be concentrated. The length of the channel structure typically is from 60 mm to 300 mm, or from 70 mm to 200 mm, or from 80 mm to 100 mm. The cross-section configuration of the flow channel 402 may be round, elliptical, oval, square, rectangular, trapezoidal, or irregular. If square, rectangular, or another shape with generally straight sides, the cross section may be from about 10 µm to 1000 µm wide, or from 200 µm to 800 µm wide, or from 300 µm to 700 µm wide, or from 400 µm to 600 µm wide; and from about 10 µm to 1000 µm high, or from 200 µm to 800 µm high, or from 300 µm to 700 µm high, or from 400 µm to 600 µm high. If the cross section of the flow channel 102 is generally round, oval or elliptical, the radius of the channel may be from about 50 µm to 1000 µm in hydraulic radius, or from 5 µm to 800 µm in hydraulic radius, or from 200 µm to 700 µm in hydraulic radius, or from 300 µm to 600 µm wide in hydraulic radius, or from about 200 to 500 µm in hydraulic radius. Moreover, the volume of the channel in the retentate 422 and permeate 420 members may be different depending on the depth of the channel in each member.

Figure 4B:
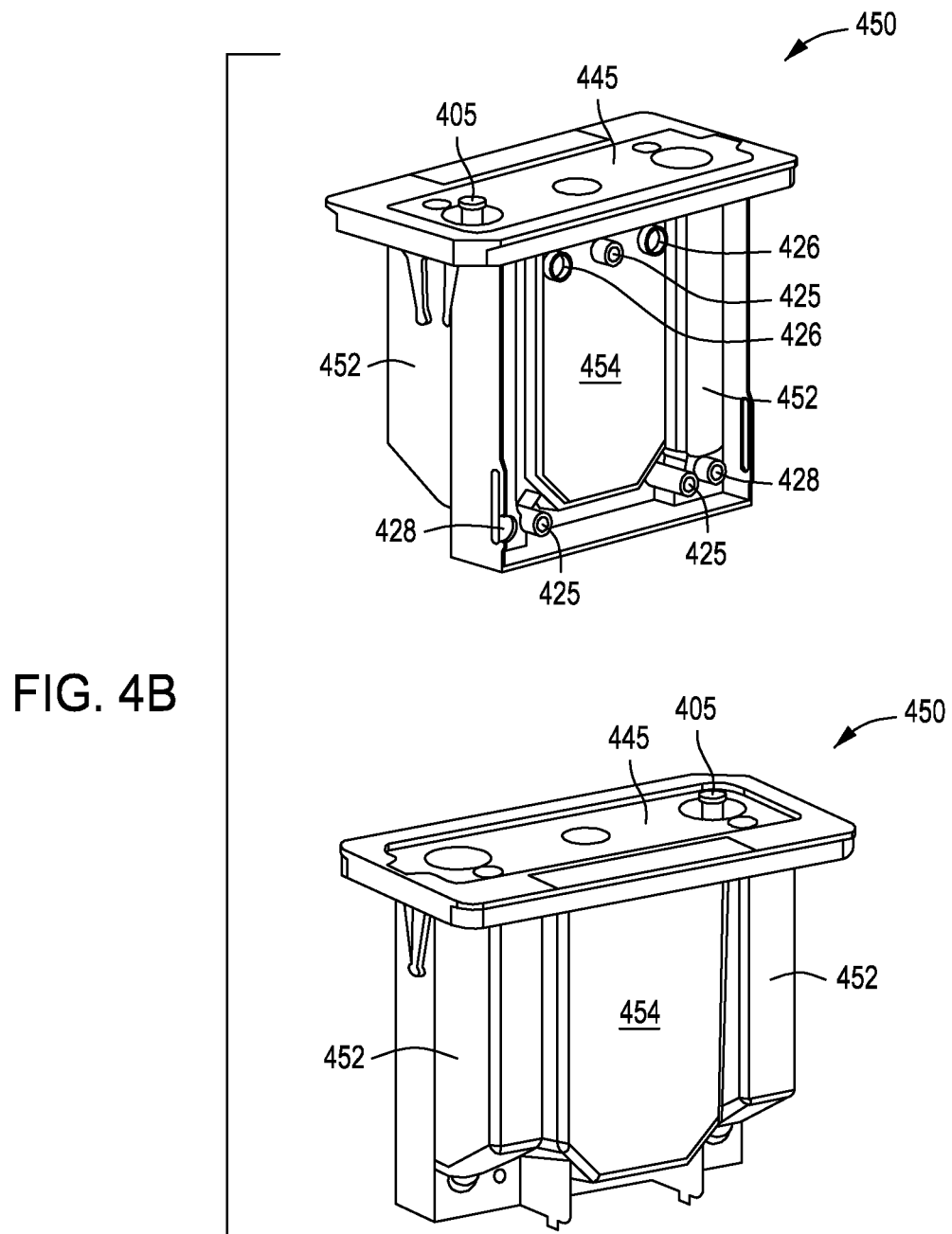
FIG. 4B depicts two side perspective views of a reservoir assembly of a tangential flow filtration module.

FIG. 4B shows front perspective (right) and rear perspective (left) views of a reservoir assembly 450 configured to be used with the tangential flow assembly 410 seen in FIG. 4A. Seen in the front perspective view (e.g., "front" being the side of reservoir assembly 450 that is coupled to the tangential flow assembly 410 seen in FIG. 4A) are retentate reservoirs 452 on either side of permeate reservoir 454. Also seen are permeate ports 426, retentate ports 428, and three threads or mating elements 425 for countersinks 423 (countersinks 423 not seen in this FIG. 4B). Threads or mating elements 425 for countersinks 423 are configured to mate or couple the tangential flow assembly 410 (seen in FIG. 4A) to reservoir assembly 450. Alternatively or in addition, fasteners, sonic welding or heat stakes may be used to mate or couple the tangential flow assembly 410 to reservoir assembly 450. In addition is seen gasket 445 covering the top of reservoir assembly 450. Gasket 445 is described in detail in relation to FIG. 4E. At left in FIG. 4B is a rear perspective view of reservoir assembly 450, where "rear" is the side of reservoir assembly 450 that is not coupled to the tangential flow assembly. Seen are retentate reservoirs 452, permeate reservoir 454, and gasket 445.

The TFF device may be fabricated from any robust material in which channels (and channel branches) may be milled including stainless steel, silicon, glass, aluminum, or plastics including cyclic-olefin copolymer (COC), cyclo-olefin polymer (COP), polystyrene, polyvinyl chloride, polyethylene, polyamide, polyethylene, polypropylene, acrylonitrile butadiene, polycarbonate, polyetheretherketone (PEEK), poly(methyl methylacrylate) (PMMA), polysulfone, and polyurethane, and co-polymers of these and other polymers. If the TFF device/module is disposable, preferably it is made of plastic. In some embodiments, the material used to fabricate the TFF device/module is thermally-conductive so that the cell culture may be heated or cooled to a desired temperature. In certain embodiments, the TFF device is formed by precision mechanical machining, laser machining, electro discharge machining (for metal devices); wet or dry etching (for silicon devices); dry or wet etching, powder or sandblasting, photostructuring (for glass devices); or thermoforming, injection molding, hot embossing, or laser machining (for plastic devices) using the materials mentioned above that are amenable to this mass production techniques.

Figure 4C:
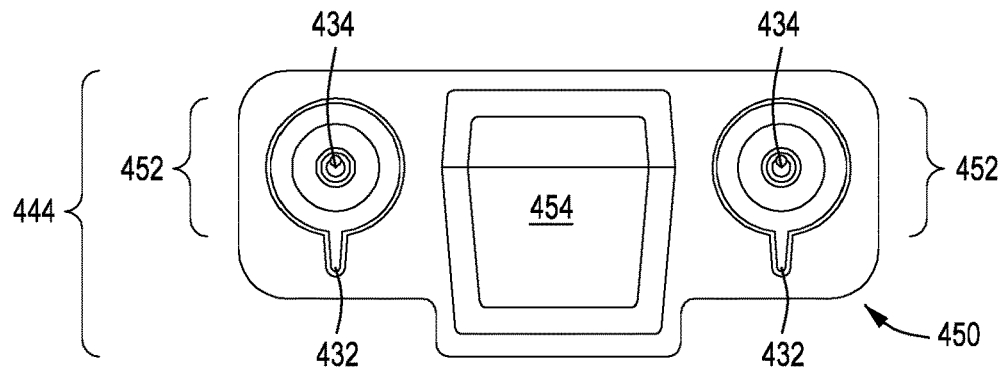
FIGS. 4C-4E depict an exemplary top, with fluidic and pneumatic ports and gasket suitable for the reservoir assemblies shown in FIG. 4B.
Figure 4D:
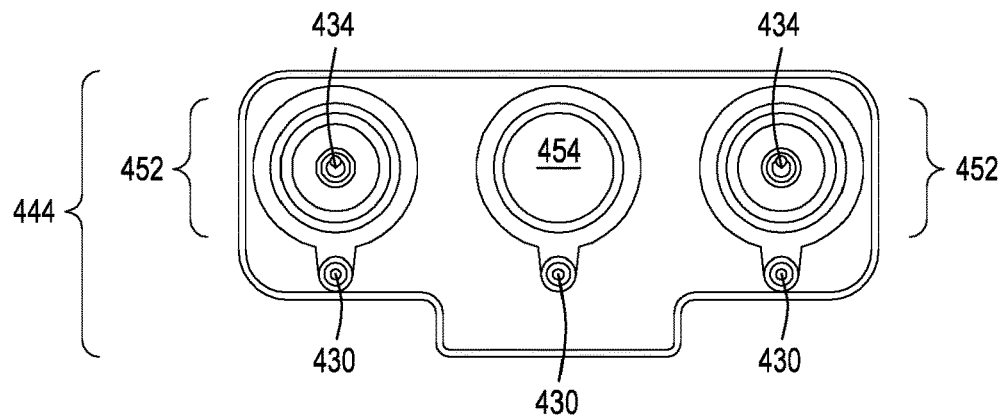
Figure 4E:
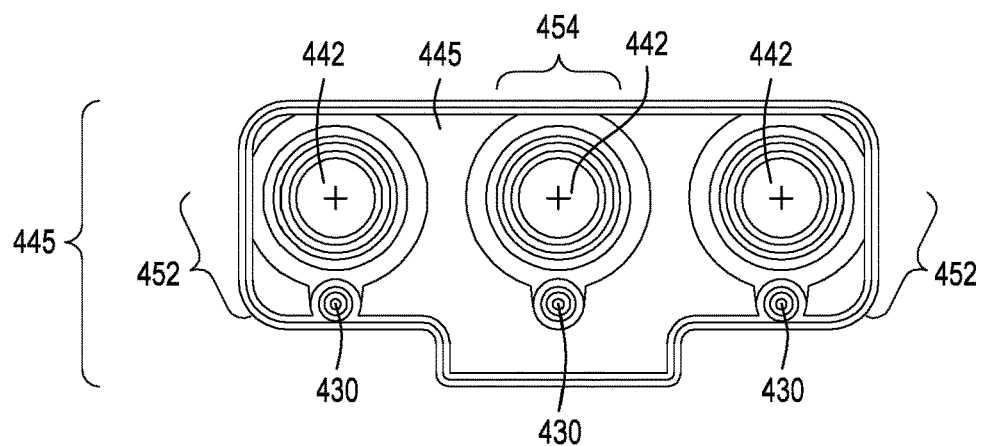

FIG. 4C depicts a top-down view of the reservoir assemblies 450 shown in FIG. 4B. FIG. 4D depicts a cover 444 for reservoir assembly 450 shown in FIGS. 4B and 4E depicts a gasket 445 that in operation is disposed on cover 444 of reservoir assemblies 450 shown in FIG. 4B. FIG. 4C is a top-down view of reservoir assembly 450, showing the tops of the two retentate reservoirs 452, one on either side of permeate reservoir 454. Also seen are grooves 432 that will mate with a pneumatic port (not shown), and fluid channels 434 that reside at the bottom of retentate reservoirs 452, which fluidically couple the retentate reservoirs 452 with the retentate ports 428 (not shown), via the through-holes for the retentate ports in permeate member 420 and membrane 424 (also not shown). FIG. 4D depicts a cover 444 that is configured to be disposed upon the top of reservoir assembly 450. Cover 444 has round cut-outs at the top of retentate reservoirs 452 and permeate/filtrate reservoir 454. Again at the bottom of retentate reservoirs 452 fluid channels 434 can be seen, where fluid channels 434 fluidically couple retentate reservoirs 452 with the retentate ports 428 (not shown). Also shown are three pneumatic ports 430 for each retentate reservoir 452 and permeate/filtrate reservoir 454. FIG. 4E depicts a gasket 445 that is configures to be disposed upon the cover 444 of reservoir assembly 450. Seen are three fluid transfer ports 442 for each retentate reservoir 452 and for permeate/filtrate reservoir 454. Again, three pneumatic ports 430, for each retentate reservoir 452 and for permeate/filtrate reservoir 454, are shown.

The overall work flow for cell growth comprises loading a cell culture to be grown into a first retentate reservoir, optionally bubbling air or an appropriate gas through the cell culture, passing or flowing the cell culture through the first retentate port then tangentially through the TFF channel structure while collecting medium or buffer through one or both of the permeate ports 406, collecting the cell culture through a second retentate port 404 into a second retentate reservoir, optionally adding additional or different medium to the cell culture and optionally bubbling air or gas through the cell culture, then repeating the process, all while measuring, e.g., the optical density of the cell culture in the retentate reservoirs continuously or at desired intervals. Measurements of optical densities (OD) at programmed time intervals are accomplished using a 600 nm Light Emitting Diode (LED) that has been columnated through an optic into the retentate reservoir(s) containing the growing cells. The light continues through a collection optic to the detection system which consists of a (digital) gain-controlled silicon photodiode. Generally, optical density is shown as the absolute value of the logarithm with base 10 of the power transmission factors of an optical attenuator: OD=−log 10 (Power out/Power in). Since OD is the measure of optical attenuation—that is, the sum of absorption, scattering, and reflection—the TFF device OD measurement records the overall power transmission, so as the cells grow and become denser in population, the OD (the loss of signal) increases. The OD system is pre-calibrated against OD standards with these values stored in an on-board memory accessible by the measurement program.

In the channel structure, the membrane bifurcating the flow channels retains the cells on one side of the membrane (the retentate side 422) and allows unwanted medium or buffer to flow across the membrane into a filtrate or permeate side (e.g., permeate member 420) of the device. Bubbling air or other appropriate gas through the cell culture both aerates and mixes the culture to enhance cell growth. During the process, medium that is removed during the flow through the channel structure is removed through the permeate/filtrate ports 406. Alternatively, cells can be grown in one reservoir with bubbling or agitation without passing the cells through the TFF channel from one reservoir to the other.

The overall work flow for cell concentration using the TFF device/module involves flowing a cell culture or cell sample tangentially through the channel structure. As with the cell growth process, the membrane bifurcating the flow channels retains the cells on one side of the membrane and allows unwanted medium or buffer to flow across the membrane into a permeate/filtrate side (e.g., permeate member 420) of the device. In this process, a fixed volume of cells in medium or buffer is driven through the device until the cell sample is collected into one of the retentate ports 404, and the medium/buffer that has passed through the membrane is collected through one or both of the permeate/filtrate ports 406. All types of prokaryotic and eukaryotic cells—both adherent and non-adherent cells—can be grown in the TFF device. Adherent cells may be grown on beads or other cell scaffolds suspended in medium that flow through the TFF device.

The medium or buffer used to suspend the cells in the cell concentration device/module may be any suitable medium or buffer for the type of cells being transformed or transfected, such as LB, SOC, TPD, YPG, YPAD, MEM, DMEM, IMDM, RPMI, Hanks', PBS and Ringer's solution, where the media may be provided in a reagent cartridge as part of a kit. For culture of adherent cells, cells may be disposed on beads, microcarriers, or other type of scaffold suspended in medium. Most normal mammalian tissue-derived cells—except those derived from the hematopoietic system—are anchorage dependent and need a surface or cell culture support for normal proliferation. In the rotating growth vial described herein, microcarrier technology is leveraged. Microcarriers of particular use typically have a diameter of 100-300 μm and have a density slightly greater than that of the culture medium (thus facilitating an easy separation of cells and medium for, e.g., medium exchange) yet the density must also be sufficiently low to allow complete suspension of the carriers at a minimum stirring rate in order to avoid hydrodynamic damage to the cells. Many different types of microcarriers are available, and different microcarriers are optimized for different types of cells. There are positively charged carriers, such as Cytodex 1 (dextran-based, GE Healthcare), DE-52 (cellulose-based, Sigma-Aldrich Labware), DE-53 (cellulose-based, Sigma-Aldrich Labware), and HLX 11-170 (polystyrene-based); collagen- or ECM—(extracellular matrix) coated carriers, such as Cytodex 3 (dextran-based, GE Healthcare) or HyQ-sphere Pro-F 102-4 (polystyrene-based, Thermo Scientific); non-charged carriers, like HyQ-sphere P 102-4 (Thermo Scientific); or macroporous carriers based on gelatin (Cultisphere, Percell Biolytica) or cellulose (Cytopore, GE Healthcare).

In both the cell growth and concentration processes, passing the cell sample through the TFF device and collecting the cells in one of the retentate ports 404 while collecting the medium in one of the permeate/filtrate ports 406 is considered "one pass" of the cell sample. The transfer between retentate reservoirs "flips" the culture. The retentate and permeatee ports collecting the cells and medium, respectively, for a given pass reside on the same end of TFF device/module with fluidic connections arranged so that there are two distinct flow layers for the retentate and permeate/filtrate sides, but if the retentate port 404 resides on the retentate member of device/module (that is, the cells are driven through the channel above the membrane and the filtrate (medium) passes to the portion of the channel below the membrane), the permeate/filtrate port 406 will reside on the permeate member of device/module and vice versa (that is, if the cell sample is driven through the channel below the membrane, the filtrate (medium) passes to the portion of the channel above the membrane). Due to the high pressures used to transfer the cell culture and fluids through the flow channel of the TFF device, the effect of gravity is negligible.

At the conclusion of a "pass" in either of the growth and concentration processes, the cell sample is collected by passing through the retentate port 404 and into the retentate reservoir (not shown). To initiate another "pass", the cell sample is passed again through the TFF device, this time in a flow direction that is reversed from the first pass. The cell sample is collected by passing through the retentate port 404 and into retentate reservoir (not shown) on the opposite end of the device/module from the retentate port 404 that was used to collect cells during the first pass. Likewise, the medium/buffer that passes through the membrane on the second pass is collected through the permeate port 406 on the opposite end of the device/module from the permeate port 406 that was used to collect the filtrate during the first pass, or through both ports. This alternating process of passing the retentate (the concentrated cell sample) through the device/module is repeated until the cells have been grown to a desired optical density, and/or concentrated to a desired volume, and both permeate ports (i.e., if there are more than one) can be open during the passes to reduce operating time. In addition, buffer exchange may be effected by adding a desired buffer (or fresh medium) to the cell sample in the retentate reservoir, before initiating another "pass", and repeating this process until the old medium or buffer is diluted and filtered out and the cells reside in fresh medium or buffer. Note that buffer exchange and cell growth may (and typically do) take place simultaneously, and buffer exchange and cell concentration may (and typically do) take place simultaneously. For further information and alternative embodiments on TFFs see, e.g., U.S. Ser. No. 62/728, 365, filed 7 Sep. 2018; 62/857,599, filed 5 Jun. 2019; and 62/867,415, filed 27 Jun. 2019.

The Cell Transformation Module

Figure 5C:
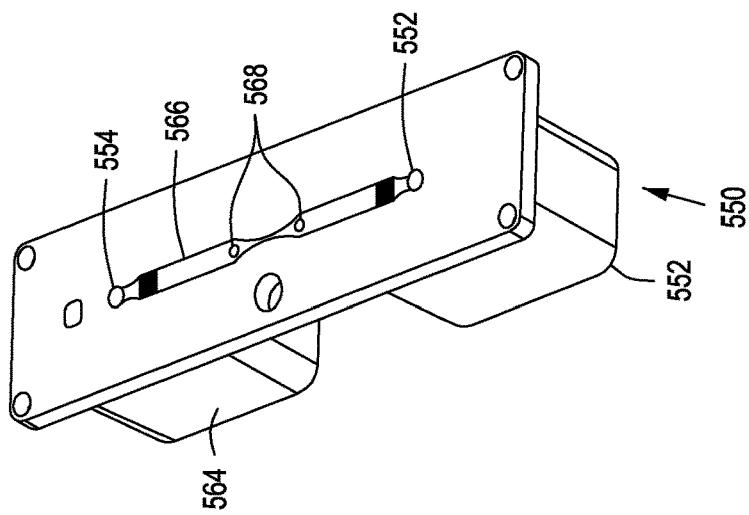
FIG. 5C depicts a bottom perspective view of one embodiment of an exemplary flow-through electroporation device that may be part of a reagent cartridge.
Figure 5B:
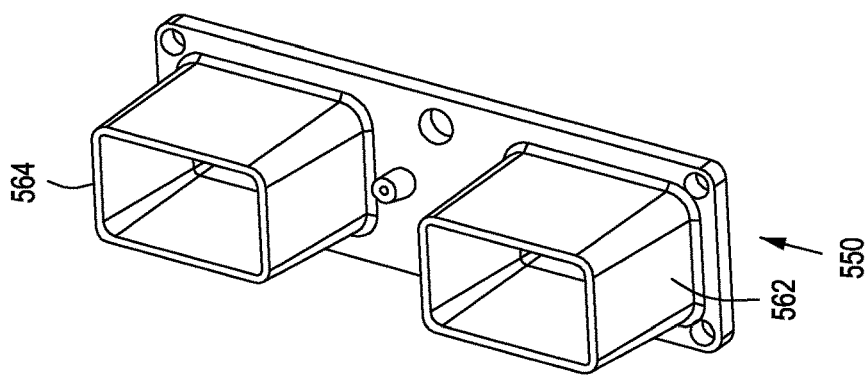
FIG. 5B is a top perspective view of one embodiment of an exemplary flow-through electroporation device that may be part of a reagent cartridge.
Figure 5A:
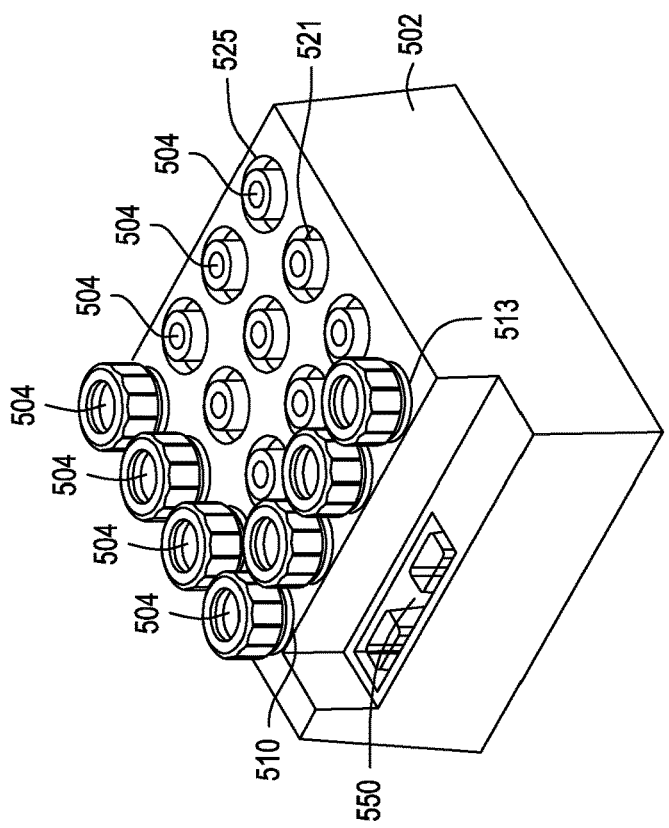
FIG. 5A depicts an exemplary combination reagent cartridge and electroporation device (e.g., transformation module) that may be used in a multi-module cell processing instrument.

FIG. 5A depicts an exemplary combination reagent cartridge and electroporation device 500 ("cartridge") that may be used in an automated multi-module cell processing instrument along with the TFF module. In addition, in certain embodiments the material used to fabricate the cartridge is thermally-conductive, as in certain embodiments the cartridge 500 contacts a thermal device (not shown), such as a Peltier device or thermoelectric cooler, that heats or cools reagents in the reagent reservoirs or reservoirs 504. Reagent reservoirs or reservoirs 504 may be reservoirs into which individual tubes of reagents are inserted as shown in FIG. 5A, or the reagent reservoirs may hold the reagents without inserted tubes. Additionally, the reservoirs in a reagent cartridge may be configured for any combination of tubes, co-joined tubes, and direct-fill of reagents.

In one embodiment, the reagent reservoirs or reservoirs 504 of reagent cartridge 500 are configured to hold various size tubes, including, e.g., 250 ml tubes, 25 ml tubes, 10 ml tubes, 5 ml tubes, and Eppendorf or microcentrifuge tubes. In yet another embodiment, all reservoirs may be configured to hold the same size tube, e.g., 5 ml tubes, and reservoir inserts may be used to accommodate smaller tubes in the reagent reservoir. In yet another embodiment—particularly in an embodiment where the reagent cartridge is disposable—the reagent reservoirs hold reagents without inserted tubes. In this disposable embodiment, the reagent cartridge may be part of a kit, where the reagent cartridge is pre-filled with reagents and the receptacles or reservoirs sealed with, e.g., foil, heat seal acrylic or the like and presented to a consumer where the reagent cartridge can then be used in an automated multi-module cell processing instrument. As one of ordinary skill in the art will appreciate given the present disclosure, the reagents contained in the reagent cartridge will vary depending on work flow; that is, the reagents will vary depending on the processes to which the cells are subjected in the automated multi-module cell processing instrument, e.g., protein production, cell transformation and culture, cell editing, etc.

Reagents such as cell samples, enzymes, buffers, nucleic acid vectors, expression cassettes, proteins or peptides, reaction components (such as, e.g., $MgCl_2$, dNTPs, nucleic acid assembly reagents, gap repair reagents, and the like), wash solutions, ethanol, and magnetic beads for nucleic acid purification and isolation, etc. may be positioned in the reagent cartridge at a known position. In some embodiments of cartridge 500, the cartridge comprises a script (not shown) readable by a processor (not shown) for dispensing the reagents. Also, the cartridge 500 as one component in an automated multi-module cell processing instrument may comprise a script specifying two, three, four, five, ten or more processes to be performed by the automated multi-module cell processing instrument. In certain embodiments, the reagent cartridge is disposable and is pre-packaged with reagents tailored to performing specific cell processing protocols, e.g., genome editing or protein production. Because the reagent cartridge contents vary while components/modules of the automated multi-module cell processing instrument or system may not, the script associated with a particular reagent cartridge matches the reagents used and cell processes performed. Thus, e.g., reagent cartridges may be pre-packaged with reagents for genome editing and a script that specifies the process steps for performing genome editing in an automated multi-module cell processing instrument, or, e.g., reagents for protein expression and a script that specifies the process steps for performing protein expression in an automated multi-module cell processing instrument.

For example, the reagent cartridge may comprise a script to pipette competent cells from a reservoir, transfer the cells to a transformation module, pipette a nucleic acid solution comprising a vector with expression cassette from another reservoir in the reagent cartridge, transfer the nucleic acid solution to the transformation module, initiate the transformation process for a specified time, then move the transformed cells to yet another reservoir in the reagent cassette or to another module such as a cell growth module in the automated multi-module cell processing instrument. In another example, the reagent cartridge may comprise a script to transfer a nucleic acid solution comprising a vector from a reservoir in the reagent cassette, nucleic acid solution comprising editing oligonucleotide cassettes in a reservoir in the reagent cassette, and a nucleic acid assembly mix from another reservoir to the nucleic acid assembly/desalting module, if present. The script may also specify process steps performed by other modules in the automated multi-module cell processing instrument. For example, the script may specify that the nucleic acid assembly/desalting reservoir be heated to 50° C. for 30 min to generate an assembled product; and desalting and resuspension of the assembled product via magnetic bead-based nucleic acid purification involving a series of pipette transfers and mixing of magnetic beads, ethanol wash, and buffer.

As described in relation to FIGS. 5B and 5C below, the exemplary reagent cartridges for use in the automated multi-module cell processing instruments may include one or more electroporation devices, preferably flow-through electroporation (FTEP) devices. In yet other embodiments, the reagent cartridge is separate from the transformation module. Electroporation is a widely-used method for permeabilization of cell membranes that works by temporarily generating pores in the cell membranes with electrical stimulation. Applications of electroporation include the delivery of DNA, RNA, siRNA, peptides, proteins, antibodies, drugs or other substances to a variety of cells such as mammalian cells (including human cells), plant cells, archea, yeasts, other eukaryotic cells, bacteria, and other cell types. Electrical stimulation may also be used for cell fusion in the production of hybridomas or other fused cells. During a typical electroporation procedure, cells are suspended in a buffer or medium that is favorable for cell survival. For bacterial cell electroporation, low conductance mediums, such as water, glycerol solutions and the like, are often used to reduce the heat production by transient high current. In traditional electroporation devices, the cells and material to be electroporated into the cells (collectively "the cell sample") are placed in a cuvette embedded with two flat electrodes for electrical discharge. For example, Bio-Rad (Hercules, Calif.) makes the GENE PULSER XCELL™ line of products to electroporate cells in cuvettes. Traditionally, electroporation requires high field strength; however, the flow-through electroporation devices included in the reagent cartridges achieve high efficiency cell electroporation with low toxicity. The reagent cartridges of the disclosure allow for particularly easy integration with robotic liquid handling instrumentation that is typically used in automated instruments and systems such as air displacement pipettors. Such automated instrumentation includes, but is not limited to, off-the-shelf automated liquid handling systems from Tecan (Mannedorf, Switzerland), Hamilton (Reno, Nev.), Beckman Coulter (Fort Collins, Colo.), etc.

FIGS. 5B and 5C are top perspective and bottom perspective views, respectively, of an exemplary FTEP device 550 that may be part of (e.g., a component in) reagent cartridge 500 in FIG. 5A or may be a stand-alone module; that is, not a part of a reagent cartridge or other module. FIG. 5B depicts an FTEP device 550. The FTEP device 550 has wells that define cell sample inlets 552 and cell sample outlets 554. FIG. 5C is a bottom perspective view of the FTEP device 550 of FIG. 5B. An inlet well 552 and an outlet well 554 can be seen in this view. Also seen in FIG. 5C are the bottom of an inlet 562 corresponding to well 552, the bottom of an outlet 564 corresponding to the outlet well 554, the bottom of a defined flow channel 566 and the bottom of two electrodes 568 on either side of flow channel 566. The FTEP devices may comprise push-pull pneumatic means to allow multi-pass electroporation procedures; that is, cells to electroporated may be "pulled" from the inlet toward the outlet for one pass of electroporation, then be "pushed" from the outlet end of the FTEP device toward the inlet end to pass between the electrodes again for another pass of electroporation. Further, this process may be repeated one to many times. For additional information regarding FTEP devices, see, e.g., U.S. Ser. No. 16/147,120, filed 28 Sep. 2018; Ser. No. 16/147,353, filed 28 Sep. 2018; Ser. No. 16/426,310, filed 30 May 2019; and Ser. No. 16/147,871, filed 30 Sep. 2018; and U.S. Pat. No. 10,323,258, issued 18 Jun. 2019. Further, other embodiments of the reagent cartridge may provide or accommodate electroporation devices that are not configured as FTEP devices, such as those described in U.S. Ser. No. 16/109,156, filed 22 Aug. 2018. For reagent cartridges useful in the present automated multi-module cell processing instruments, see, e.g., U.S. Pat. No. 10,376,889, issued 13 Aug. 2019; and U.S. Ser. No. 16/451,601, filed 25 Jun. 2019.

Figure 5D:
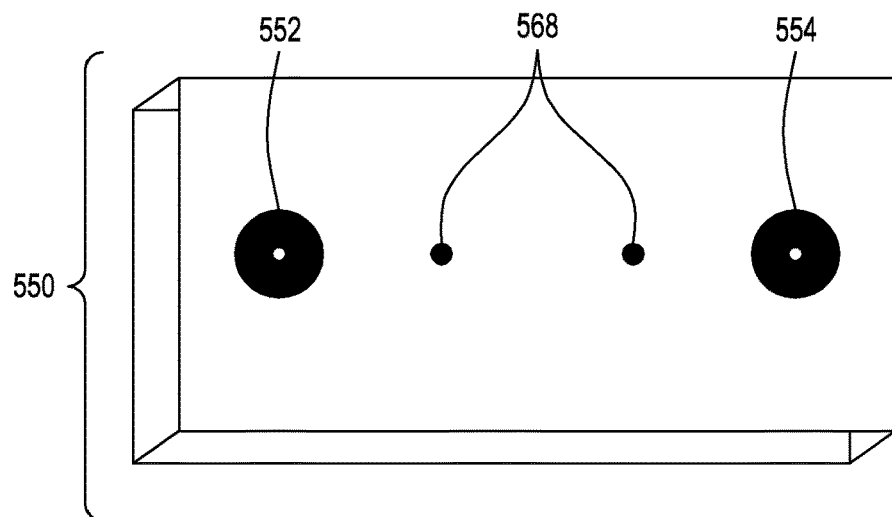
FIGS. 5D-5F depict a top perspective view, a top view of a cross section, and a side perspective view of a cross section of an FTEP device useful in a multi-module automated cell processing instrument such as that shown in FIGS. 2A-2C.
Figure 5E:
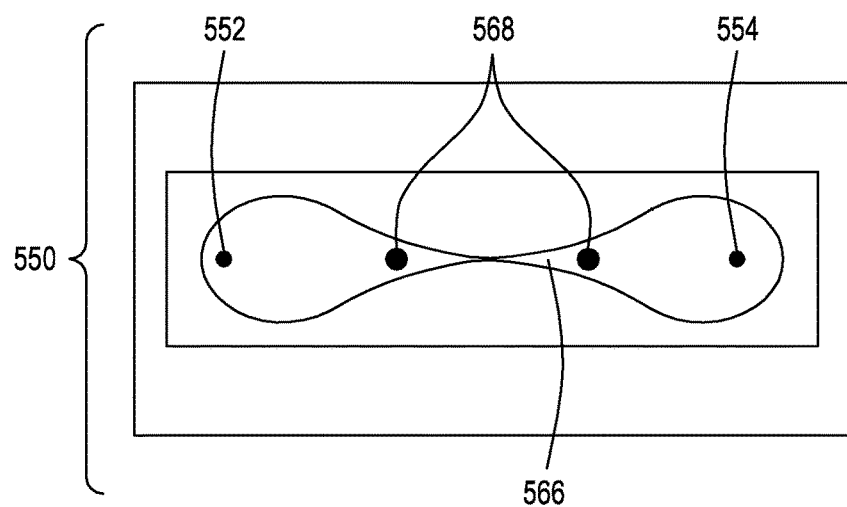
Figure 5F:
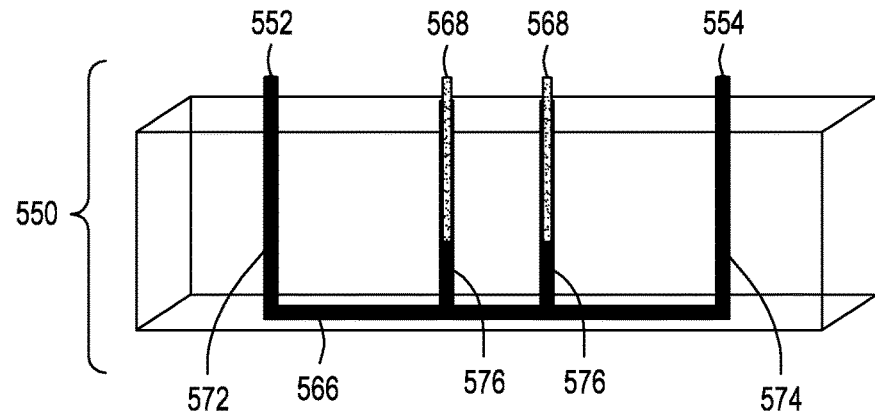

Additional details of the FTEP devices are illustrated in FIGS. 5D-5F. Note that in the FTEP devices in FIGS. 5D-5F the electrodes are placed such that a first electrode is placed between an inlet and a narrowed region of the flow channel, and the second electrode is placed between the narrowed region of the flow channel and an outlet. FIG. 5D shows a top planar view of an FTEP device 550 having an inlet 552 for introducing a fluid containing cells and exogenous material into FTEP device 550 and an outlet 554 for removing the transformed cells from the FTEP following electroporation. The electrodes 568 are introduced through channels (not shown) in the device. FIG. 5E shows a cutaway view from the top of the FTEP device 550, with the inlet 552, outlet 554, and electrodes 568 positioned with respect to a flow channel 566. FIG. 5F shows a side cutaway view of FTEP device 550 with the inlet 552 and inlet channel 572, and outlet 554 and outlet channel 574. The electrodes 568 are positioned in electrode channels 576 so that they are in fluid communication with the flow channel 566, but not directly in the path of the cells traveling through the flow channel 566. Note that the first electrode is placed between the inlet and the narrowed region of the flow channel, and the second electrode is placed between the narrowed region of the flow channel and the outlet. The electrodes 568 in this aspect of the device are positioned in the electrode channels 576 which are generally perpendicular to the flow channel 566 such that the fluid containing the cells and exogenous material flows from the inlet channel 572 through the flow channel 566 to the outlet channel 574, and in the process fluid flows into the electrode channels 376 to be in contact with the electrodes 568. In this aspect, the inlet channel, outlet channel and electrode channels all originate from the same planar side of the device. In certain aspects, however, the electrodes may be introduced from a different planar side of the FTEP device than the inlet and outlet channels.

In the FTEP devices of the disclosure, the toxicity level of the transformation results in greater than 30% viable cells after electroporation, preferably greater than 35%, 40%, 45%, 50%, 55%, 60%, 70%, 75%, 80%, 85%, 90%, 95% or even 99% viable cells following transformation, depending on the cell type and the nucleic acids being introduced into the cells.

The housing of the FTEP device can be made from many materials depending on whether the FTEP device is to be reused, autoclaved, or is disposable, including stainless steel, silicon, glass, resin, polyvinyl chloride, polyethylene, polyamide, polystyrene, polyethylene, polypropylene, acrylonitrile butadiene, polycarbonate, polyetheretherketone (PEEK), polysulfone and polyurethane, co-polymers of these and other polymers. Similarly, the walls of the channels in the device can be made of any suitable material including silicone, resin, glass, glass fiber, polyvinyl chloride, polyethylene, polyamide, polyethylene, polypropylene, acrylonitrile butadiene, polycarbonate, polyetheretherketone (PEEK), polysulfone and polyurethane, co-polymers of these and other polymers. Preferred materials include crystal styrene, cyclo-olefin polymer (COP) and cyclic olephin co-polymers (COC), which allow the device to be formed entirely by injection molding in one piece with the exception of the electrodes and, e.g., a bottom sealing film if present.

The FTEP devices described herein (or portions of the FTEP devices) can be created or fabricated via various techniques, e.g., as entire devices or by creation of structural layers that are fused or otherwise coupled. For example, for metal FTEP devices, fabrication may include precision mechanical machining or laser machining; for silicon FTEP devices, fabrication may include dry or wet etching; for glass FTEP devices, fabrication may include dry or wet etching, powderblasting, sandblasting, or photostructuring; and for plastic FTEP devices fabrication may include thermoforming, injection molding, hot embossing, or laser machining. The components of the FTEP devices may be manufactured separately and then assembled, or certain components of the FTEP devices (or even the entire FTEP device except for the electrodes) may be manufactured (e.g., using 3D printing) or molded (e.g., using injection molding) as a single entity, with other components added after molding. For example, housing and channels may be manufactured or molded as a single entity, with the electrodes later added to form the FTEP unit. Alternatively, the FTEP device may also be formed in two or more parallel layers, e.g., a layer with the horizontal channel and filter, a layer with the vertical channels, and a layer with the inlet and outlet ports, which are manufactured and/or molded individually and assembled following manufacture.

In specific aspects, the FTEP device can be manufactured using a circuit board as a base, with the electrodes, filter and/or the flow channel formed in the desired configuration on the circuit board, and the remaining housing of the device containing, e.g., the one or more inlet and outlet channels and/or the flow channel formed as a separate layer that is then sealed onto the circuit board. The sealing of the top of the housing onto the circuit board provides the desired configuration of the different elements of the FTEP devices of the disclosure. Also, two to many FTEP devices may be manufactured on a single substrate, then separated from one another thereafter or used in parallel. In certain embodiments, the FTEP devices are reusable and, in some embodiments, the FTEP devices are disposable. In additional embodiments, the FTEP devices may be autoclavable.

The electrodes 408 can be formed from any suitable metal, such as copper, stainless steel, titanium, aluminum, brass, silver, rhodium, gold or platinum, or graphite. One preferred electrode material is alloy 303 (UNS330300) austenitic stainless steel. An applied electric field can destroy electrodes made from of metals like aluminum. If a multiple-use (i.e., non-disposable) flow-through FTEP device is desired—as opposed to a disposable, one-use flow-through FTEP device—the electrode plates can be coated with metals resistant to electrochemical corrosion. Conductive coatings like noble metals, e.g., gold, can be used to protect the electrode plates.

As mentioned, the FTEP devices may comprise push-pull pneumatic means to allow multi-pass electroporation procedures; that is, cells to electroporated may be "pulled" from the inlet toward the outlet for one pass of electroporation, then be "pushed" from the outlet end of the flow-through FTEP device toward the inlet end to pass between the electrodes again for another pass of electroporation. This process may be repeated one to many times.

Depending on the type of cells to be electroporated (e.g., bacterial, yeast, mammalian) and the configuration of the electrodes, the distance between the electrodes in the flow channel can vary widely. For example, where the flow channel decreases in width, the flow channel may narrow to between 10 µm and 5 mm, or between 25 µm and 3 mm, or between 50 µm and 2 mm, or between 75 µm and 1 mm. The distance between the electrodes in the flow channel may be between 1 mm and 10 mm, or between 2 mm and 8 mm, or between 3 mm and 7 mm, or between 4 mm and 6 mm. The overall size of the FTEP device may be from 3 cm to 15 cm in length, or 4 cm to 12 cm in length, or 4.5 cm to 10 cm in length. The overall width of the FTEP device may be from 0.5 cm to 5 cm, or from 0.75 cm to 3 cm, or from 1 cm to 2.5 cm, or from 1 cm to 1.5 cm.

The region of the flow channel that is narrowed is wide enough so that at least two cells can fit in the narrowed portion side-by-side. For example, a typical bacterial cell is 1 µm in diameter; thus, the narrowed portion of the flow channel of the FTEP device used to transform such bacterial cells will be at least 2 µm wide. In another example, if a mammalian cell is approximately 50 µm in diameter, the narrowed portion of the flow channel of the FTEP device used to transform such mammalian cells will be at least 100 µm wide. That is, the narrowed portion of the FTEP device will not physically contort or "squeeze" the cells being transformed.

In embodiments of the FTEP device where reservoirs are used to introduce cells and exogenous material into the FTEP device, the reservoirs range in volume from 100 µL to 10 mL, or from 500 µL to 75 mL, or from 1 mL to 5 mL. The flow rate in the FTEP ranges from 0.1 mL to 5 mL per minute, or from 0.5 mL to 3 mL per minute, or from 1.0 mL to 2.5 mL per minute. The pressure in the FTEP device ranges from 1-30 psi, or from 2-10 psi, or from 3-5 psi.

To avoid different field intensities between the electrodes, the electrodes should be arranged in parallel. Furthermore, the surface of the electrodes should be as smooth as possible without pin holes or peaks. Electrodes having a roughness Rz of 1 to 10 µm are preferred. In another embodiment of the invention, the flow-through electroporation device comprises at least one additional electrode which applies a ground potential to the FTEP device. Flow-through electroporation devices (either as a stand-alone instrument or as a module in an automated multi-module system) are described in, e.g., U.S. Ser. No. 16/147,120, filed 28 Sep. 2018; Ser. No. 16/147,353, filed 28 Sep. 2018; Ser. No. 16/147,865, filed 30 Sep. 2018; and Ser. No. 16/426,310, filed 30 May 2019; and U.S. Pat. No. 10,323,258, issued 18 Jun. 2019.

Cell Singulation and Enrichment Device

Figure 6A:
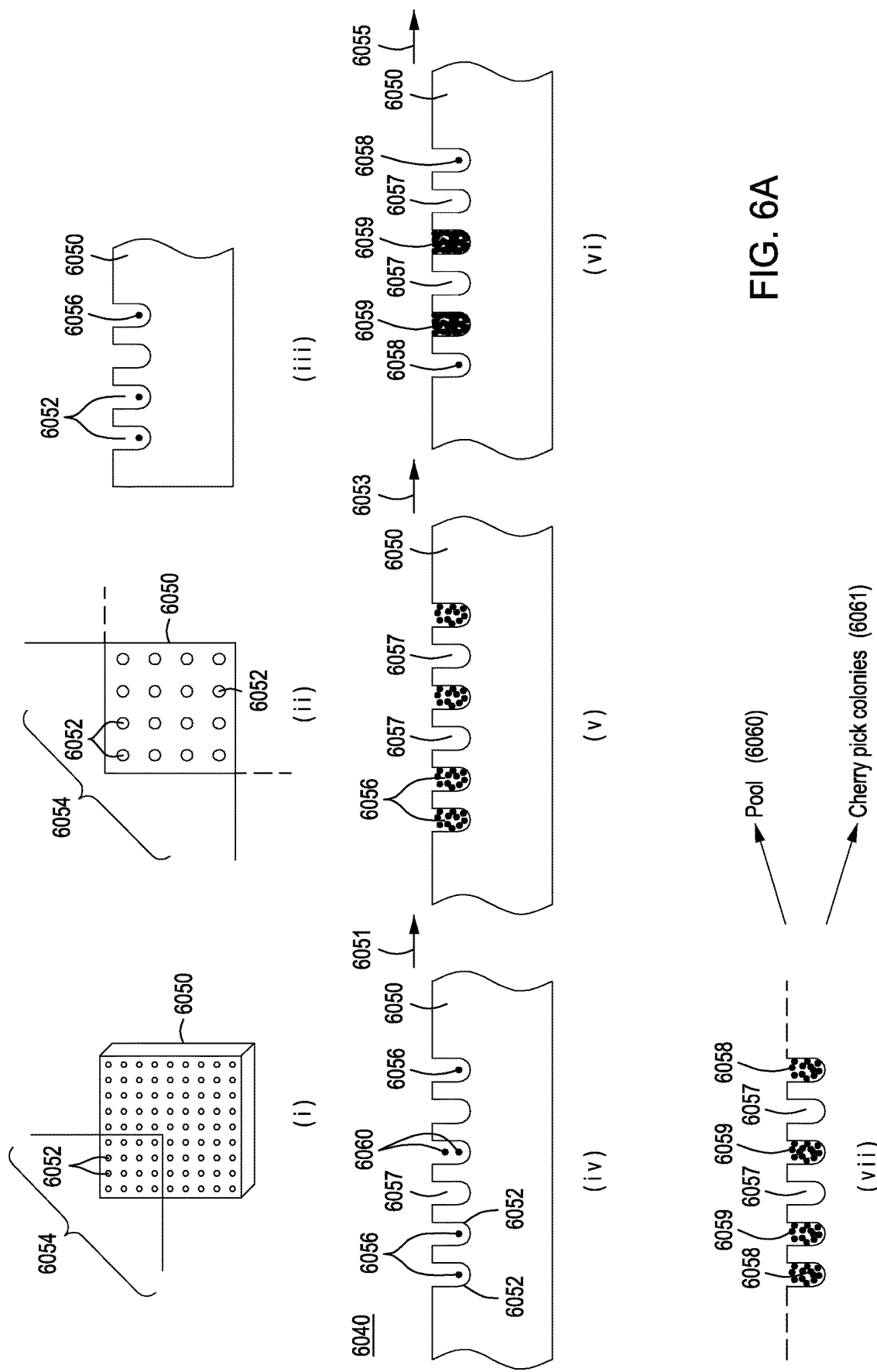
FIG. 6A depicts a simplified graphic of a workflow for singulating, editing and normalizing cells in a solid wall device. 6B depicts a simplified graphic of a workflow variation for substantially singulating, editing and normalizing cells in a solid wall device.

FIG. 6A depicts a solid wall device 6050 and a workflow for singulating cells in microwells in the solid wall device. At the top left of the figure (i), there is depicted solid wall device 6050 with microwells 6052. A section 6054 of substrate 6050 is shown at (ii), also depicting microwells 6052. At (iii), a side cross-section of solid wall device 6050 is shown, and microwells 6052 have been loaded, where, in this embodiment, Poisson or substantial Poisson loading has taken place; that is, each microwell has one or no cells, and the likelihood that any one microwell has more than one cell is low. At (iv), workflow 6040 is illustrated where substrate 6050 having microwells 6052 shows microwells 6056 with one cell per microwell, microwells 6057 with no cells in the microwells, and one microwell 6060 with two cells in the microwell. In step 6051, the cells in the microwells are allowed to double approximately 2-150 times to form clonal colonies (v), then editing is allowed to occur 6053.

After editing 6053, many cells in the colonies of cells that have been edited die as a result of the double-strand cuts caused by active editing and there is a lag in growth for the edited cells that do survive but must repair and recover following editing (microwells 6058), where cells that do not undergo editing thrive (microwells 6059) (vi). All cells are allowed to continue grow to establish colonies and normalize, where the colonies of edited cells in microwells 6058 catch up in size and/or cell number with the cells in microwells 6059 that do not undergo editing (vii). Once the cell colonies are normalized, either pooling 6060 of all cells in the microwells can take place, in which case the cells are enriched for edited cells by eliminating the bias from non-editing cells and fitness effects from editing; alternatively, colony growth in the microwells is monitored after editing, and slow growing colonies (e.g., the cells in microwells 6058) are identified and selected 6061 (e.g., "cherry picked") resulting in even greater enrichment of edited cells.

In growing the cells, the medium used will depend, of course, on the type of cells being edited—e.g., bacterial, yeast or mammalian. For example, medium for yeast cell growth includes LB, SOC, TPD, YPG, YPAD, MEM and DMEM.

Figure 6B:
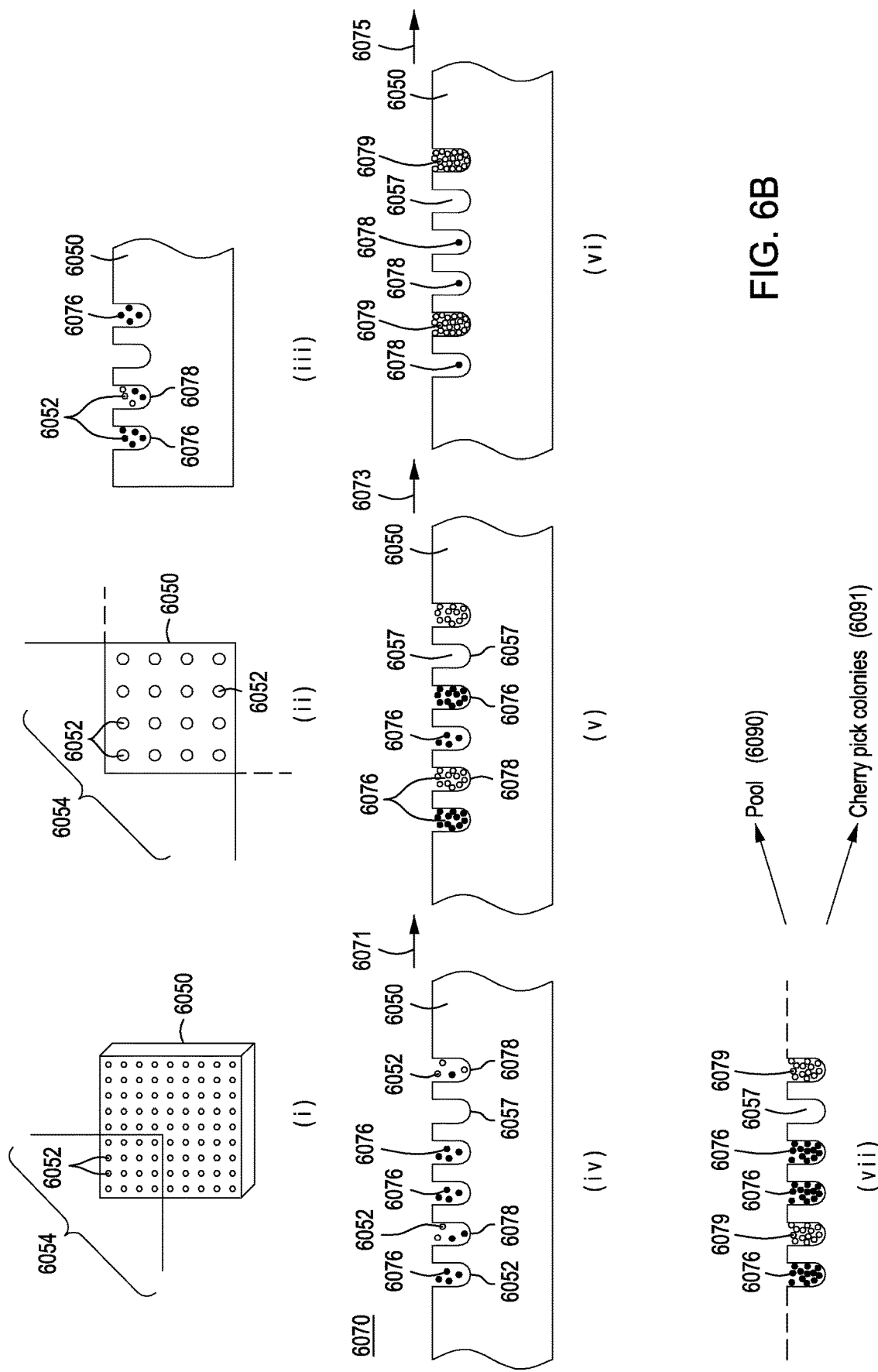
FIGS. 6C-6E depict an embodiment of a solid wall isolation incubation and normalization (SWIIN) module.
FIG. 6F depicts the embodiment of the SWIIN module in FIGS. 6C-6E further comprising a heater and a heated cover.

FIG. 6B depicts a solid wall device 6050 and a workflow for substantially singulating cells in microwells in a solid wall device. At the top left of the figure (i), there is depicted solid wall device 350 with microwells 6052. A section 6054 of substrate 6050 is shown at (ii), also depicting microwells 6052. At (iii), a side cross-section of solid wall device 6050 is shown, and microwells 6052 have been loaded, where, in this embodiment, substantial Poisson loading has taken place; that is, some microwells 6057 have no cells, and some microwells 6076, 6078 have a few cells. In FIG. 6B, cells with active gRNAs are shown as solid circles, and cells with inactive gRNAs are shown as open circles. At (iv), workflow 6070 is illustrated where substrate 6050 having microwells 6052 shows three microwells 6076 with several cells all with active gRNAs, microwell 6057 with no cells, and two microwells 6078 with some cells having active gRNAs and some cells having inactive gRNAs. In step 6071, the cells in the microwells are allowed to double approximately 2-150 times to form clonal colonies (v), then editing takes place 6073.

After editing 6073, many cells in the colonies of cells that have been edited die as a result of the double-strand cuts caused by active editing and there is a lag in growth for the edited cells that do survive but must repair and recover following editing (microwells 6076), where cells that do not undergo editing thrive (microwells 6078) (vi). Thus, in microwells 6076 where only cells with active gRNAs reside (cells depicted by solid circles), most cells die off; however, in microwells 6078 containing cells with inactive gRNAs (cells depicted by open circles), cells continue to grow and are not impacted by active editing. The cells in each microwell (6076 and 6078) are allowed to grow to continue to establish colonies and normalize, where the colonies of edited cells in microwells 6076 catch up in size and/or cell number with the unedited cells in microwells 6078 that do not undergo editing (vii). Note that in this workflow 6070, the colonies of cells in the microwells are not clonal; that is, not all cells in a well arise from a single cell. Instead, the cell colonies in the well may be mixed colonies, arising in many wells from two to several different cells. Once the cell colonies are normalized, either pooling 6090 of all cells in the microwells can take place, in which case the cells are enriched for edited cells by eliminating the bias from non-editing cells and fitness effects from editing; alternatively, colony growth in the microwells is monitored after editing, and slow growing colonies (e.g., the cells in microwells 6076) are identified and selected 6091 (e.g., "cherry picked") resulting in even greater enrichment of edited cells.

Figure 6C:
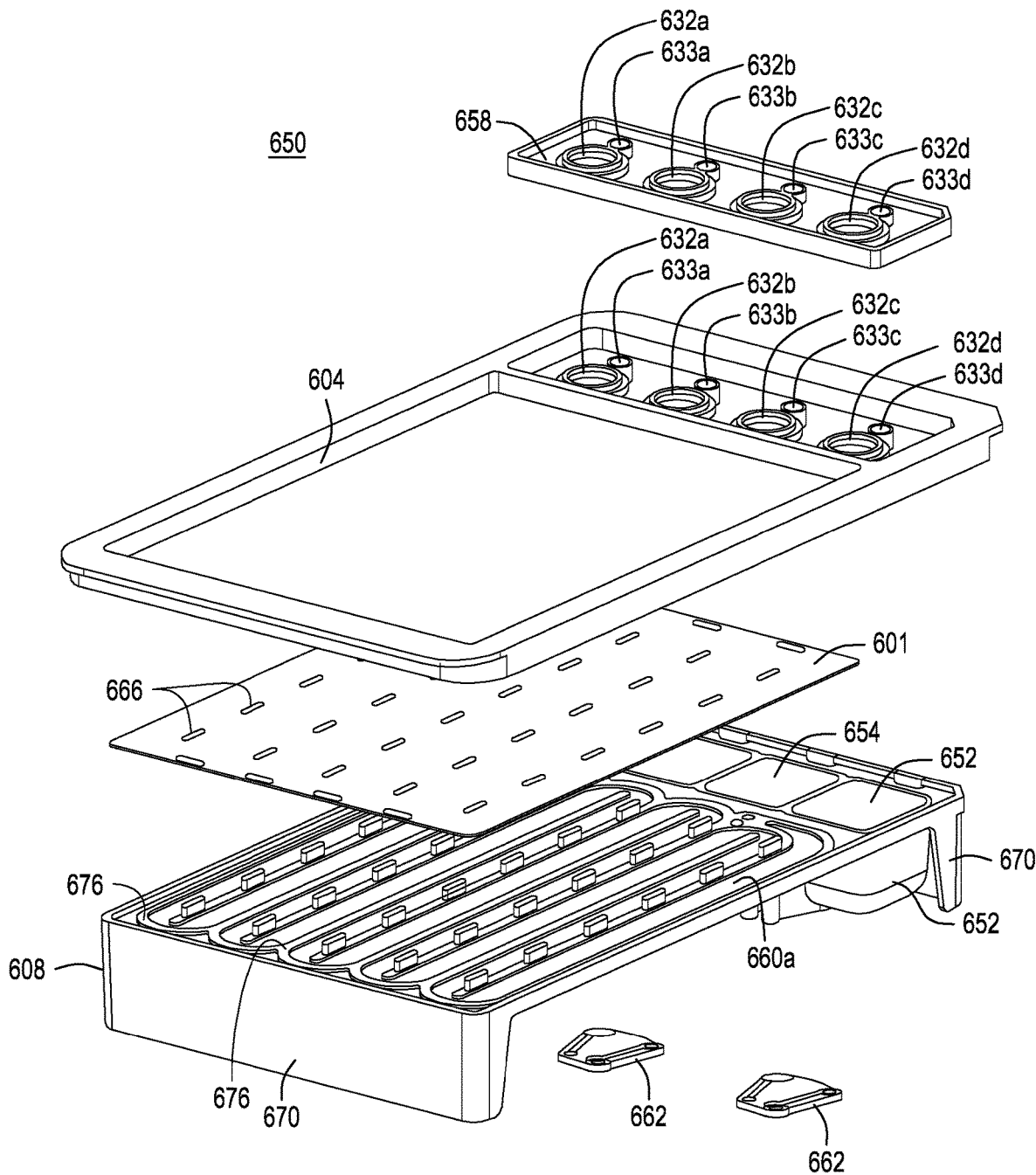

A module useful for performing the methods depicted in FIGS. 6A and 6B is a solid wall isolation, incubation, and normalization (SWIIN) module. FIG. 6C depicts an embodiment of a SWIIN module 650 from an exploded top perspective view. In SWIIN module 650 the retentate member is formed on the bottom of a top of a SWIIN module component and the permeate member is formed on the top of the bottom of a SWIIN module component.

The SWIIN module 650 in FIG. 6C comprises from the top down, a reservoir gasket or cover 658, a retentate member 604 (where a retentate flow channel cannot be seen in this FIG. 6C), a perforated member 601 swaged with a filter (filter not seen in FIG. 6C), a permeate member 608 comprising integrated reservoirs (permeate reservoirs 652 and retentate reservoirs 654), and two reservoir seals 662, which seal the bottom of permeate reservoirs 652 and retentate reservoirs 654. A permeate channel 660a can be seen disposed on the top of permeate member 608, defined by a raised portion 676 of serpentine channel 660a, and ultrasonic tabs can be seen disposed on the top of permeate member 608 as well. The perforations that form the wells on perforated member 601 are not seen in this FIG. 6C; however, through-holes 666 to accommodate the ultrasonic tabs 664 are seen. In addition, supports 670 are disposed at either end of SWIIN module 650 to support SWIIN module 650 and to elevate permeate member 608 and retentate member 604 above reservoirs 652 and 654 to minimize bubbles or air entering the fluid path from the permeate reservoir to serpentine channel 660a or the fluid path from the retentate reservoir to serpentine channel 660b (neither fluid path is seen in this FIG. 6C).

In this FIG. 6C, it can be seen that the serpentine channel 660a that is disposed on the top of permeate member 608 traverses permeate member 608 for most of the length of permeate member 608 except for the portion of permeate member 608 that comprises permeate reservoirs 652 and retentate reservoirs 654 and for most of the width of permeate member 608. As used herein with respect to the distribution channels in the retentate member or permeate member, "most of the length" means about 95% of the length of the retentate member or permeate member, or about 90%, 85%, 80%, 75%, or 70% of the length of the retentate member or permeate member. As used herein with respect to the distribution channels in the retentate member or permeate member, "most of the width" means about 95% of the width of the retentate member or permeate member, or about 90%, 85%, 80%, 75%, or 70% of the width of the retentate member or permeate member.

In this embodiment of a SWIIN module, the perforated member includes through-holes to accommodate ultrasonic tabs disposed on the permeate member. Thus, in this embodiment the perforated member is fabricated from 316 stainless steel, and the perforations form the walls of microwells while a filter or membrane is used to form the bottom of the microwells. Typically, the perforations (microwells) are approximately 150 µm-200 µm in diameter, and the perforated member is approximately 125 µm deep, resulting in microwells having a volume of approximately 2.5 nl, with a total of approximately 200,000 microwells. The distance between the microwells is approximately 279 µm center-to-center. Though here the microwells have a volume of approximately 2.5 nl, the volume of the microwells may be from 1 to 25 nl, or preferably from 2 to 10 nl, and even more preferably from 2 to 4 nl. As for the filter or membrane, like the filter described previously, filters appropriate for use are solvent resistant, contamination free during filtration, and are able to retain the types and sizes of cells of interest. For example, in order to retain small cell types such as bacterial cells, pore sizes can be as low as 0.10 µm, however for other cell types (e.g., such as for mammalian cells), the pore sizes can be as high as 10.0 µm-20.0 µm or more. Indeed, the pore sizes useful in the cell concentration device/module include filters with sizes from 0.10 µm, 0.11 µm, 0.12 µm, 0.13 µm, 0.14 µm, 0.15 µm, 0.16 µm, 0.17 µm, 0.18 µm, 0.19 µm, 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable material including cellulose mixed ester (cellulose nitrate and acetate) (CME), polycarbonate (PC), polyvinylidene fluoride (PVDF), polyethersulfone (PES), polytetrafluoroethylene (PTFE), nylon, or glass fiber.

The cross-section configuration of the mated serpentine channel may be round, elliptical, oval, square, rectangular, trapezoidal, or irregular. If square, rectangular, or another shape with generally straight sides, the cross section may be from about 2 mm to 15 mm wide, or from 3 mm to 12 mm wide, or from 5 mm to 10 mm wide. If the cross section of the mated serpentine channel is generally round, oval or elliptical, the radius of the channel may be from about 3 mm to 20 mm in hydraulic radius, or from 5 mm to 15 mm in hydraulic radius, or from 8 mm to 12 mm in hydraulic radius.

Serpentine channels 660a and 660b can have approximately the same volume or a different volume. For example, each "side" or portion 660a, 660b of the serpentine channel may have a volume of, e.g., 2 mL, or serpentine channel 660a of permeate member 608 may have a volume of 2 mL, and the serpentine channel 660b of retentate member 604 may have a volume of, e.g., 3 mL. The volume of fluid in the serpentine channel may range from about 2 mL to about 80 mL, or about 4 mL to 60 mL, or from 5 mL to 40 mL, or from 6 mL to 20 mL (note these volumes apply to a SWIIN module comprising a, e.g., 50-500K perforation member). The volume of the reservoirs may range from 5 mL to 50 mL, or from 7 mL to 40 mL, or from 8 mL to 30 mL or from 10 mL to 20 mL, and the volumes of all reservoirs may be the same or the volumes of the reservoirs may differ (e.g., the volume of the permeate reservoirs is greater than that of the retentate reservoirs).

The serpentine channel portions 660a and 660b of the permeate member 608 and retentate member 604, respectively, are approximately 200 mm long, 130 mm wide, and 4 mm thick, though in other embodiments, the retentate and permeate members can be from 75 mm to 400 mm in length, or from 100 mm to 300 mm in length, or from 150 mm to 250 mm in length; from 50 mm to 250 mm in width, or from 75 mm to 200 mm in width, or from 100 mm to 150 mm in width; and from 2 mm to 15 mm in thickness, or from 4 mm to 10 mm in thickness, or from 5 mm to 8 mm in thickness. Embodiments the retentate (and permeate) members may be fabricated from PMMA (poly(methyl methacrylate) or other materials may be used, including polycarbonate, cyclic olefin co-polymer (COC), glass, polyvinyl chloride, polyethylene, polyamide, polypropylene, polysulfone, polyurethane, and co-polymers of these and other polymers. Preferably at least the retentate member is fabricated from a transparent material so that the cells can be visualized (see, e.g., FIG. 6F and the description thereof). For example, a video camera may be used to monitor cell growth by, e.g., density change measurements based on an image of an empty well, with phase contrast, or if, e.g., a chromogenic marker, such as a chromogenic protein, is used to add a distinguishable color to the cells. Chromogenic markers such as blitzen blue, dreidel teal, virginia violet, vixen purple, prancer purple, tinsel purple, maccabee purple, donner magenta, cupid pink, seraphina pink, scrooge orange, and leor orange (the Chromogenic Protein Paintbox, all available from ATUM (Newark, Calif.)) obviate the need to use fluorescence, although fluorescent cell markers, fluorescent proteins, and chemiluminescent cell markers may also be used.

Because the retentate member preferably is transparent, colony growth in the SWIIN module can be monitored by automated devices such as those sold by JoVE (ScanLag™ system, Cambridge, Mass.) (also see Levin-Reisman, et al., Nature Methods, 7:737-39 (2010)). Cell growth for, e.g., mammalian cells may be monitored by, e.g., the growth monitor sold by IncuCyte (Ann Arbor, Mich.) (see also, Choudhry, PLos One, 11(2):e0148469 (2016)). Further, automated colony pickers may be employed, such as those sold by, e.g., TECAN (Pickolo™ system, Mannedorf, Switzerland); Hudson Inc. (RapidPick™, Springfield, N.J.); Molecular Devices (QPix 400™ system, San Jose, Calif.); and Singer Instruments (PIXL™ system, Somerset, UK).

Due to the heating and cooling of the SWIIN module, condensation may accumulate on the retentate member which may interfere with accurate visualization of the growing cell colonies. Condensation of the SWIIN module 650 may be controlled by, e.g., moving heated air over the top of (e.g., retentate member) of the SWIIN module 650, or by applying a transparent heated lid over at least the serpentine channel portion 660b of the retentate member 604. See, e.g., FIG. 6F and the description thereof infra.

In SWIIN module 650 cells and medium—at a dilution appropriate for Poisson or substantial Poisson distribution of the cells in the microwells of the perforated member—are flowed into serpentine channel 660b from ports in retentate member 604, and the cells settle in the microwells while the medium passes through the filter into serpentine channel 660a in permeate member 608. The cells are retained in the microwells of perforated member 601 as the cells cannot travel through filter 603. Appropriate medium may be introduced into permeate member 608 through permeate ports 611. The medium flows upward through filter 603 to nourish the cells in the microwells (perforations) of perforated member 601. Additionally, buffer exchange can be effected by cycling medium through the retentate and permeate members. In operation, the cells are deposited into the microwells, are grown for an initial, e.g., 2-100 doublings, editing is induced by, e.g., raising the temperature of the SWIIN to 42° C. to induce a temperature inducible promoter or by removing growth medium from the permeate member and replacing the growth medium with a medium comprising a chemical component that induces an inducible promoter.

Once editing has taken place, the temperature of the SWIIN may be decreased, or the inducing medium may be removed and replaced with fresh medium lacking the chemical component thereby de-activating the inducible promoter. The cells then continue to grow in the SWIIN module 650 until the growth of the cell colonies in the microwells is normalized. For the normalization protocol, once the colonies are normalized, the colonies are flushed from the microwells by applying fluid or air pressure (or both) to the permeate member serpentine channel 660a and thus to filter 603 and pooled. Alternatively, if cherry picking is desired, the growth of the cell colonies in the microwells is monitored, and slow-growing colonies are directly selected; or, fast-growing colonies are eliminated.

Figure 6D:
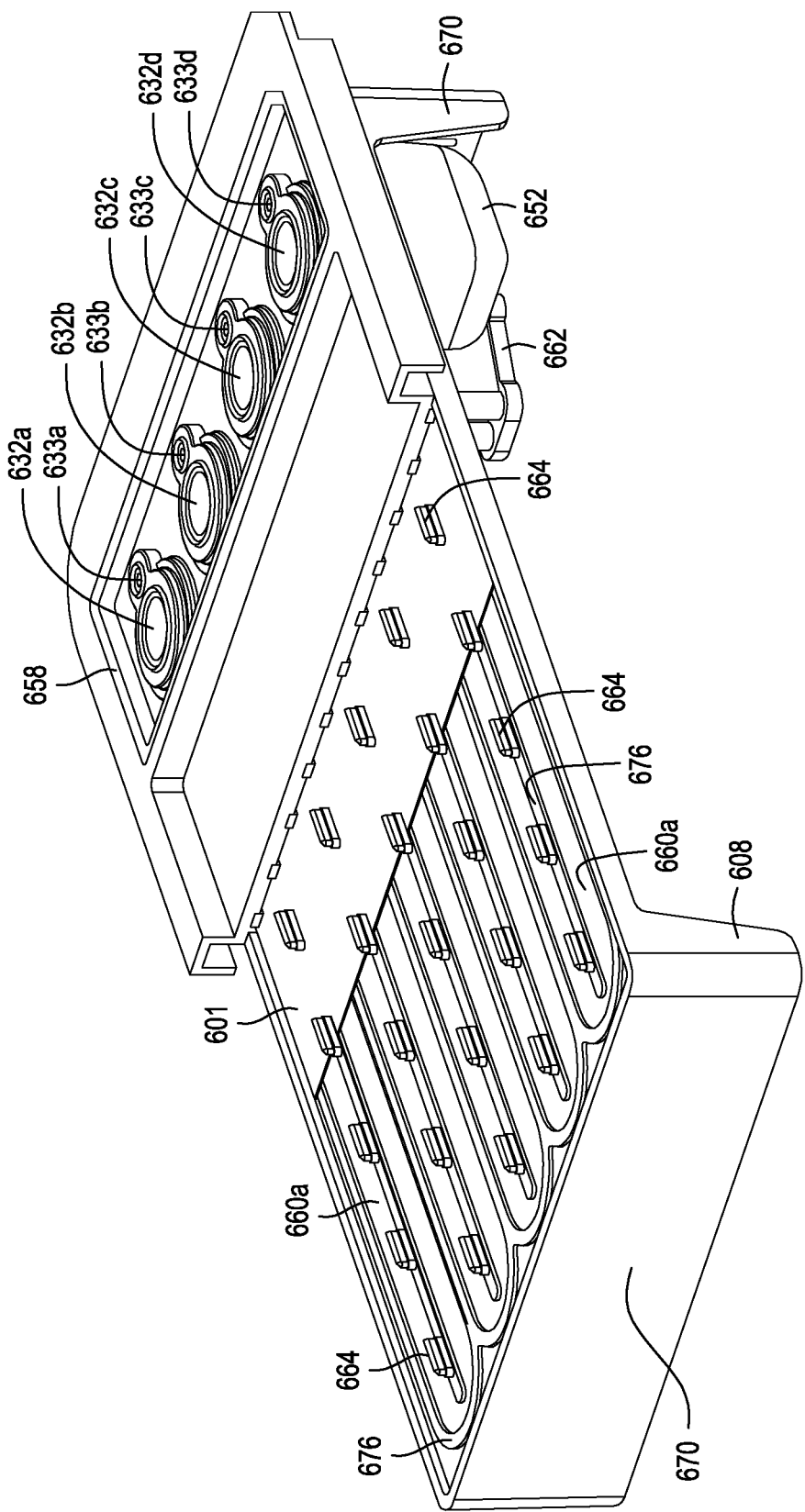

FIG. 6D is a top perspective view of a SWIIN module with the retentate and perforated members in partial cross section. In this FIG. 6D, it can be seen that serpentine channel 660a is disposed on the top of permeate member 608 is defined by raised portions 676 and traverses permeate member 608 for most of the length and width of permeate member 608 except for the portion of permeate member 608 that comprises the permeate and retentate reservoirs (note only one retentate reservoir 652 can be seen). Moving from left to right, reservoir gasket 658 is disposed upon the integrated reservoir cover 678 (cover not seen in this FIG. 6D) of retentate member 604. Gasket 658 comprises reservoir access apertures 632a, 632b, 632c, and 632d, as well as pneumatic ports 633a, 633b, 633c and 633d. Also at the far left end is support 670. Disposed under permeate reservoir 652 can be seen one of two reservoir seals 662. In addition to the retentate member being in cross section, the perforated member 601 and filter 603 (filter 603 is not seen in this FIG. 6D) are in cross section. Note that there are a number of ultrasonic tabs 664 disposed at the right end of SWIIN module 650 and on raised portion 676 which defines the channel turns of serpentine channel 660a, including ultrasonic tabs 664 extending through through-holes 666 of perforated member 601. There is also a support 670 at the end distal reservoirs 652, 654 of permeate member 608.

Figure 6E:
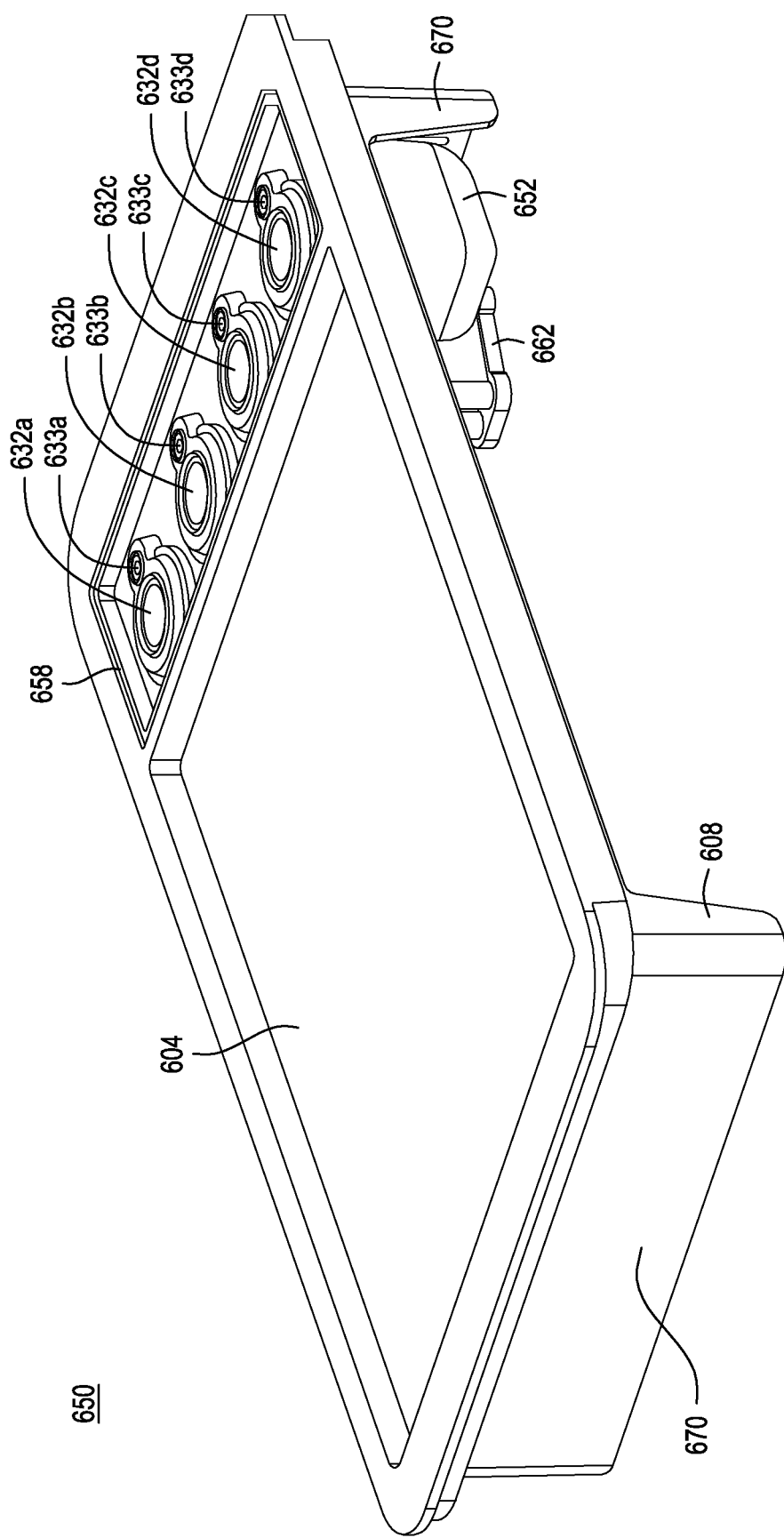

FIG. 6E is a side perspective view of an assembled SWIIN module 650, including, from right to left, reservoir gasket 658 disposed upon integrated reservoir cover 678 (not seen) of retentate member 604. Gasket 658 may be fabricated from rubber, silicone, nitrile rubber, polytetrafluoroethylene, a plastic polymer such as polychlorotrifluoroethylene, or other flexible, compressible material. Gasket 658 comprises reservoir access apertures 632a, 632b, 632c, and 632d, as well as pneumatic ports 633a, 633b, 633c and 633d. Also at the far-left end is support 670 of permeate member 608. In addition, permeate reservoir 652 can be seen, as well as one reservoir seal 662. At the far-right end is a second support 670.

Imaging of cell colonies growing in the wells of the SWIIN is desired in most implementations for, e.g., monitoring both cell growth and device performance and imaging is necessary for cherry-picking implementations. Real-time monitoring of cell growth in the SWIIN requires backlighting, retentate plate (top plate) condensation management and a system-level approach to temperature control, air flow, and thermal management. In some implementations, imaging employs a camera or CCD device with sufficient resolution to be able to image individual wells. For example, in some configurations a camera with a 9-pixel pitch is used (that is, there are 9 pixels center-to-center for each well). Processing the images may, in some implementations, utilize reading the images in grayscale, rating each pixel from low to high, where wells with no cells will be brightest (due to full or nearly-full light transmission from the backlight) and wells with cells will be dim (due to cells blocking light transmission from the backlight). After processing the images, thresholding is performed to determine which pixels will be called "bright" or "dim", spot finding is performed to find bright pixels and arrange them into blocks, and then the spots are arranged on a hexagonal grid of pixels that correspond to the spots. Once arranged, the measure of intensity of each well is extracted, by, e.g., looking at one or more pixels in the middle of the spot, looking at several to many pixels at random or pre-set positions, or averaging X number of pixels in the spot. In addition, background intensity may be subtracted. Thresholding is again used to call each well positive (e.g., containing cells) or negative (e.g., no cells in the well). The imaging information may be used in several ways, including taking images at time points for monitoring cell growth. Monitoring cell growth can be used to, e.g., remove the "muffin tops" of fast-growing cells followed by removal of all cells or removal of cells in "rounds" as described above, or recover cells from specific wells (e.g., slow-growing cell colonies); alternatively, wells containing fast-growing cells can be identified and areas of UV light covering the fast-growing cell colonies can be projected (or rastered with shutters) onto the SWIIN to irradiate or inhibit growth of those cells. Imaging may also be used to assure proper fluid flow in the serpentine channel 660.

Figure 6F:
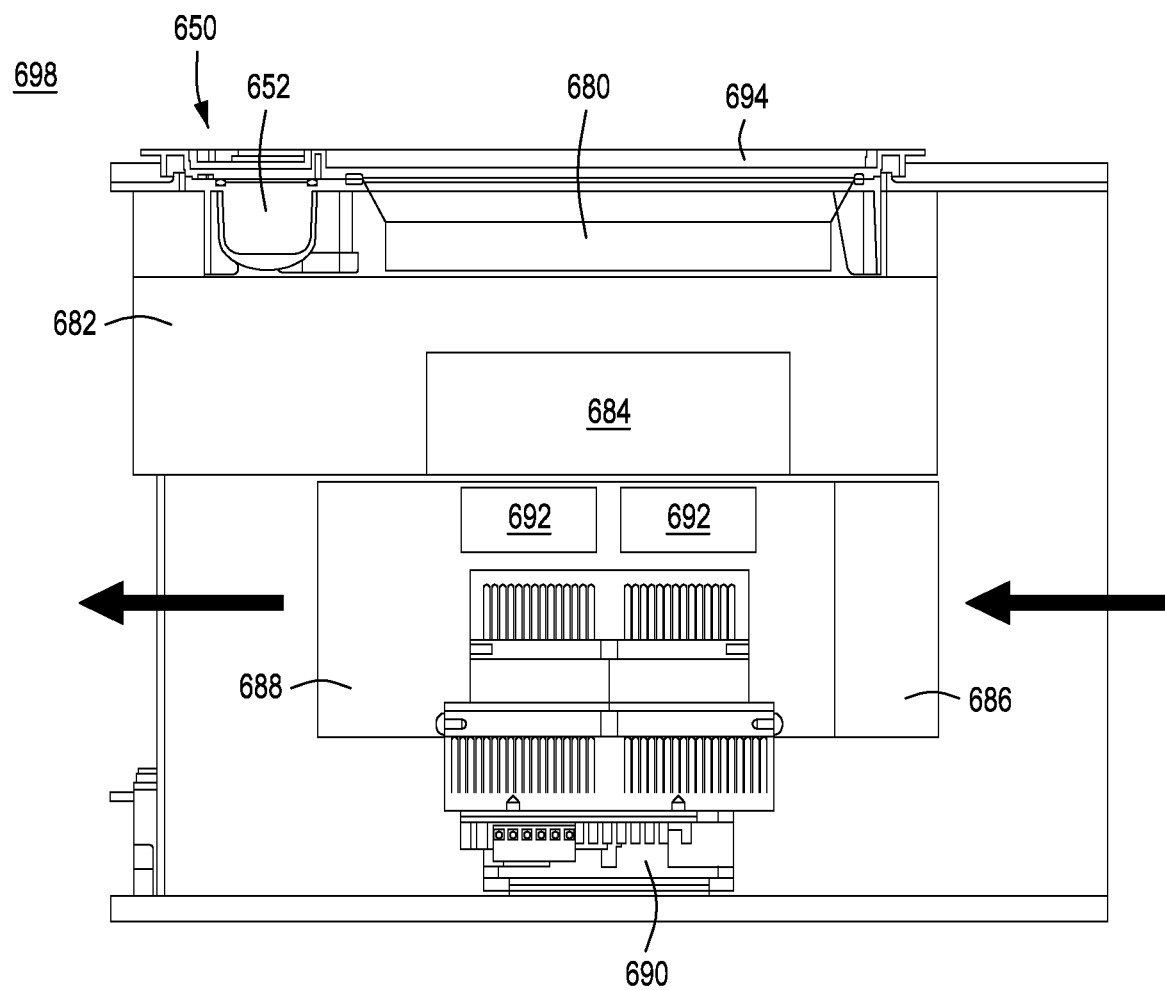

FIG. 6F depicts the embodiment of the SWIIN module in FIGS. 6A-6E further comprising a heat management system including a heater and a heated cover. The heater cover facilitates the condensation management that is required for imaging. Assembly 698 comprises a SWIIN module 650 seen lengthwise in cross section, where one permeate reservoir 652 is seen. Disposed immediately upon SWIIN module 650 is cover 694 and disposed immediately below SWIIN module 650 is backlight 680, which allows for imaging. Beneath and adjacent to the backlight and SWIIN module is insulation 682, which is disposed over a heatsink 684. In this FIG. 6F, the fins of the heatsink would be in-out of the page. In addition there is also axial fan 686 and heat sink 688, as well as two thermoelectric coolers 692, and a controller 690 to control the pneumatics, thermoelectric coolers, fan, solenoid valves, etc. The arrows denote cool air coming into the unit and hot air being removed from the unit. It should be noted that control of heating allows for growth of many different types of cells (prokaryotic and eukaryotic) as well as strains of cells that are, e.g., temperature sensitive, etc., and allows use of temperature-sensitive promoters. Temperature control allows for protocols to be adjusted to account for differences in transformation efficiency, cell growth and viability. For more details regarding solid wall isolation incubation and normalization devices see U.S. Ser. No. 16/399,988, filed 30 Apr. 2019; Ser. No. 16/454,865, filed 26 Jun. 2019; and Ser. No. 16/540,606, filed 14 Aug. 2019. For alternative isolation, incubation and normalization modules, see U.S. Ser. No. 16/536,049, filed 8 Aug. 2019.

Cell Selection Module

The split protein reporter system described herein provides fluorescent or bioluminescent cells as a read out for properly-edited cells. The properly-edited cells can be sorted from non-edited or improperly-edited cells via fluorescence-activated cell sorting (FACS). FACs is a derivative of flow cytometry that adds an enhanced degree of functionality. Using FACs, a heterogenous mixture of live cells can be sorted into different populations. FACs is the only available purification technique to isolate cells based on internal staining or intracellular protein expression, and allows for the purification of individual cells based on size, granularity and fluorescence. Cells in suspension are passed as a stream in droplets with each droplet containing a single cell of interest. The droplets are passed in front of a laser. An optical detection system detects cells of interest based on predetermined optical parameters (e.g., fluorescent or bioluminescent parameters). The instrument applies a charge to a droplet containing a cell of interest and an electrostatic deflection system facilitates collection of the charged droplets into appropriate tubes or wells. Sorting parameters may be adjusted depending on the requirement of purity and yield. Using the split protein reporter system, properly-edited cells are bioluminescent and improperly- or un-edited cells are not bioluminescent; thus, the desired cells are easily sorted from unwanted cells.

Use of the Automated Multi-Module Cell Processing Instrument

Figure 7:
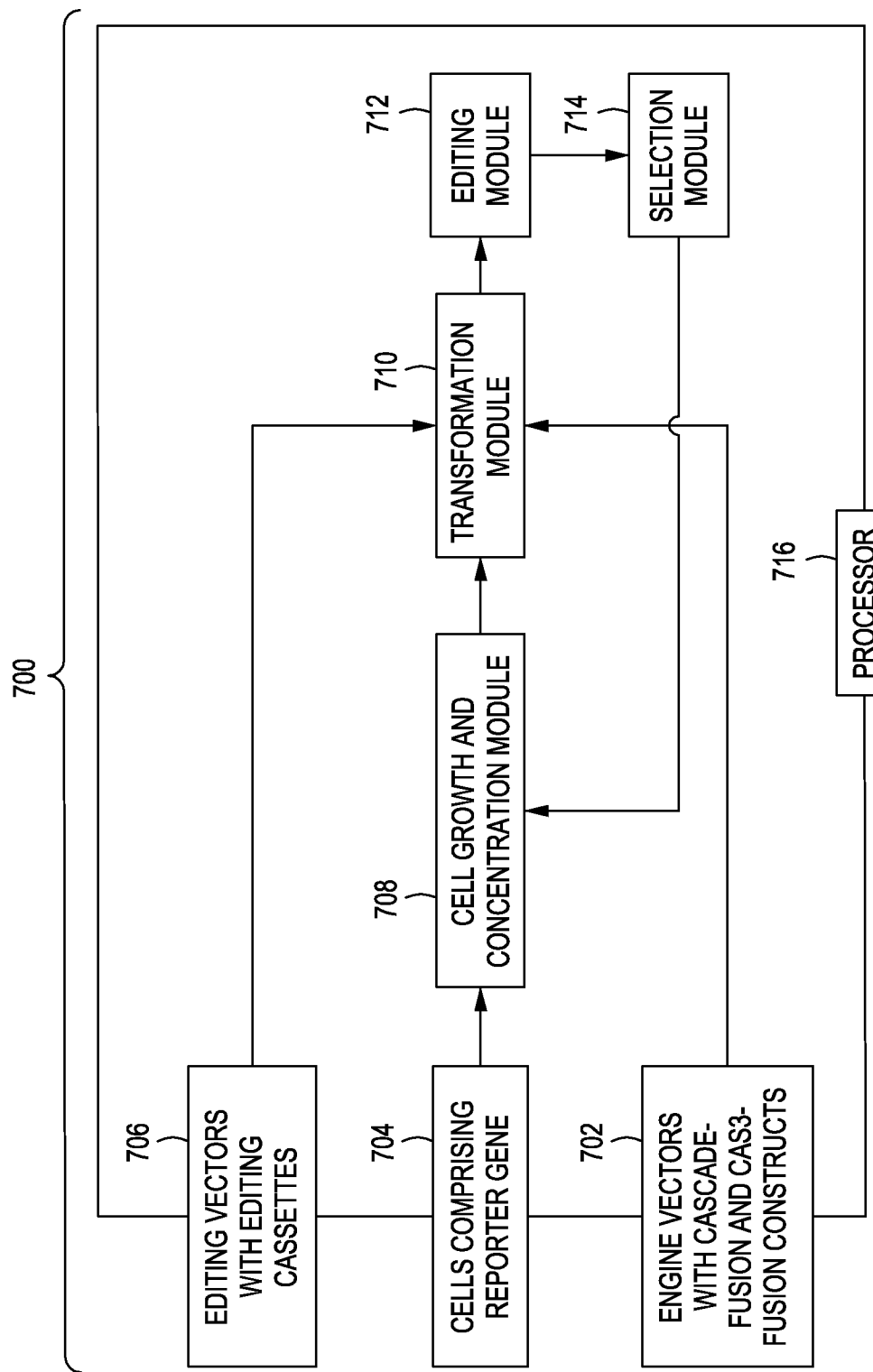
FIG. 7 is a simplified process diagram of an embodiment of an exemplary automated multi-module cell processing instrument in which the split protein reporter system described herein may be used.
Figure 8A:
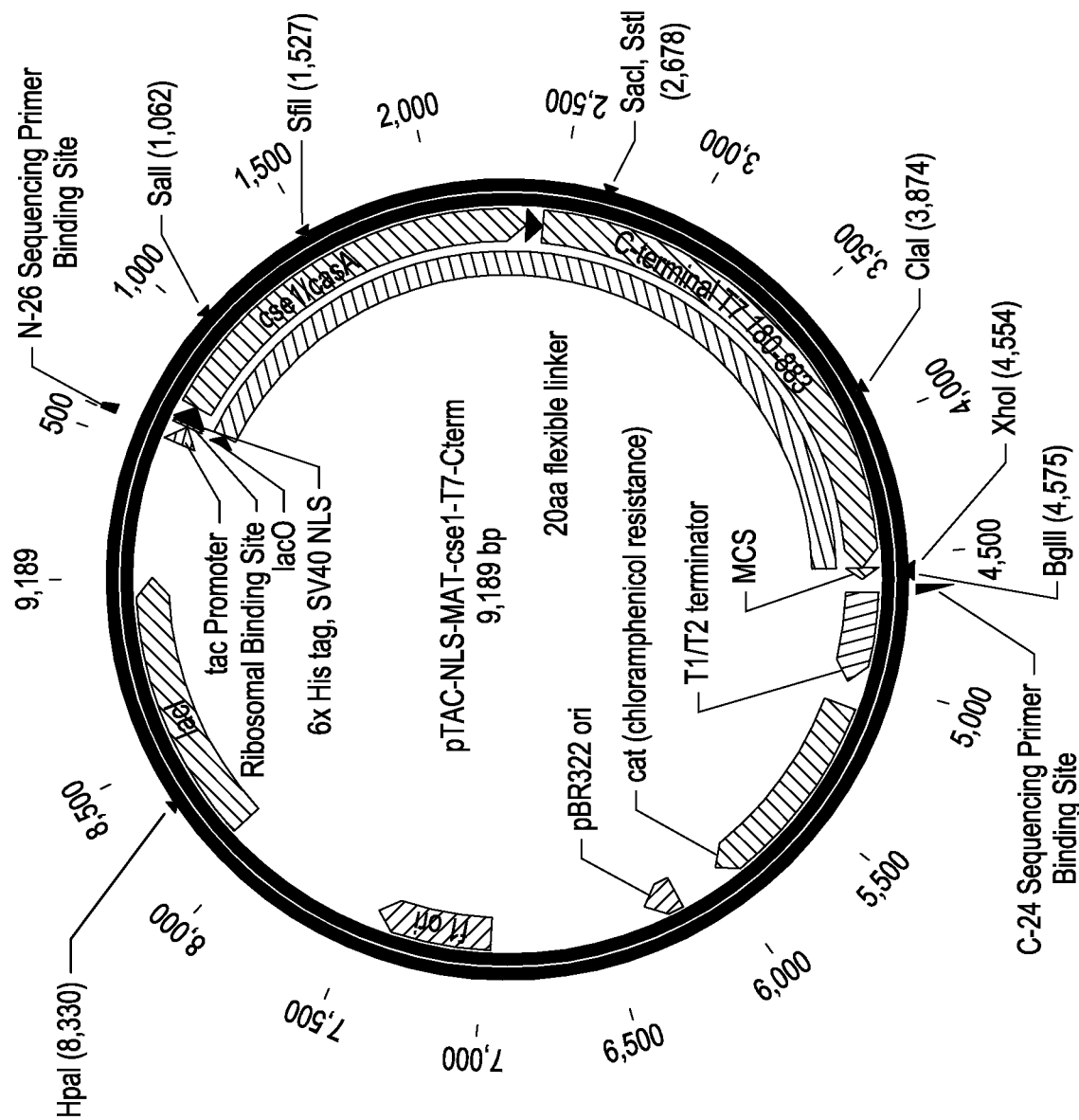
FIG. 8A-8D comprise exemplary vector maps for testing the split protein reporter system in *E. coli*.
Figure 8B:
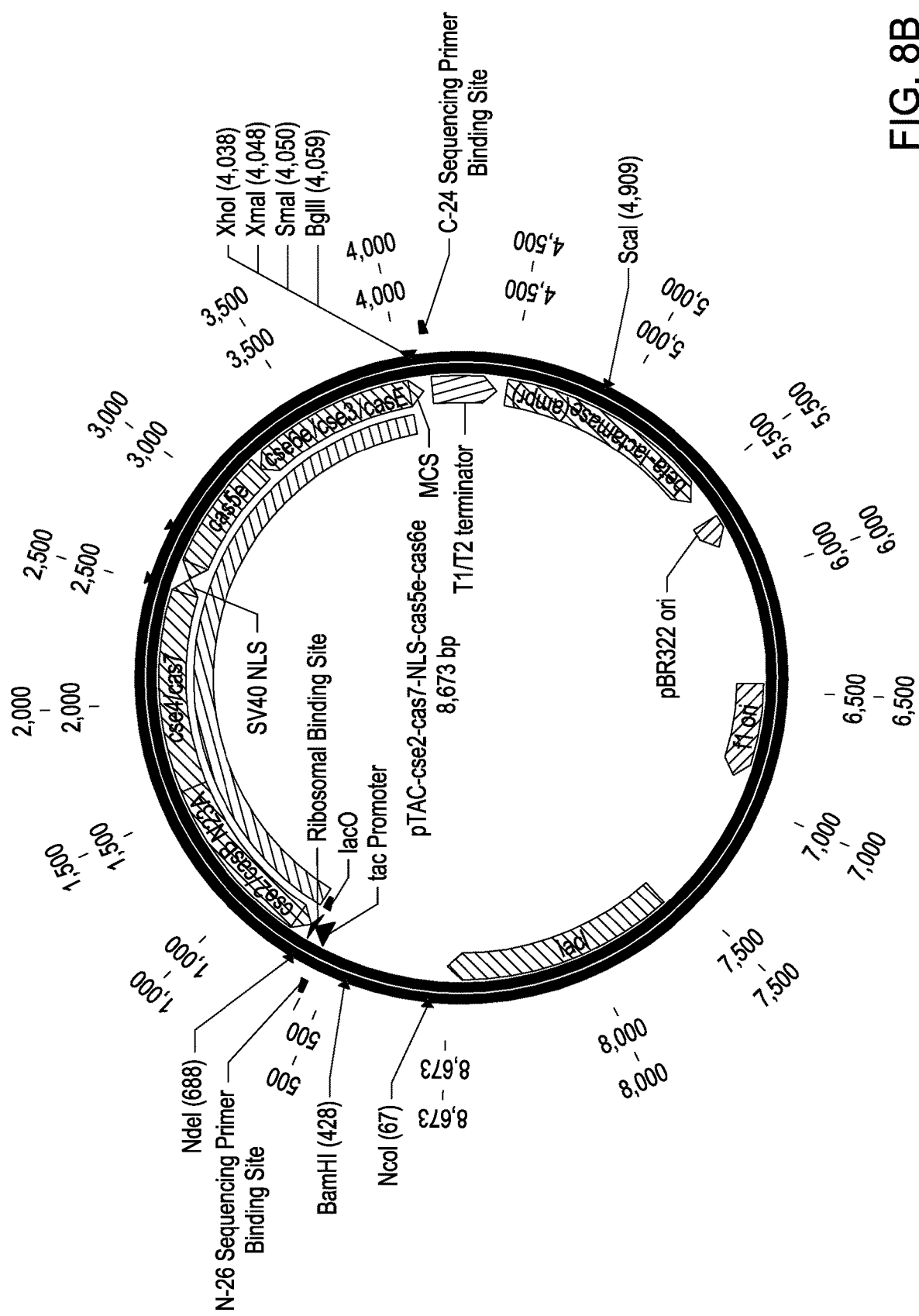
Figure 8C:
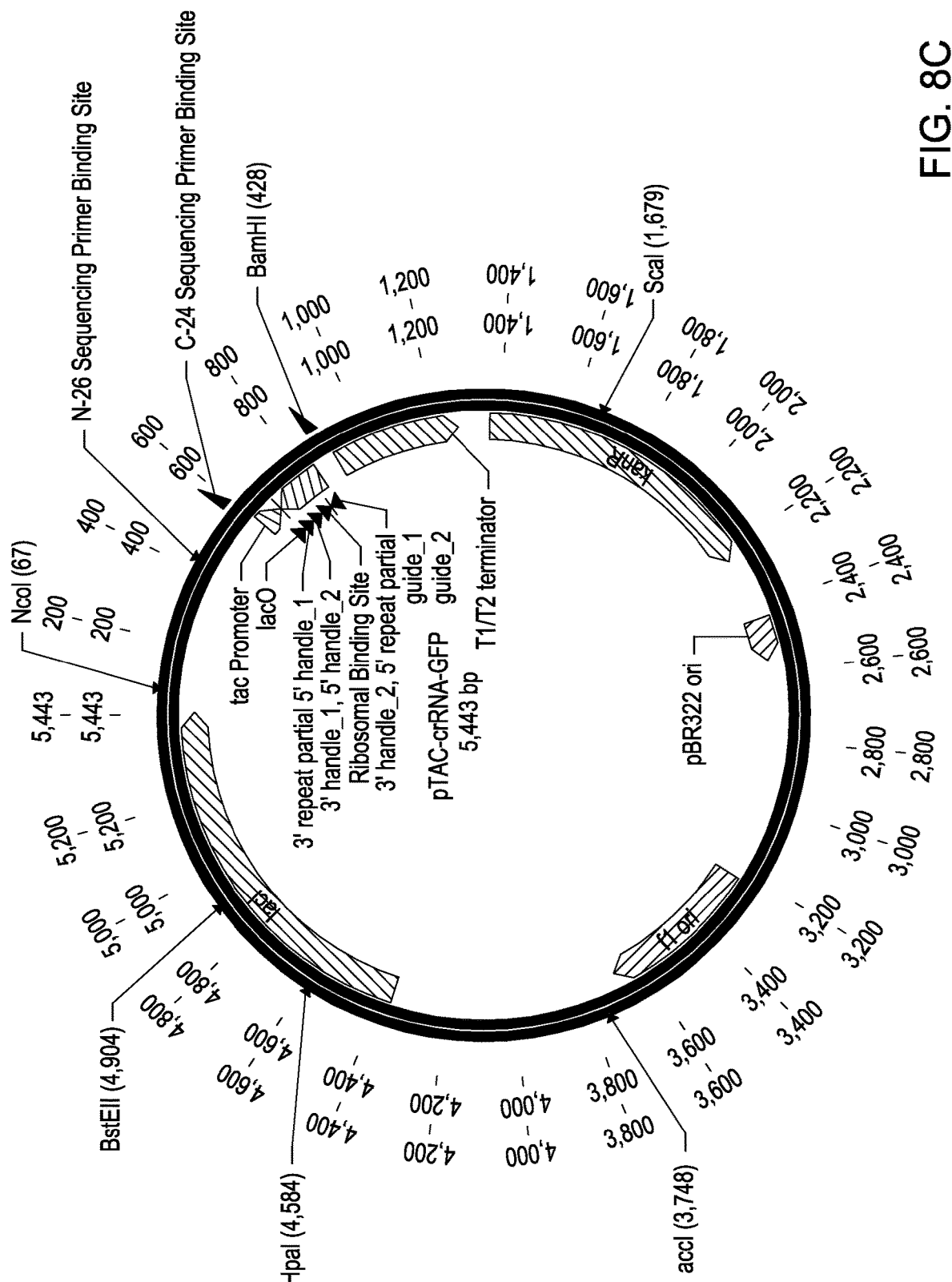
Figure 8D:
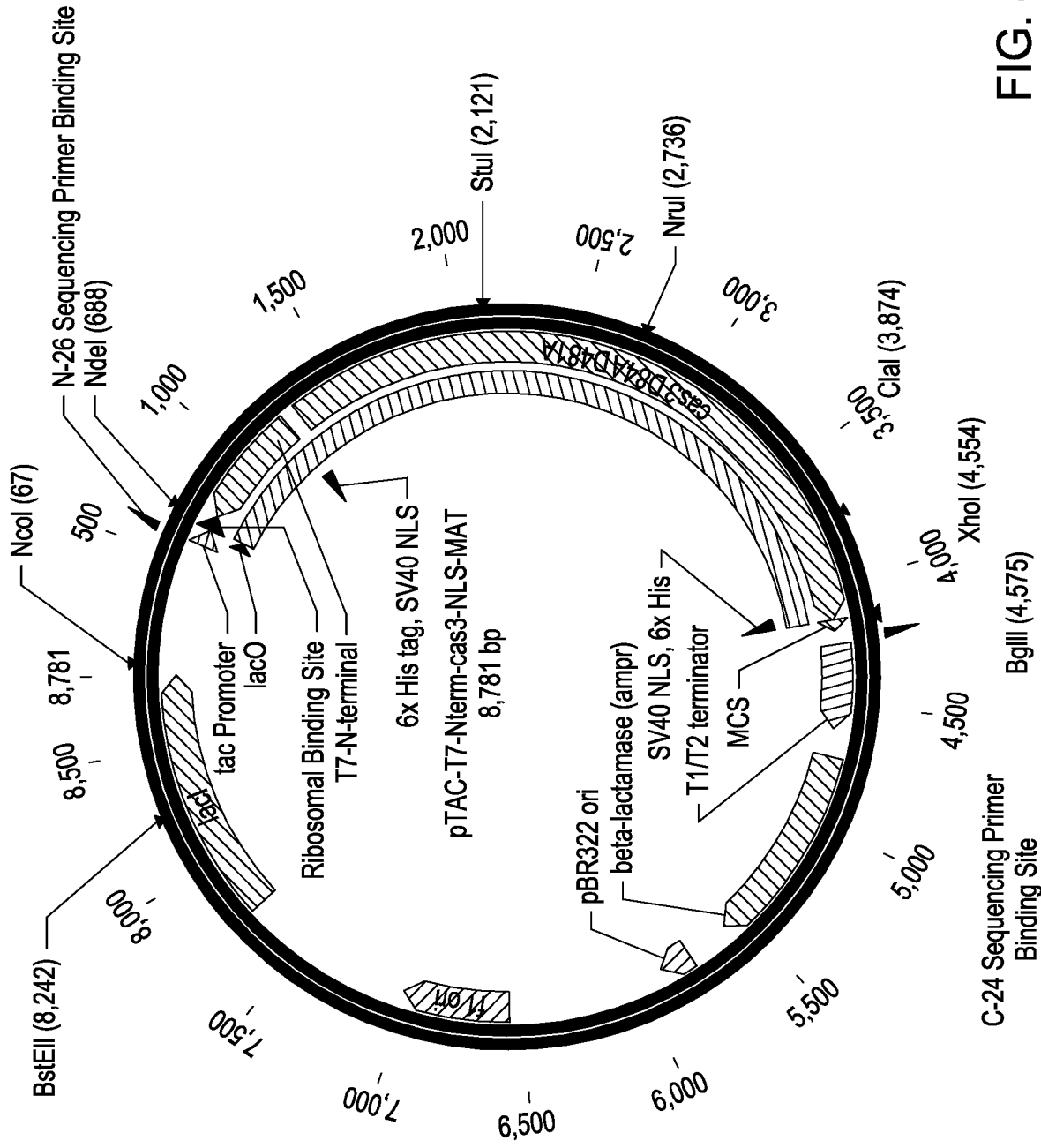

One embodiment of an automated multi-module cell processing instrument capable of performing the methods described herein is shown in FIG. 7. The cell processing instrument 700 may include a housing, a reservoir of cells in, e.g., the reagent cartridge where the cells are to be transformed 704. The cells are transferred from the reservoir to the cell growth and concentration module 708. In this embodiment, the cell growth and concentration module is a single module, such as a TFF; however, in other embodiments the cell growth and concentration modules may be separate, such as a cell growth module comprising a rotating growth module and a cell concentration device comprising a TFF. The cells to be processed are transferred from, e.g., a reservoir in the reagent cartridge to the cell growth module 708 to be cultured until the cells hit a target OD. Once the cells hit the target OD, the cell growth module may cool the cells for later processing or the cells may progress directly to cell concentration, where buffer or medium exchange is performed, the cells are rendered competent, and the volume of the cells is reduced to a volume optimal for cell transformation in a transformation module 710. The transformation module 710 may be, e.g., a flow-through electroporation device.

In addition to the reservoir for storing the cells, the reagent cartridge may include a reservoir for storing editing vectors 706 comprising editing cassettes and a reservoir for storing an engine vector 702 comprising, e.g., a coding sequence for a nuclease and coding sequences for the Cascade-C-terminal T7 RNAP fusion construct and the dCas3-N-terminal T7 RNAP fusion construct. As described above in relation to FIG. 1A, the Cascade-C-terminal T7 RNAP fusion construct and the dCas3-N-terminal T7 RNAP fusion construct may located on the engine vector (e.g., the vector comprising the coding sequence for the nuclease), the Cascade-C-terminal T7 RNAP fusion construct and the dCas3-N-terminal T7 RNAP fusion construct may both be located on a single reporter vector along with the reporter gene under the control of a T7 promoter, or the various components of the split protein system may be on different reporter vectors, on the editing vector, and/or on the engine vector. The editing vector, engine vector and reporter vectors (if separate, not shown) are then transferred to the transformation module 710 to be electroporated into the cells.

Once the cells have been transformed, the cells may be transferred to an editing module 712, such as a SWIIN module as described above, for editing. In addition, selection may be performed in a separate module between the transformation module and the editing module, or selection may be performed in the editing module. Selection in this instance refers to selecting for cells that have been properly transformed with vectors that comprise selection markers, thus assuring that the cells have received all vectors for both nucleic acid-guided nuclease editing and for reporting proper edits. After selection, conditions are provided for editing. If any components of the nucleic acid-guided nuclease editing system are under the control of an inducible promoter, conditions are provided to activate the inducible promoters for editing. While the cells are editing, the split protein reporter system may be active, wherein cells that have been properly edited are emitting light; alternatively, one or both of the fusion constructs (e.g., the Cascade-C-terminal T7 RNAP fusion construct or the dCas3-N-terminal T7 RNAP fusion construct) and/or the edit-discriminating gRNA may be under the control of an inducible promoter, and the split protein reporter system is not activated until the cells have been edited. Whether during or after editing, the split protein reporter system when active allows for identification of cells that have been properly edited via bioluminescence. Following editing, the cells are transferred to a selection module 714, where the cells can be sorted.

Cells in which the split protein reporter system is active (e.g., luminescent cells) and have been separated from cells that are not luminescent can then be grown and prepared for another round of editing. The multi-module cell processing instrument is controlled by a processor 716 configured to operate the instrument based on user input, as directed by one or more scripts, or as a combination of user input or a script. The processor 716 may control the timing, duration, temperature, and operations of the various modules of the instrument 700 and the dispensing of reagents from the reagent cartridge. The processor may be programmed with standard protocol parameters from which a user may select, a user may specify one or more parameters manually or one or more scripts associated with the reagent cartridge may specify one or more operations and/or reaction parameters. In addition, the processor may notify the user (e.g., via an application to a smart phone or other device) that the cells have reached a target OD, been rendered competent and concentrated, and/or update the user as to the progress of the cells in the various modules in the multi-module instrument.

For examples of multi-module cell editing instruments, see U.S. Pat. No. 10,253,316, issued 9 Apr. 2019; U.S. Pat. No. 10,329,559, issued 25 Jun. 2019; U.S. Pat. No. 10,323,242, issued 18 Jun. 2019; U.S. Pat. No. 10,421,959, issued 24 Sep. 2019; U.S. Pat. No. 10,465,185, issued 5 Nov. 2019; and U.S. Ser. No. 16/412,195, filed 14 May 2019; Ser. No. 16/571,091, filed 14 Sep. 2019; and Ser. No. 16/666,964, filed 29 Oct. 2019, all of which are herein incorporated by reference in their entirety.

It should be apparent to one of ordinary skill in the art given the present disclosure that the process described may be recursive and multiplexed; that is, cells may go through the workflow described in relation to FIG. 7, then the resulting edited culture may go through another (or several or many) rounds of additional editing (e.g., recursive editing) with different editing vectors. For example, the cells from round 1 of editing may be diluted and an aliquot of the edited cells edited by editing vector A may be combined with editing vector B, an aliquot of the edited cells edited by editing vector A may be combined with editing vector C, an aliquot of the edited cells edited by editing vector A may be combined with editing vector D, and so on for a second round of editing. After round two, an aliquot of each of the double-edited cells may be subjected to a third round of editing, where, e.g., aliquots of each of the AB-, AC-, AD-edited cells are combined with additional editing vectors, such as editing vectors X, Y, and Z. That is that double-edited cells AB may be combined with and edited by vectors X, Y, and Z to produce triple-edited edited cells ABX, ABY, and ABZ; double-edited cells AC may be combined with and edited by vectors X, Y, and Z to produce triple-edited cells ACX, ACY, and ACZ; and double-edited cells AD may be combined with and edited by vectors X, Y, and Z to produce triple-edited cells ADX, ADY, and ADZ, and so on. In this process, many permutations and combinations of edits can be executed, leading to very diverse cell populations and cell libraries.

In any recursive process, it is advantageous to "cure" the previous engine and editing vectors (or single engine+editing vector in a single vector system). "Curing" is a process in which one or more vectors used in the prior round of editing is eliminated from the transformed cells. Curing can be accomplished by, e.g., cleaving the vector(s) using a curing plasmid thereby rendering the editing and/or engine vector (or single, combined engine/editing vector) nonfunctional; diluting the vector(s) in the cell population via cell growth (that is, the more growth cycles the cells go through, the fewer daughter cells will retain the editing or engine vector(s)), or by, e.g., utilizing a heat-sensitive origin of replication on the editing or engine vector (or combined engine+editing vector). The conditions for curing will depend on the mechanism used for curing; that is, in this example, how the curing plasmid cleaves the editing and/or engine vector.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example I: Fully-Automated Singleplex RGN-Directed Editing Run

Singleplex automated genomic editing using MAD7 nuclease was successfully performed with an automated multi-module instrument of the disclosure. See U.S. Pat. No. 9,982,279; and U.S. Ser. No. 16/024,831 filed 30 Jun. 2018; Ser. No. 16/024,816 filed 30 Jun. 2018; Ser. No. 16/147,353 filed 28 Sep. 2018; Ser. No. 16/147,865 filed 30 Sep. 2018; and Ser. No. 16/147,871 filed 30 Jun. 2018.

An ampR plasmid backbone and a lacZ_F172* editing cassette were assembled via Gibson Assembly® into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent E. coli cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module), and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example II: Fully-Automated Recursive Editing Run

Recursive editing was successfully achieved using the automated multi-module cell processing system. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent E. coli cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in an isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product nonfunctional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent E. coli cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

Example III: Isolation of Cells with Specified Genotypes in a Population

Following automated singleplex or recursive editing runs, a population of cells is produced that contains multiple specific genotypes corresponding to complete intended edits, incomplete edits, and unedited or wild type cells. To identify and isolate only the complete intended edits, a modified Type I CRISPR system is utilized in which two halves of a split T7 RNAP (e.g., the portions of a split protein reporter system) are fused onto the cascade complex and deactivated cas3 nuclease, respectively. After discriminatory recognition of the complete intended edit via formation of an R-loop between the cascade complex with an edit-discriminating crRNA, the deactivated cas3 fusion protein is recruited to the site of the R-loop and binds the cascade complex. This binding event brings the two halves of the split T7 RNAP into proximity forming an active T7 polymerase. The active T7 polymerase then transcribes a reporter gene.

A T. fusca XY cascade complex fused to a T7 C-terminal fragment was recombinantly expressed and purified via a three plasmid co-expression system in E. coli BL21 cells grown on LB media. The first plasmid contained the cse1 protein of the *T. fusca* XY cascade complex with a C-terminal fragment (amino acids 181-883) of the T7 RNAP polymerase fused onto the C-terminal with a 20aa flexibly GlySer linker on a pTAC-MAT-Tag1 (Sigma Aldrich) vector containing chloramphenicol resistance (see FIG. 8A). The second plasmid, on a pTAC-MAT-Tag1 vector with ampicillin resistance, contained the remaining cascade complex genes, cse2-cas7-NLS-cas5e-cas6e, with an N23A mutation on cse2 to encourage R-loop formation at 37° C. and an SV40 NLS signal on the C-terminal of the cas7 gene, to make pTAC-cse2-cas7-NLS-cas5e-cas6e (see FIG. 8B). The third plasmid contained the crRNA expressed from a synthetic CRISPR array to make pTAC-crRNA-GFP (FIG. 8C). *E. coli* BL21 cells containing all three plasmids were grown to an OD of 0.6 and expression was induced by adding IPTG to a concentration of 0.5 mM before letting cells grow overnight. Cells were then harvested, lysed using lysozyme and the cascade complex with fused T7-C-terminal RNAP was purified with Ni-NTA Agarose (Qiagen) according to manufacturer's protocol.

Separately, the deactivated *T. fusca* XY cas3 was recombinantly expressed and purified. The *T. fusca* XY cas3 D84A D481A with an N-terminal fusion of T7 RNAP (amino acids 1-179) followed by a 14aa flexible GlySer linker and a C-terminal SV40 NLS and 6×His tag was cloned into pTAC-MAT-Tag1 (Sigma Aldrich) to make pTAC-T7-Nterm-cas3-NLS-His (FIG. 8D). *E. coli* BL21 cells containing the plasmid were grown to an OD of 0.6 and expression was induced by adding IPTG to a concentration of 1 mM before letting cells grow overnight at 18° C. Cells were then lysed and the deactivated cas3-T7-Nterminal fusion was purified with Ni-NTA Agarose (Qiagen).

The pool of previously edited HEK293T-GFP cells were electroporated using the Neon Transfection system (ThermoFisher). Edited cells were trypsinized, washed with 1×DPBS (ThermoFisher) and resuspended in Neon Buffer R. 80 pmol of cascade-T7-C-terminal, 20 pmol of cas3-T7-N-terminal, and 5 pmol of F30-2xdBroccoli (pJin141) driven by the T7 promoter were mixed with approximately $1.0E^{0.5}$ cells in buffer R. The mixture was electroporated with a 10 μl Neon tip (1100V, 20 ms, 2 pulses) and plated in 24-well plates. After 72 hours cells were sorted on BD FACSMelody™ cells sorter based on the highest fluorescence to recover only cells which contained the complete intended edit programmed for by the cascade crRNA.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, 916.

We claim:

1. A method for isolating one or more cells in a population of cells with rationally designed gene edits in their genome comprising:
   introducing into the one or more cells a nucleic acid sequence encoding an editing discriminating guide RNA ("edit-discriminating gRNA"), wherein the edit-discriminating gRNA is configured to hybridize to a locus on a genome that has been rationally edited by a CRISPR enzyme, but does not hybridize to a locus on the genome that has not been rationally edited by the CRISPR enzyme;
   introducing into the one or more cells a nucleic acid sequence encoding a first half of a split system reporting protein, wherein the first half is a Cascade-T7-RNA polymerase ("Cascade-T7-RNAP") RNAP fusion protein coding sequence;
   introducing into the one or more cells a nucleic acid sequence encoding a second half of a split system reporting protein, wherein the second half is a dCas3-T7 RNA polymerase ("dCas3-T7-RNAP") fusion protein coding sequence;
   allowing the one or more cells to grow under conditions that allow:
   i) the gRNA to hybridize to one or more cells having the rationally designed gene edit; and
   ii) the Cascade-T7-RNAP, the dCas3-T7-RNAP to be brought into close proximity for forming an active T7 RNAP
   isolating by Fluorescent Activated Cell Sorting (FACS) one or more cells in the population of cells having the rationally designed gene edits by FACS sorting the one or more cells that express a fluorescent reporting gene under the control of a T7 promoter.

2. The method of claim 1, wherein the nucleic acid sequence encoding the gRNA configured to hybridize to the locus on the genome that has been rationally edited by the CRISPR enzyme, but does not hybridize to the locus on the genome that has not been rationally edited by the CRISPR enzyme is in a vector.

3. The method of claim 1, wherein the nucleic acid sequence encoding the Cascade-T7-RNAP fusion protein coding sequence is in a vector.

4. The method of claim 1, wherein the nucleic acid sequence encoding the dCas3-T7-RNAP fusion protein coding sequence is in a vector.

5. The method of claim 1, wherein the population of cells have a fluorescent reporting gene under the control of a T7 promoter.

6. The method of claim 1, wherein a nucleic acid sequence encoding a fluorescent reporting gene under the control of a T7 promoter in introduced into the cells from a vector.

7. The method of claim 1, wherein the nucleic acid coding sequences for the Cascade-T7-RNAP fusion protein, the dCas3-T7-RNAP fusion, and the edit-discriminating gRNA are on a single reporter vector.

8. The method of claim 1, wherein the Cascade-T7 RNAP fusion protein coding sequence comprises a terminus of a Cascade protein.

9. The method of claim 8, wherein the Cascade-T7 RNAP fusion protein coding sequence comprises the N-terminus of cas5c.

10. The method of claim 8, wherein the Cascade-T7 RNAP fusion protein coding sequence comprises a terminus of cse1 or casA.

11. The method of claim 8, wherein the Cascade-T7 RNAP fusion protein coding sequence comprises the C-terminus of the T7 RNAP.

12. The method of claim 11, wherein the Cascade-T7 RNAP fusion protein coding sequence comprises amino acids 181-883 of the T7 RNAP.

13. The method of claim 1, wherein the dCas3-T7 RNAP fusion protein coding sequence comprises a terminus of dCas3.

14. The method of claim 1, wherein the dCas3-T7 RNAP fusion protein coding sequence comprises the N-terminus of the T7 RNAP.

15. The method of claim 14, wherein the dCas3-T7-RNAP fusion protein coding sequence comprises amino acids 1-179 or the T7 RNAP.

16. The method of claim 1, wherein the fluorescent reporting gene encodes a fluorescent protein.

17. The method of claim 16, wherein the fluorescent protein is a green fluorescent protein or a blue fluorescent protein.

18. The method of claim 16, wherein the fluorescent protein is a firefly luciferase or *Renilla* luciferase.

19. The method of claim 1, wherein the fluorescent reporting gene encodes a broccoli RNA aptamer or a spinach RNA aptamer.

20. The method of claim 1, wherein the method allows for in vivo identification of edited cells.

\* \* \* \* \*